(12) United States Patent
Schwab et al.

(10) Patent No.: US 10,329,378 B2
(45) Date of Patent: Jun. 25, 2019

(54) GRAPHENE NANORIBBONS WITH CONTROLLED ZIG-ZAG EDGE AND COVE EDGE CONFIGURATION

(71) Applicants: BASF SE, Ludwigshafen (DE); EMPA-Eidgenoessische Materialpruefungs- und Forschungsanstalt, Duebendorf (CH); Max-Planck-Gesellschaft zur Foerderung der Wissenschaften e.V., Munich (DE)

(72) Inventors: Matthias Georg Schwab, Mannheim (DE); Klaus Muellen, Cologne (DE); Xinliang Feng, Dresden (DE); Bo Yang, Mainz (DE); Tim Dumslaff, Koblenz (DE); Roman Fasel, Zurich (CH); Pascal Ruffieux, Plasselb (CH); Jia Liu, Duebendorf (CH); Jinming Cai, Zurich (CH); Carlos Sanchez-Sanchez, Duebendorf (CH); Junzhi Liu, Mainz (DE)

(73) Assignees: BASF SE, Ludwigshafen (DE); EMPA-Eidgenoessische Materialpruefungs-und Forschungsanstalt, Duebendorf (CH); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 15/118,796

(22) PCT Filed: Feb. 9, 2015

(86) PCT No.: PCT/IB2015/050951
§ 371 (c)(1),
(2) Date: Aug. 12, 2016

(87) PCT Pub. No.: WO2015/121785
PCT Pub. Date: Aug. 20, 2015

(65) Prior Publication Data
US 2017/0051101 A1 Feb. 23, 2017

(30) Foreign Application Priority Data

Feb. 13, 2014 (EP) .................. 14155067

(51) Int. Cl.
*C07C 25/22* (2006.01)
*C08G 61/10* (2006.01)
(Continued)

(52) U.S. Cl.
CPC ............ *C08G 61/10* (2013.01); *C01B 32/184* (2017.08); *C07C 15/20* (2013.01); *C07C 25/22* (2013.01);
(Continued)

(58) Field of Classification Search
CPC ... C01B 32/184; C01B 2204/06; C07C 25/22; C07C 15/20; C08G 61/10;
(Continued)

(56) References Cited

U.S. PATENT DOCUMENTS 8,236,626 B2 8/2012 Dai et al.
2010/0047154 A1 2/2010 Lee et al.
(Continued)

FOREIGN PATENT DOCUMENTS

CN 102701196 A 10/2012
KR 10-1082335 B1 11/2011
(Continued)

OTHER PUBLICATIONS

Definition of "can," accessed online at https://www.merriam-webster.com/dictionary/can?src=search-dict-hed on Feb. 5, 2018.*
(Continued)

*Primary Examiner* — Daniel McCracken
(74) *Attorney, Agent, or Firm* — Oblon, McClelland, Maier & Neustadt, L.L.P.

(57) ABSTRACT

Provided are graphene nanoribbons with controlled zig-zag edge and cove edge configuration and methods for preparing such graphene nanoribbons. The nanoribbons are selected from the following formulae.

(Continued)

-continued

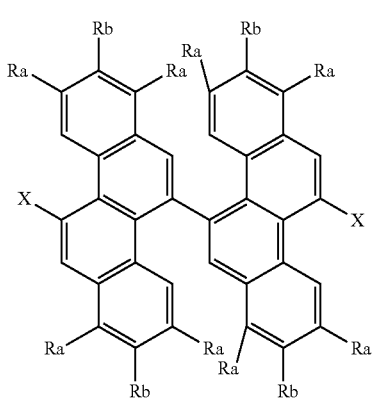

C

11 Claims, 4 Drawing Sheets

(51) Int. Cl.
  *C07C 15/20* (2006.01)
  *C01B 32/184* (2017.01)
(52) U.S. Cl.
  CPC .... *C01B 2204/06* (2013.01); *C08G 2261/312* (2013.01); *C08G 2261/314* (2013.01); *C08G 2261/72* (2013.01); *C08G 2261/724* (2013.01)
(58) Field of Classification Search
  CPC ........ C08G 2261/312; C08G 2261/724; C08G 2261/314; C08G 2261/72
  See application file for complete search history.

(56) References Cited

U.S. PATENT DOCUMENTS

| | | |
|---|---|---|
| 2011/0097258 A1 | 4/2011 | Lee et al. |
| 2011/0244661 A1 | 10/2011 | Dai et al. |
| 2011/0253969 A1 | 10/2011 | Dai et al. |
| 2011/0274928 A1 | 11/2011 | Liu |
| 2012/0261644 A1 | 10/2012 | Dimitrakopoulos et al. |
| 2013/0108839 A1 | 5/2013 | Arnold et al. |

FOREIGN PATENT DOCUMENTS

| | | |
|---|---|---|
| TW | 201331255 A | 8/2013 |
| WO | WO 2012/145101 A1 | 10/2012 |
| WO | WO 2012/149257 A2 | 11/2012 |
| WO | WO 2013/061256 A1 | 5/2013 |
| WO | WO 2013/061258 A1 | 5/2013 |
| WO | WO 2013/062774 A1 | 5/2013 |
| WO | WO 2013/072292 A1 | 5/2013 |
| WO | 2013/093756 A1 | 6/2013 |
| WO | WO 2013/175342 A1 | 11/2013 |

OTHER PUBLICATIONS

Definition of "unambiguous," accessed online at https://www.merriam-webster.com/dictionary/unambiguously on Feb. 5, 2018.*
International Search Report and Written Opinion dated Jun. 15, 2016 in PCT/IB2015/050951 filed Feb. 9, 2015.
Katsunori Wakabayashi, et al., "Edge Effect on Electronic Transport Properties of Graphene nanoribbons and Presence of Perfectly Conducting Channel", Carbon, vol. 47, No. 1, Sep. 26, 2008, 14 pages.
Mitsutaka Fujita, et al., "Peculiar Localized State at Zigzag Graphite Edge", Journal of the Physical Society of Japan, vol. 65, No. 7, 1996, pp. 1920-1923.
Katsunori Wakabayashi, et al., "Electronic states of graphene nanoribbons and analytical solutions", Science and Technology of Advanced Materials, vol. 11, 2010, pp. 1-18.
Educardo Costa Girão, et al., "Emergence of Atypical Properties in Assembled Graphene Nanoribbons", Physical Review Letters, vol. 107, 2011, pp. 135501-1-135501-5.
Xiaoyin Yang, et al., "Two-Dimensional Graphene Nanoribbons", Journal of the American Chemical Society, vol. 130, No. 13, XP055025794, 2008, pp. 4216-4217.
Yosuke Ishii, et al., "Facile bottom-up Synthesis of graphene nanofragments and nanoribbons by thermal polymerization of pentacenes", Nanoscale, vol. 4, 2012,6553-6561.
Matthias Georg Schwab, et al., "Structurally Defined Graphene Nanoribbons with High Lateral Extension", Journal of the American Chemical Society, vol. 134, 2012, pp. 18169-18172.
Jinming Cai, et al., "Atomically precise bottom-up fabrication of graphene nanoribbons", Nature, vol. 466, XP055022095, 2010, pp. 470-473.
Katsunori Wakabayashi, et al, "Edge effect on electronic transport properties of graphene nanoribbons and presence of perfectly conducting channel", Carbon, vol. 47, 2009, pp. 124-137.
Kyung Tae Kim, et al., "Synthesis of graphene nanoribbons with various widths and its application to thin-film transistor", Carbon, vol. 63, XP055126543, 2013, pp. 202-209.
Lukas Dössel, et al., "Graphene Nanoribbons by Chemists: Nanometer-Sized, Soluble and Defect-Free", Angewandte Chemie International Edition, vol. 50, XP055022100, 2011, pp. 2540-2543.
Marie Gille, et al., "Modular Synthesis of Monomers for On-Surface Polymerization to Graphene Architectures", Synlett, vol. 24, XP055126545, 2013, pp. 259-263.
Combined Office Action and Search Report dated Jun. 15, 2018 in Taiwanese Patent Application No. 104104481 (with English translation).
W. Jaskólski, et al., "Edge states and flat bands in graphene nanoribbons with arbitrary geometrics", Physical Review B, vol. 83, 2011, pp. P235424-1-P235424-9.
Katsunori Wakabayashi, et al., "Edge States and Flat Bands of Graphene Nanoribbons with Edge Modification", Journal of the Physical Society of Japan, vol. 79, No. 3, Mar. 2010, pp. P034706-1-P034706-7.
Tse-An Chen, et al., "Synthesis of Polyaromatic Hydrocarbons from Bis(biaryl)diynes: Large PAHs with Low Clar Sextets", Chemistry-A European Journal, vol. 17, 2011, pp. P8023-P8027.
Chinese Office Action dated Sep. 29, 2018, in Chinese Patent Application No. 201580007772.0 filed Feb. 9, 2015 (with English translation).
Office Action dated Jan. 29, 2019, in Japanese Patent Application No. 2016-552272, filed Feb. 9, 2015 (with English translation).

* cited by examiner

GRAPHENE NANORIBBONS WITH CONTROLLED ZIG-ZAG EDGE AND COVE EDGE CONFIGURATION

The present invention relates to graphene nanoribbons with controlled zig-zag edge and cove edge configuration and methods for preparing such graphene nanoribbons.

BACKGROUND OF THE INVENTION

Graphene, an atomically thin layer of graphite, is attracting considerable interest in material science since the recent discovery of its appealing electronic properties such as high charge carrier mobility, ambipolar switching capability and the quantum Hall effect. The conjunction with its chemical robustness and superior mechanical properties makes graphene an ideal candidate for a number of applications that require ultrathin but yet stable and highly conductive layers or large specific areas as for instance in energy storage applications.

One of the major limitations for using graphene in efficient digital switching applications is the absence of an electronic band gap. This obstacle can be overcome by structuring graphene down to the nanometer scale where quantum confinement induces band gaps that are characteristic for a given shape and size of the graphene nanostructure. The most prominent examples using quantum confinement for the opening of a band gap are carbon nanotubes (CNTs), where periodic boundary conditions along the circumference are responsible for the existence of both, metallic and semiconducting CNTs, as well as armchair graphene nanoribbons (AGNRs), where confinement to a very narrow strip of graphene induces sizable band gaps if the width/diameter is limited to a few nanometers.

For both, CNTs, and AGNRs, the structural boundary conditions conserve the symmetry between the two atomic sublattices A and B (see FIG. 5c for AGNR).

A much richer diversity of electronic properties is predicted for graphene nanostructures where the edges break the symmetry between the A and B sublattices. The most prominent example are zigzag graphene nanoribbons (ZGNRs) where the atoms forming the two opposite edges belong to complementary sublattices (FIG. 5a). Electronic structure simulations reveal related localized edge states, which are magnetically coupled to each other [Fujita, M., et al., Journal of the Physical Society of Japan 65, 1920-1923 (1996);]. In the case of ZGNRs, for instance, the localized states belonging to the two opposed edges couple antiferromagnetically to each other and thus allow for an efficient spatial separation of spin up and spin down electrons to the opposite respective edges.

Based on these edge-related spin-polarized properties, computational simulations have been used to explore a number of specific edge configurations. Among the most appealing predictions for ZGNRs are spin-polarized charge carrier injection into graphene, half-metallic charge carrier properties (metallic properties for one spin component and semiconducting properties for the other) as well as giant magnetoresistance.

Cove type GNRs (CGNR) can be described as a special case of ZGNR in which carbon atoms have been added, respectively removed from the perfect zigzag edge resulting in the characteristic cove type structure elements. As in the case of ZGNR, in CGNR the localized states belonging to the two opposed edges couple antiferromagnetically to each other and allow for an efficient spatial separation of spin up and spin down electrons to the opposite respective edges.

Armchair-type, zigzag-type or cove-type edges are shown in the following formulae:

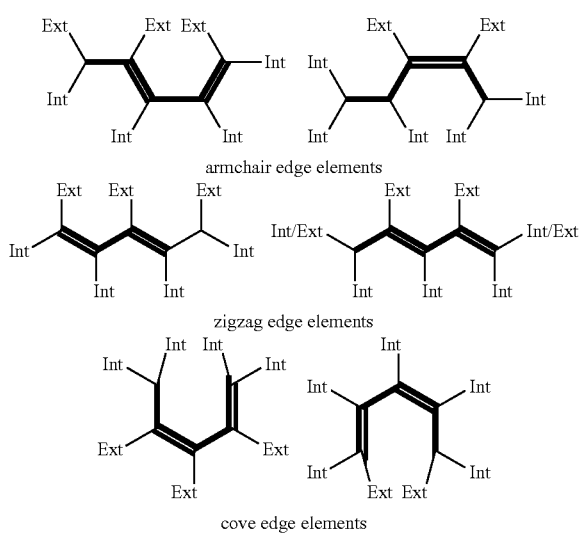

armchair edge elements zigzag edge elements cove edge elements wherein

Ext is an edge substituent and stands for a substituent that is not part of the conjugated aromatic GNR structure network, e.g. a hydrogen atom;

Int is an atom which is part of the conjugated aromatic GNR structure network, e.g. a $sp^2$ carbon atom). The positions of the double bonds are chosen arbitrarily since they together with the substituents Int form an extended conjugated system.

However, standard top-down fabrication techniques for the fabrication of GNR such as cutting graphene sheets e.g. using lithography, unzipping of carbon nanotubes (e.g. described in US 2010/0047154 and US2011/0097258), or using nanowires as a template are not suitable for ribbons narrower than 5-10 nm, because the edge configuration cannot be precisely controlled and they do not yield ribbons of monodisperse width. For high-efficiency electronic devices operating at ambient temperature, the ribbons need to be less than 10 nm wide, their width needs to be precisely controlled and, importantly, their edges need to be smooth because even minute deviations from the ideal edge shapes seriously degrade the electronic properties.

Due to the inherent limitations of lithographic methods and of other known approaches to fabricate graphene nanostructures, however, the experimental realization of GNRs with controlled zigzag and/or cove type edge structures in the hexagonal $sp^2$ carbon network with the required high precision has remained elusive. Bottom-up approaches based on cyclodehydrogenation reactions in solution (see e.g. WO 2012/149257, KR 101082335 B, WO 2013/061256) or on solid substrates (see e.g. WO 2012/145101, WO 2013/072292) have recently emerged as promising routes to the synthesis of nanoribbons and nanographenes with precisely controlled structures.

At least two general types of precisely controlled linear nanoribbon structures can be distinguished. In a first type, the edges are forming a straight line along the nanoribbon, while in another type, sometimes called 'chevron' type or 'nanowiggles' (described e.g. in Phys. Rev. Lett. 2011 (107), 135501 or in J. Am. Chem. Soc. 2012 (134), 18169), the edges are lying on a corrugated or saw-toothed line. The latter case can also be described as a periodic repetition of alternatingly aligned graphitic nanoribbon subunits seamlessly stitched together without structural defects.

The edges of the graphene nanoribbons may be terminated either with hydrogen atoms and/or with any other organic or inorganic groups.

For solution-based approaches using oligo phenylene precursors a polymer is typically prepared in a first step which is subsequently converted into the graphitic structure by Scholl-type oxidative cyclodehydrogenation. All of the reported solution based methods yield graphene nanoribbons with exclusively armchair type edge carbon atoms (with exception of both ends of the GNR) or armchair type edge carbon atoms and cove type edge carbon atoms (with exception of both ends of the GNR), whereby in the latter case the proportion of unambiguously assignable cove type edge carbon atoms is less than 20% of the sum of all edge carbon atoms.

The surface-confined bottom-up approach to controlled graphene nanoribbons as described in Nature 466, pp. 470-473 (2010), WO 2012/145101, and WO 2013/072292, typically results in armchair graphene nanoribbons. No graphene nanoribbons that do contain zigzag type edge carbon atoms and only graphene nanoribbons in which the proportion of unambiguously assignable cove type edge carbon atoms (with exception of both ends of the GNR) is less than 20% of the sum of all edge carbon atoms have been obtained.

It is an object of the present invention to provide a graphene nanoribbon (GNR) containing zig-zag type edge carbon atoms, cove type edge carbon atoms or a combination thereof in positions which are not at the end of the GNR, wherein the position of zigzag type edge carbon atoms and cove type edge carbon atoms and the distance between zigzag type edge carbon atoms and cove type edge carbon atoms as well as the ratio of zigzag type edge carbons to cove type edge carbons and to armchair carbons is precisely controlled. A further object of this invention is a process for preparing such a graphene nanoribbon.

SUMMARY OF THE INVENTION

One aspect of the present invention is a graphene nanoribbon comprising a repeating unit RU1 which comprises at least 20% of edge carbons which can unambiguously be assigned as zig-zag or cove type carbon atoms.

In the graphene nanoribbon of the present invention, the position of zigzag type edge carbon atoms and the distance between zigzag type edge carbon atoms as well as the number of zig-zag type edge carbon atoms per repeating unit can be precisely controlled.

In the graphene nanoribbon of the present invention, the position of armchair type edge carbon atoms and the distance between armchair type edge carbon atoms as well as the number of armchair type edge carbon atoms per repeating unit can be precisely controlled.

In the graphene nanoribbon of the present invention, the position of cove type edge carbon atoms and the distance between cove type edge carbon atoms as well as the number of cove type edge carbon atoms per repeating unit can be precisely controlled.

According to another aspect, the present invention provides a process for preparing the graphene nanoribbon as described above, which comprises:

(a) providing at least one aromatic monomer compound which is selected from at least one substituted or unsubstituted polycyclic aromatic monomer compound, at least one substituted or unsubstituted oligo phenylene aromatic monomer compound, or combinations thereof, on a solid substrate, (b) polymerization of the aromatic monomer compound so as to form at least one polymer on the surface of the solid substrate, (c) at least partially cyclodehydrogenating the one or more polymers of step (b).

According to a further aspect, the present invention provides compounds of formula A to C:

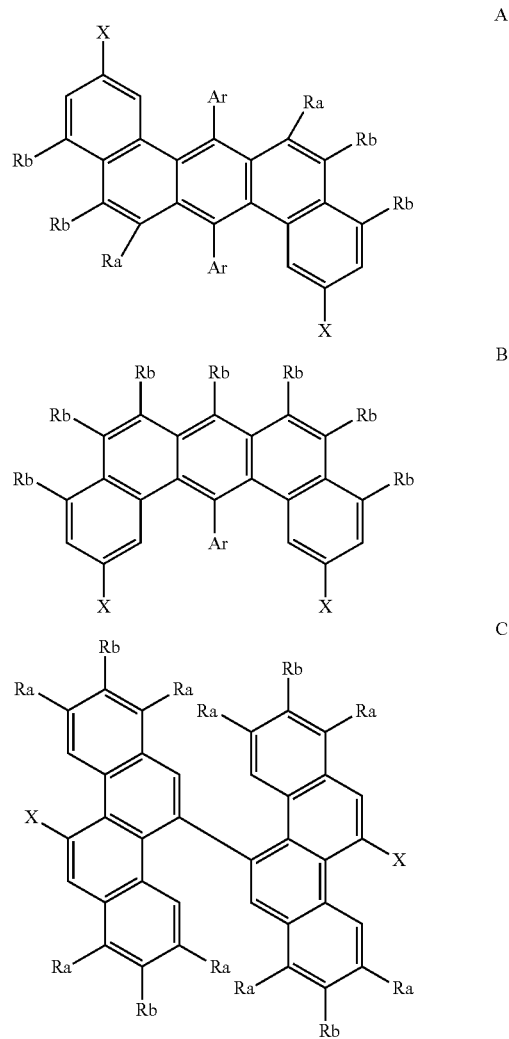

wherein

X independently from each other, are halogen or another leaving group, preferably Br or I, Ar independently of each other, are a substituted or unsubstituted aryl or heteroaryl, preferably a substituted or unsubstituted phenyl;

$R^a$ independently of each other, are hydrogen or linear or branched or cyclic $C_1$-$C_{30}$alkyl, preferably hydrogen or methyl;

$R^b$ independently of each other, are hydrogen; linear or branched or cyclic $C_1$-$C_{30}$ alkyl which is unsubstituted or substituted by one or more OH, $C_1$-$C_4$ alkoxy, phenyl, or by CN; $C_2$-$C_{12}$alkyl which is interrupted by one or more non-consecutive O; halogen; OH; $OR_3$; $SR_3$; CN; $NO_2$;

NR₁R₂; (CO)R₃; (CO)OR₃; O(CO)OR₃; O(CO)NR₁R₂; O(CO)R₃; $C_1$-$C_{12}$alkoxy; $C_1$-$C_{12}$alkylthio; ($C_1$-$C_6$alkyl)-NR₇R₈; or —O—($C_1$-$C_6$alkyl)NR₁R₂; aryl or heteroaryl (wherein aryl is preferably phenyl, biphenyl, naphthyl, or anthryl all of which are unsubstituted or are substituted by one or more $C_1$-$C_4$-alkyl, CN, OR₃, SR₃, CH₂OR₃, (CO)OR₃, (CO)NR₁R₂ or halogen);

or two $R^a$, together with the carbon atoms they are attached to, form a 5-8-membered cycle or heterocycle;

$R_1$ and $R_2$ independently of each other, are hydrogen, linear or branched $C_1$-$C_6$alkyl or phenyl, or $R_1$ and $R_2$ together with the nitrogen atom to which they are bonded form a group selected from

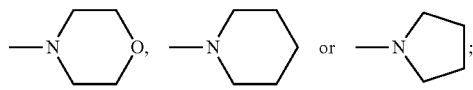

$R_3$ is selected from H, $C_1$-$C_{12}$ alkyl and phenyl, which may be unsubstituted or substituted by one or more $C_1$-$C_4$ alkyl, phenyl, halogen, $C_1$-$C_4$ alkoxy or $C_1$-$C_4$ alkylthio.

According to a further aspect, the present invention relates to the use of the aromatic monomer compounds as described above for preparing a graphene nanoribbon having a defined structure.

DETAILED DESCRIPTION OF THE INVENTION

According to the present invention the graphene nanoribbon comprises a repeating unit RU1. Such repeating unit RU1 comprises at least 20% of edge carbons which can unambiguously be assigned as zigzag type carbon atoms or unambiguously be assigned as cove type carbon atoms, or both.

For illustration the following formula shows an exemplary GNR structure which contains only armchair edges (with exception of both ends of the GNR). In this GNR, all carbon atoms at the edge (with exception of both ends of the GNR) can be assigned as armchair type carbon atoms:

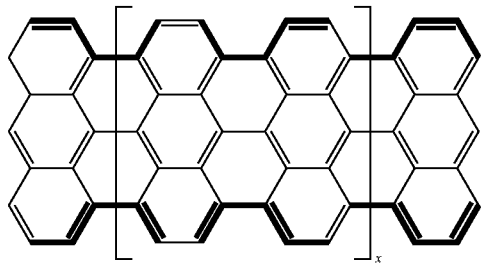

wherein x is an integer greater or equal to 1.

For illustration the following formula shows an exemplary GNR which contains only zigzag edges (with exception of both ends of the GNR). In this GNR, all carbon atoms at the edges (with exception of both ends of the GNR) can be assigned as zigzag type carbon atoms.

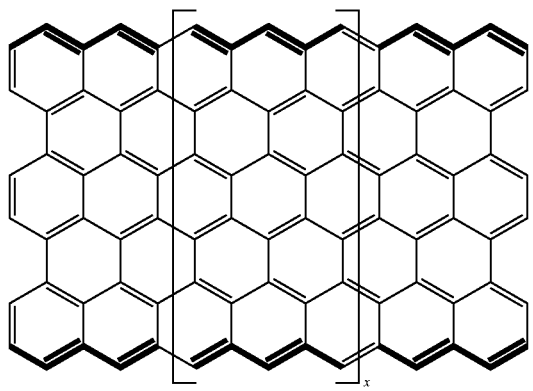

The following formula shows two illustrations of the same exemplary GNR which contains only cove edges (with exception of both ends of the GNR). In this GNR, all carbon atoms at the edges (with exception of both ends of the GNR) can be assigned as cove type carbon atoms:

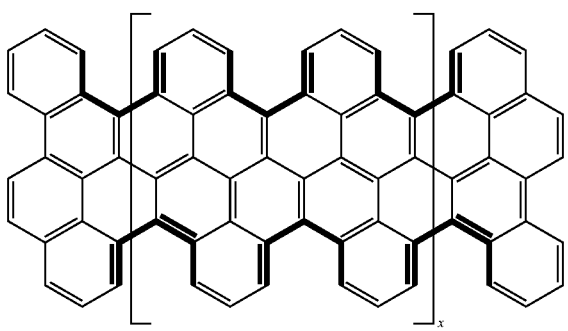

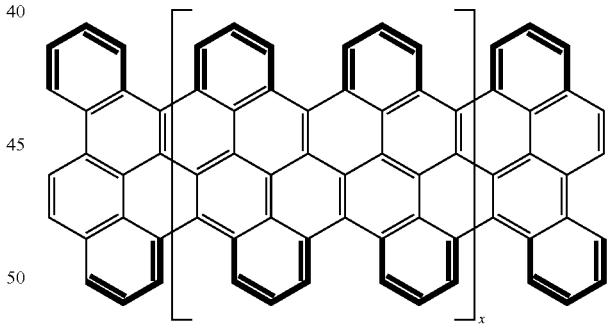

Some GNR structures do contain edge elements which cannot be assigned unambiguously as either armchair or zigzag ore cove type carbon atoms and some GNR structures do contain edge elements which can neither be assigned as armchair, zigzag, nor cove type (see following formulae for three illustrations of one and the same GNR structure, highlighting armchair type edge carbon atoms (top), cove type edge carbon atoms (middle), respectively the non-ambiguously assignable edge carbon atoms denoted Y (bottom) and the edge carbon atoms Z which can neither be assigned as armchair type or zigzag type, nor as cove type.

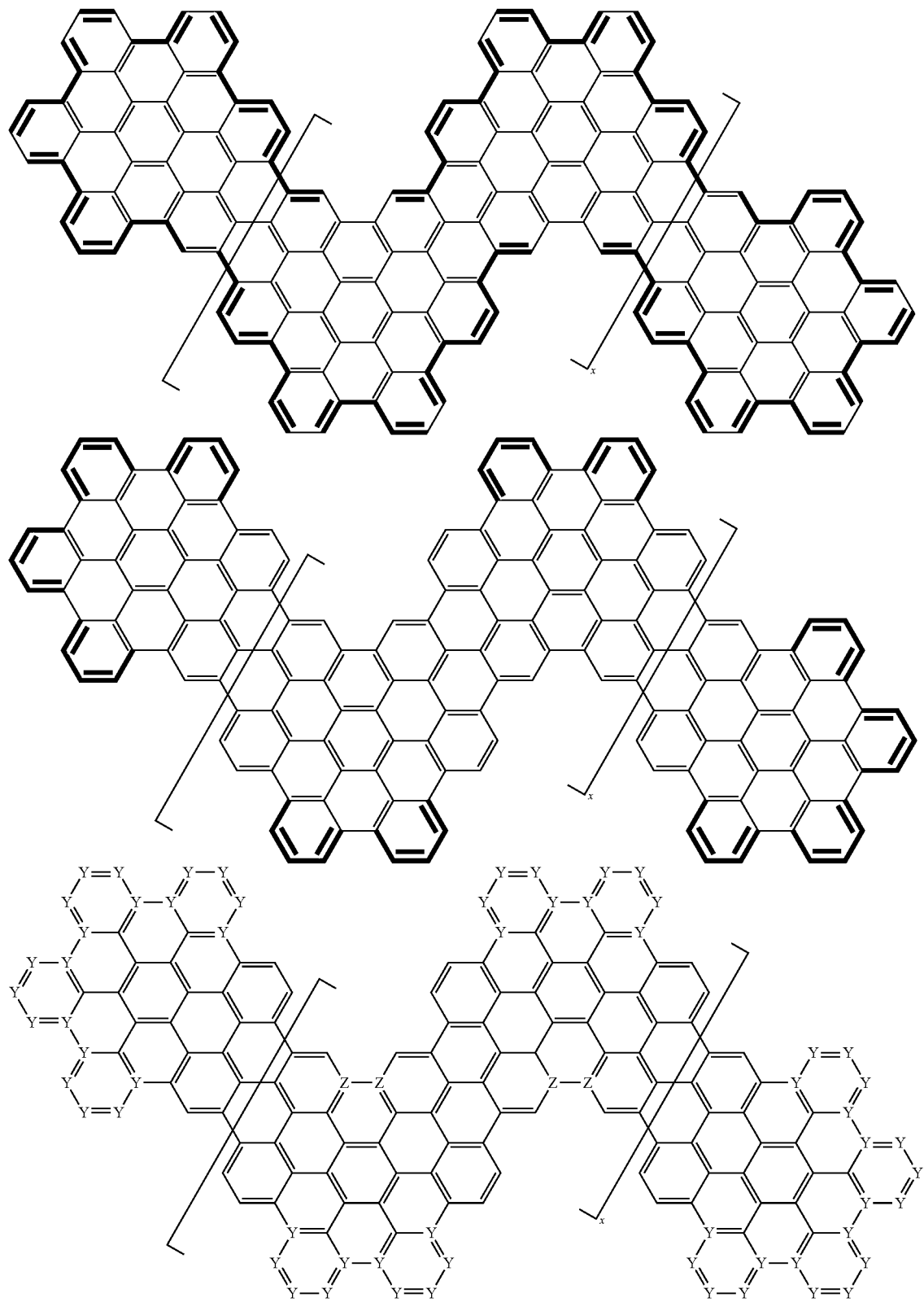
Similar to conventional polymers, the graphene nanoribbon of the present invention has its specific repeating unit. The term "repeating unit" relates to the part of the nanoribbon whose repetition would produce either the complete ribbon (except for the ends) or, if the GNR is made of two or more segments, one of these segments (except for the ends). The term "repeating unit" presupposes that there is at least one repetition of said unit. In other words, if the repeating unit is referred to as RU1, the GNR or one of its segments is made of n RU1 units with n≥2 (i.e. (RU1)$_n$ with n≥2). The upper limit depends on the desired final properties of the graphene nanoribbon and/or the process conditions, and can be, without limitation, e.g. n≤2500.

The graphene nanoribbon may comprise just one repeating unit RU1 (with n repetitions as indicated above). However, it is also possible that the graphene nanoribbon of the present invention comprises two or more different repeating units RU1, RU2, ... RUm, thereby resulting in a segmented graphene nanoribbon.

The graphene nanoribbon may be non-segmented. Alternatively, the graphene nanoribbon may be a segmented graphene nanoribbon which comprises at least two different graphene segments S1 and S2 covalently linked to each other, wherein the neighbouring segments S1 and S2 have different repeating units RU1 and RU2.

The repeating unit RU1 may comprise just one type of edge carbon atoms (e.g. only zigzag type edge carbon atoms or only cove type edge carbon atoms). Alternatively, the repeating unit may contain two or three types of edge carbon atoms (i.e. zigzag type carbon edge atoms and/or cove type carbon edge atoms and/or armchair type edge carbon atoms). In some cases a specific carbon edge atom cannot unambiguously be assigned as armchair type or zigzag type or cove type carbon atom because it is fulfilling the conditions for more than one type of edge carbon atoms. Such a carbon edge atom is for instance an armchair type edge atom and a cove type edge atom at the same time, i.e. a non-ambiguously assignable edge carbon atom.

The number of zigzag type edge carbon atoms within the graphene nanoribbon repeating unit RU1 may vary over a broad range, depending on the desired final properties of the GNR.

The number of cove type edge carbon atoms within the graphene nanoribbon repeating unit RU1 may vary over a broad range, depending on the desired final properties of the GNR.

The number of armchair type edge carbon atoms within the graphene nanoribbon repeating unit RU1 may vary over a broad range, depending on the desired final properties of the GNR.

On the other hand, as already indicated above, it may be preferred that the number of zig-zag type edge carbon atoms of the repeating unit is high. Preferably, the ratio of the number of zig-zag type and/or cove type edge carbon atoms to the number of all edge carbon atoms in the repeating unit RU1 is 0.2 or more, preferably 0.4 or more, most preferably 0.6 or more.

In a preferred embodiment, the graphene nanoribbon has exclusively zigzag type edge carbon atoms (with exception of both ends of the GNR).

In another preferred embodiment, the graphene nanoribbon has exclusively cove type edge carbon atoms (with exception of both ends of the GNR).

In another preferred embodiment, the graphene nanoribbon has exclusively zigzag type and cove type edge carbon atoms (with exception of both ends of the GNR).

GNR Precursor Monomers

As will be discussed below in further detail, the graphene nanoribbon containing zigzag type edge carbon atoms and/or cove type carbon atoms may preferably be obtained by polymerizing at least one substituted or unsubstituted polycyclic aromatic monomer compound and/or at least one substituted or unsubstituted oligo phenylene aromatic monomer compound, followed by partial or complete cyclodehydrogenation of the polymer. Substituted or unsubstituted polycyclic aromatic monomer compounds from which the repeating unit of the graphene nanoribbon can be derived include e.g. naphthalene, anthracene, tetracene, pentacene, hexacene, heptacene, octacene, nonacene, phenanthrene, bisanthene, trisanthene, chrysene, pyrene, triphenylene, benzo[a]pyrene, perylene, coronene, all of which can be substituted or unsubstituted or at least one of their aromatic carbon atoms can be substituted by a heteroatom. Substituted or unsubstituted oligo phenylene aromatic monomer compounds from which the repeating unit of the graphene nanoribbon can be derived include e.g. biphenyl, triphenyl, tetraphenyl, pentaphenyl, hexaphenyl, heptaphenyl, octaphenyl, all of which can be substituted or unsubstituted or at least one of their aromatic carbon atoms can be substituted by a heteroatom.

The graphene nanoribbon containing zigzag type edge carbon atoms and/or cove type carbon atoms may preferably be obtained by polymerizing at least one methyl substituted polycyclic aromatic monomer compound and/or at least one methyl substituted oligo phenylene aromatic monomer compound, followed by partial or complete cyclodehydrogenation of the polymer and partial or complete transformation of cove type edge elements into zigzag type edge elements by coupling of the methyl substituent to an adjacent aryl group. Methyl substituted polycyclic aromatic monomer compounds from which the repeating unit of the graphene nanoribbon can be derived include e.g. naphthalene, anthracene, tetracene, pentacene, hexacene, heptacene, octacene, nonacene, phenanthrene, bisanthene, trisanthene, chrysene, pyrene, triphenylene, benzo[a]pyrene, perylene, coronene, all of which can have additional substituents or at least one of their aromatic carbon atoms can be substituted by a heteroatom. Methyl substituted oligo phenylene aromatic monomer compounds from which the repeating unit of the graphene nanoribbon can be derived include e.g. biphenyl, triphenyl, tetraphenyl, pentaphenyl, hexaphenyl, heptaphenyl, octaphenyl, all of which can have additional substituents or at least one of their aromatic carbon atoms can be substituted by a heteroatom.

Preferably, the repeating unit RU1 of the graphene nanoribbon is derived from at least one aromatic monomer compound which is selected from at least one substituted or unsubstituted polycyclic aromatic monomer compound, at least one substituted or unsubstituted oligo phenylene aromatic monomer compound, or combinations thereof.

In another preferred embodiment, the repeating unit RU1 of the graphene nanoribbon is derived from at least one methyl substituted aromatic monomer compound which is selected from at least one methyl substituted aromatic monomer compound that optionally has additional substituents, at least one methyl substituted oligo phenylene aromatic monomer compound that optionally has additional substituents, or combinations thereof.

The monomers may preferably comprise a terminally phenyl annelated phenanthryl unit.

Preferably the aromatic monomer compound may have one of the following formulae A to C:

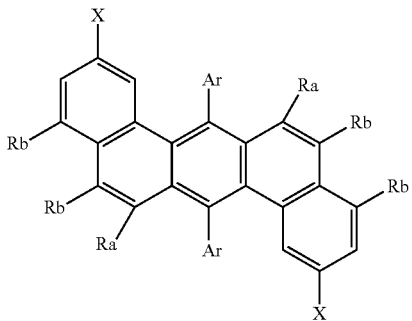

A

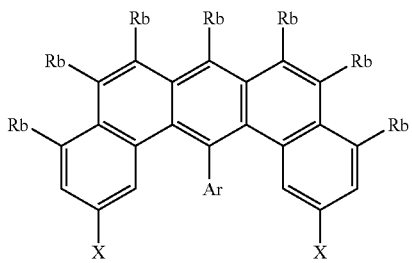

B

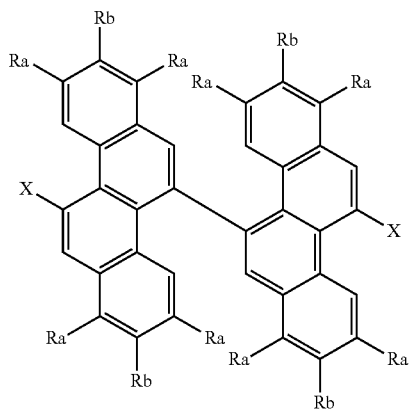

C wherein
X independently from each other, are halogen or another leaving group, preferably Br or I,
Ar independently of each other, are a substituted or unsubstituted aryl or heteroaryl, preferably a substituted or unsubstituted phenyl;
$R^a$ independently of each other, are hydrogen or linear or branched or cyclic $C_1$-$C_{30}$alkyl, preferably hydrogen or methyl;
$R^b$ independently of each other, are hydrogen; linear or branched or cyclic $C_1$-$C_{30}$ alkyl which is unsubstituted or substituted by one or more OH, $C_1$-$C_4$ alkoxy, phenyl, or by CN; $C_2$-$C_{12}$alkyl which is interrupted by one or more non-consecutive O; halogen; OH; $OR_3$; $SR_3$; CN; $NO_2$; $NR_1R_2$; $(CO)R_3$; $(CO)OR_3$; $O(CO)OR_3$; $O(CO)NR_1R_2$; $O(CO)R_3$; $C_1$-$C_{12}$alkoxy; $C_1$-$C_{12}$alkylthio; ($C_1$-$C_6$alkyl)-$NR_1R_2$; or —O—($C_1$-$C_6$alkyl)$NR_1R_2$; aryl or heteroaryl (wherein aryl is preferably phenyl, biphenyl, naphthyl, or anthryl all of which are unsubstituted or are substituted by one or more $C_1$-$C_4$-alkyl, CN, $OR_3$, $SR_3$, $CH_2OR_3$, (CO)$OR_3$, $(CO)NR_1R_2$ or halogen);
or
two $R^b$, together with the carbon atoms they are attached to, form a 5-8-membered cycle or heterocycle;
$R_1$ and $R_2$ independently of each other, are hydrogen, linear or branched $C_1$-$C_6$alkyl or phenyl, preferably hydrogen, $C_1$-$C_4$ alkyl or $R_1$ and $R_2$ together with the nitrogen atom to which they are attached to form a group selected from

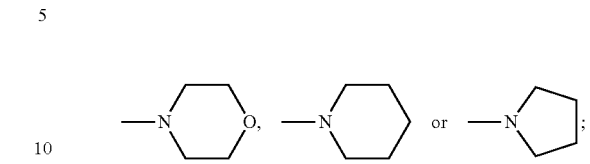

$R_3$ is selected from H, $C_1$-$C_{30}$alkyl and phenyl, which may be unsubstituted or substituted by one or more $C_1$-$C_4$ alkyl, phenyl, halogen, $C_1$-$C_4$ alkoxy or $C_1$-$C_4$ alkylthio preferably hydrogen, $C_1$-$C_{30}$alkyl.

By way of example, the aromatic monomer compound may have one of the following formulas I to X:

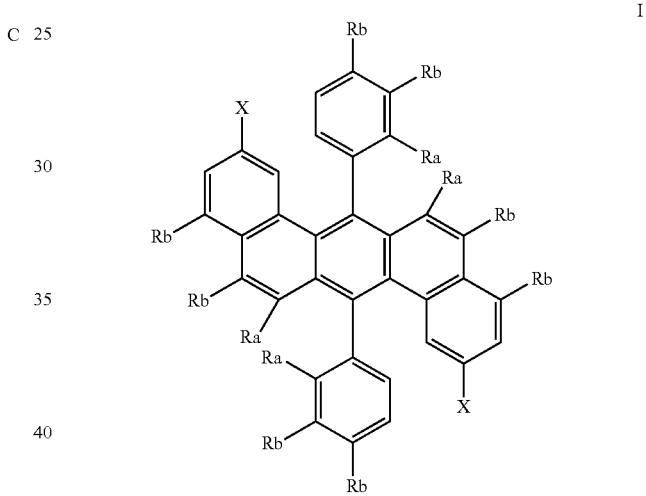

I

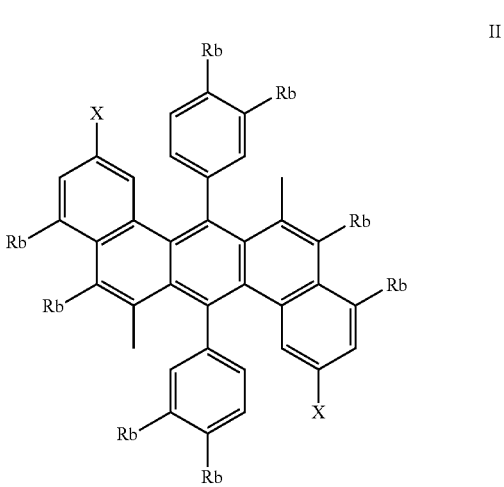

II

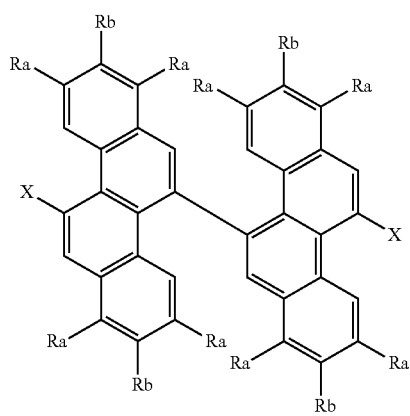
III
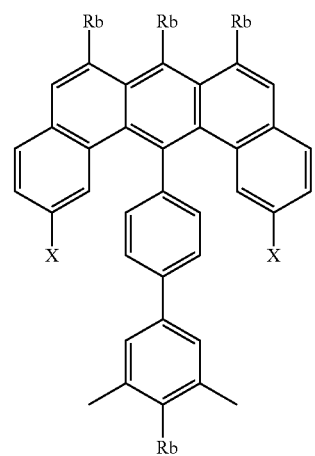
IV
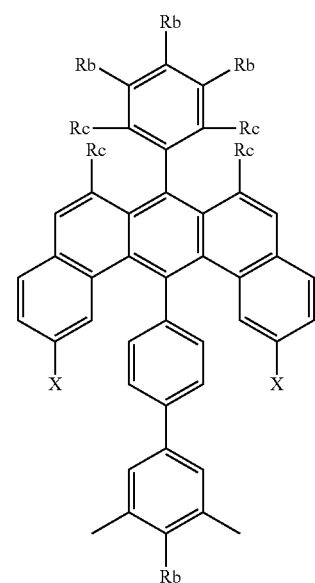
V
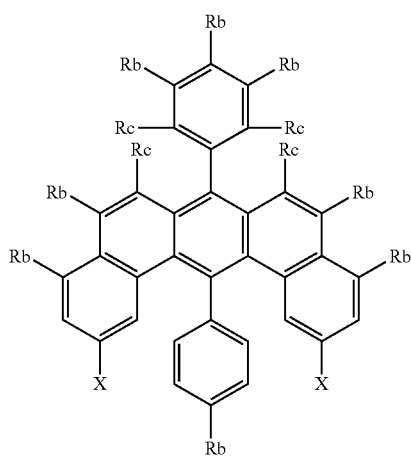
VI
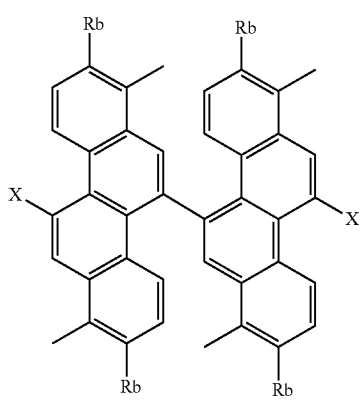
VII
VIII

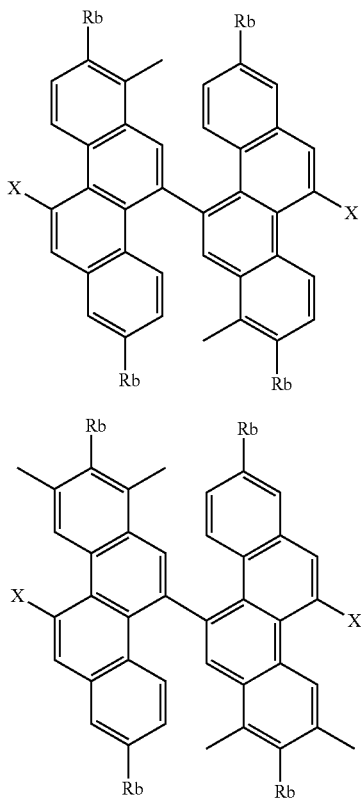

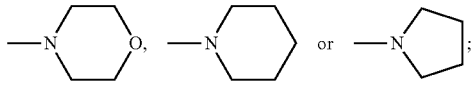

wherein

X independently from each other, are a leaving group;

$R^a$ independently of each other are hydrogen or linear or branched or cyclic $C_1$-$C_{30}$alkyl, preferably hydrogen or methyl;

$R^b$ independently of each other, are hydrogen; linear or branched or cyclic $C_1$-$C_{30}$alkyl which is unsubstituted or substituted by one or more OH, $C_1$-$C_4$alkoxy, phenyl, or by CN; $C_2$-$C_{12}$alkyl which is interrupted by one or more non-consecutive O; halogen; OH; $OR_3$; $SR_3$; CN; $NO_2$; $NR_1R_2$; $(CO)R_3$; $(CO)OR_3$; $O(CO)OR_3$; $O(CO)NR_1R_2$; $O(CO)R_3$; $C_1$-$C_{12}$alkoxy; $C_1$-$C_{12}$alkylthio; $(C_1$-$C_6$alkyl)-$NR_7R_8$; or —O—$(C_1$-$C_6$alkyl)$NR_1R_2$; aryl or heteroaryl (wherein aryl is preferably phenyl, biphenyl, naphthyl, or anthryl all of which are unsubstituted or are substituted by one or more $C_1$-$C_4$-alkyl, CN, $OR_3$, $SR_3$, $CH_2OR_3$, (CO)$OR_3$, (CO)$NR_1R_2$ or halogen), preferably hydrogen, linear or branched $C_1$-$C_{30}$alkyl, $OR_3$, $NR_1R_2$;

$R^c$ independently of each other, are hydrogen; linear or branched or cyclic $C_1$-$C_{30}$alkyl which is unsubstituted or substituted by one or more OH, $C_1$-$C_4$alkoxy, phenyl, or by CN; $C_2$-$C_{12}$alkyl which is interrupted by one or more non-consecutive O; halogen; OH; $OR_3$; $SR_3$; CN; $NO_2$; $NR_1R_2$; $(CO)R_3$; $(CO)OR_3$; $O(CO)OR_3$; $O(CO)NR_1R_2$; $O(CO)R_3$; $C_1$-$C_{12}$alkoxy; $C_1$-$C_{12}$alkylthio; $(C_1$-$C_6$alkyl)-$NR_7R_8$; or —O—$(C_1$-$C_6$alkyl)$NR_1R_2$; $R^c$ preferably is hydrogen or alkyl.

Alternatively, two groups $R^a$, $R^b$ and $R^c$, may together with the carbon atoms they are attached to, form a 5-8-membered cycle or heterocycle;

$R_1$ and $R_2$ are, independently of each other, hydrogen, linear or branched $C_1$-$C_6$alkyl or phenyl, preferably hydrogen, $C_1$-$C_4$alkyl or $R_1$ and $R_2$ together with the nitrogen atom to which they are bonded form a group selected from

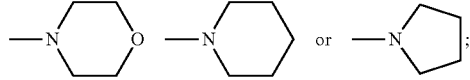

$R_3$ is selected from H, $C_1$-$C_{30}$alkyl and phenyl, which may be unsubstituted or substituted by one or more $C_1$-$C_4$ alkyl, phenyl, halogen, $C_1$-$C_4$ alkoxy or $C_1$-$C_4$ alkylthio, preferably H, $C_1$-$C_{30}$alkyl.

Typical leaving groups X are selected from halogen, sulfonate, phosphonate, boronate, azo, silane, stannane, without being restricted thereto. Preferable leaving groups are selected from Br and I.

The average width of the graphene nanoribbon can be varied over a broad range, depending on the desired final properties.

Preferably, the graphene nanoribbon or a segment of the graphene nanoribbon made of the repeating unit RU1 has a width of 20 nm or less, more preferably 15 nm or less, even more preferably 10 nm or less, even more preferably 7 nm or less, most preferably 4 nm or less.

The GNR width and type of edge carbon structure is determined with scanning tunneling microscopy (STM). The apparent width is corrected for the finite tip radius by STM simulation as explained in WO 2013/072292.

According to conventional notion, the width of a graphene nanoribbon may be expressed by the number N of dimer lines across the width (K. Wakabayashi et al., Sci. Technol. Adv. Mater. 11 (2010) 054504). The determination of N for the zig-zag, cove and armchair type GNRs, respectively, is shown in FIG. 5. Preferably, the repeating unit RU1 of the graphene nanoribbon may have a number N of dimer lines across the width of from 3 to 38, more preferably of from 3 to 21, or of from 5 to 20.

If the graphene nanoribbon comprises further repeating units RU2, RU3, . . . , the preferred width values indicated above apply to these additional repeating units as well.

In a particular embodiment of the graphene nanoribbon

X independently from each other, are selected from halogen, sulfonate, phosphonate, boronate, azo, silane, stannane;

$R^a$ independently of each other are hydrogen or linear or branched or cyclic $C_1$-$C_{10}$ alkyl;

$R^b$ is selected from hydrogen, linear or branched $C_1$-$C_{30}$ alkyl, $OR_3$, and $NR_1R_2$;

$R^c$ independently of each other, are hydrogen or $C_1$-$C_{30}$ alkyl.

In another particular embodiment of the graphene nanoribbon

X independently from each other, are selected from Br or I;

$R^a$ independently of each other are hydrogen or methyl;

$R^b$ is selected from hydrogen, linear or branched $C_1$-$C_{30}$ alkyl, $OR_3$, and $NR_1R_2$;

$R^c$ independently of each other, are hydrogen or $C_1$-$C_{10}$ alkyl;

$R_1$ and $R_2$ are, independently of each other, hydrogen or $C_1$-$C_4$ alkyl or $R_1$ and $R_2$ together with the nitrogen atom to which they are bonded form a group selected from $R_3$ is selected from hydrogen and $C_1$-$C_{30}$ alkyl.

The graphene nanoribbons may preferably be prepared from the monomers of the following formulae 1-12:
1
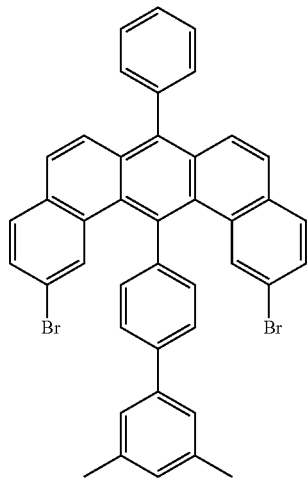
2
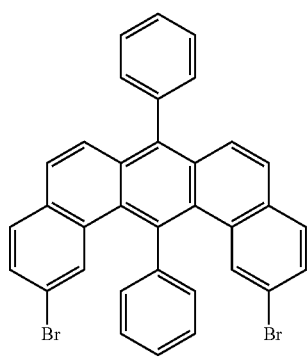
3
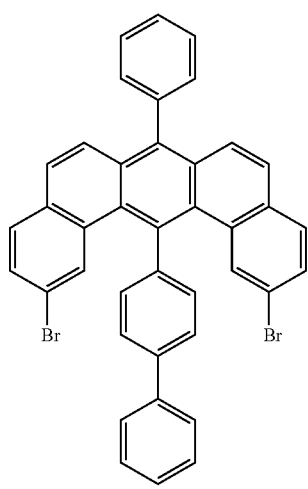
4
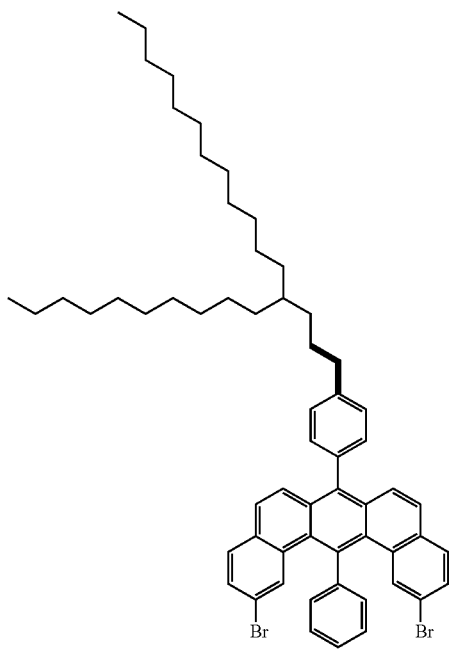
5
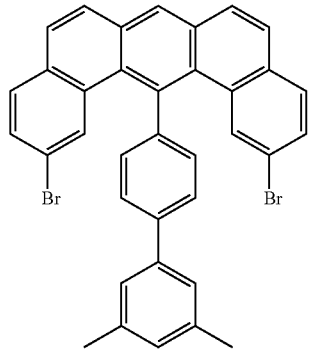
6
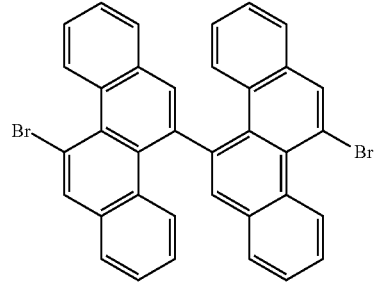

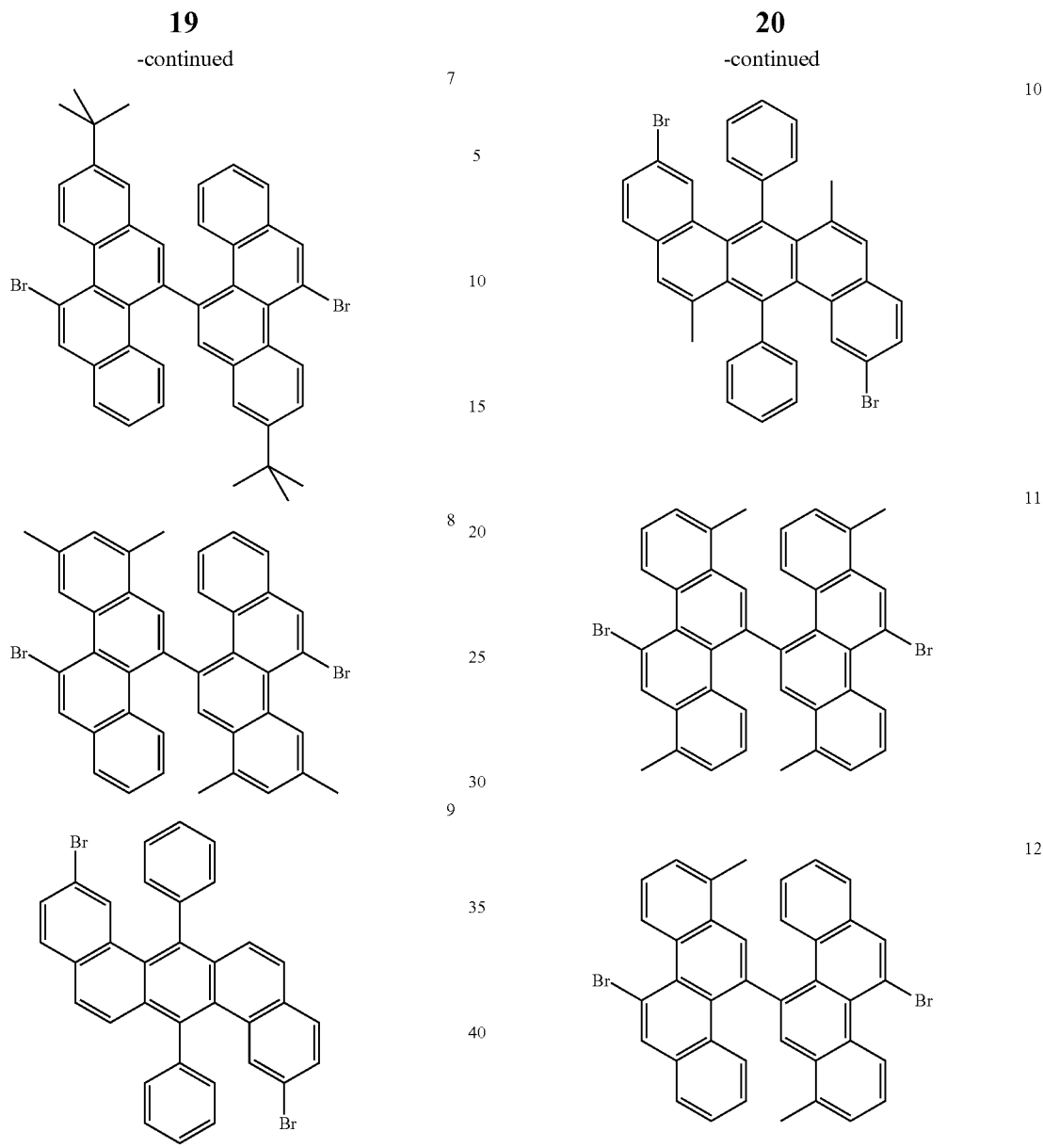

TABLE 1

Overview of preferred Monomer Structures

| Monomer Structure (compound No.) | GNR Structure | edge carbons per repeating unit | zigzag edges per repeating unit (unambiguous/ ambiguous) | cove edges per repeating unit (unambiguous/ ambiguous) | armchair edges per repeating unit (unambiguous/ ambiguous) | unambiguous/ ambiguous edges per repeating unit |
|---|---|---|---|---|---|---|
| I (9) | i | 24 | 10 (4/6) 41.7% (16.7%/25%) | 16 (10/6) 66.7% (41.7%/25%) | 10 (0/10) 41.7% (0%/41.7%) | 14/10 |
| II (10) | ii | 20 | 18 (10/8) 90% (50%/40%) | 0 | 10 (2/8) 50% (10%/40%) | 12/8 |
| III (6, 7) | iii | 24 | 0 | 24 (24/0) 100% (100%/0%) | 0 | 24/0 |

TABLE 1-continued

Overview of preferred Monomer Structures

| Monomer Structure (compound No.) | GNR Structure | edge carbons per repeating unit | zigzag edges per repeating unit (unambiguous/ambiguous) | cove edges per repeating unit (unambiguous/ambiguous) | armchair edges per repeating unit (unambiguous/ambiguous) | unambiguous/ambiguous edges per repeating unit |
|---|---|---|---|---|---|---|
| IV (5) | iv | 24 | 24 (24/0) 100% (100%/0%) | 0 | 0 | 24/0 |
| V (1) | v | 24 | 24 (24/0) 100% (100%/0%) | 0 | 0 | 24/0 |
| VI (2, 4) | vi | 32 | 26 (26/0) 81.3% (81.3%/0%) | 0 | 0 | 26/8 not assignable |
| VII (3) | vii | 32 | 14 (10/4) 43.8% (31.3%/12.5%) | 22 (18/4) 68.8% (56.3%/12.5%) | 0 | 28/4 |
| VIII (11) | viii | 16 | 16 (16/0) 100% (100%/0%) | 0 | 0 | 16/0 |
| IX (12) | ix | 20 | 14 (10/4) 70% (50%/20%) | 10 (6/4) 50% (30%/20%) | 0 | 16/4 |
| X (8) | viii | 16 | 16 (16/0) 100% (100%/0%) | 0 | 0 | 16/0 |

GNR Formation

The present invention provides a process for preparing the graphene nanoribbon as disclosed above, which comprises:
(a) providing at least one polycyclic aromatic monomer compound and/or oligo phenylene aromatic monomer compound on a solid substrate,
(b) polymerization of the polycyclic aromatic and/or oligo phenylene aromatic monomer compound so as to form at least one polymer, on the surface of the solid substrate,
(c) at least partially cyclodehydrogenating the one or more polymers of step (b).

The polycyclic aromatic monomer compound and/or the oligo phenylene aromatic monomer compound of step (a) may be any monomer described herein.

As indicated above, step (a) includes providing the at least one polycyclic aromatic monomer or oligo phenylene aromatic monomer compound on a solid substrate.

In another embodiment at least one of steps (a), (b) and (c) of the process is not processed on the solid substrate, but in solution. Preferably all steps (a), (b) and (c) are processed not on the solid substrate, but in solution.

Substrate

Any solid substrate enabling the deposition of the polycyclic aromatic monomer or oligo phenylene aromatic monomer compound and subsequent polymerization on its surface may be used. Preferably, the solid substrate has a flat surface.

The solid substrate on which the monomer compound is deposited may have a metal surface such as for example a Au, Ag, Cu, Al, W, Ni, Pt, or a Pd surface (which may e.g. be reconstructed or vicinal). The surface can be completely flat or patterned or stepped. Such patterned or stepped surfaces and manufacturing methods thereof are known to the skilled person. On patterned surfaces the growth of graphene nanoribbons may be directed by the surface pattern.

The solid substrate may also have a metal oxide surface such as silicon oxide, silicon oxynitride, hafnium silicate, nitrided hafnium silicates (HfSiON), zirconium silicate, hafnium (di)oxide and zirconium dioxide, or aluminium oxide, copper oxide, iron oxide.

The surface may also be made of a semiconducting material such as silicon, germanium, gallium arsenide, silicon carbide, and molybdenum disulfide.

The surface may also be a material such as boron nitride, sodium chloride, or calcite.

The surface may be electrically conducting, semiconducting, or insulating. The surface may be non-magnetic or magnetic (ferro- or anti-ferromagnetic).

Deposition

The deposition on the surface may be done by any process suitable for providing organic compounds on a surface. The process may e.g. be a vacuum deposition (sublimation) process, a solution based process such as spin coating, spray coating, dip coating, printing, electrospray deposition, or a laser induced desorption or transfer process. The deposition process may also be a direct surface to surface transfer.

Preferably the deposition is done by a vacuum deposition process. Preferably it is a vacuum sublimation process. The vacuum may be in the range of $10^{-1}$ to $10^{-11}$ mbar.

Polymerization

As indicated above, step (b) of the process of the present invention includes polymerization of the polycyclic aromatic monomer and/or oligo phenylene aromatic monomer compound so as to form at least one polymer (herein also referred to as "GNR precursor polymer") on the surface of the solid substrate.

Appropriate conditions for effecting polymerization of the polycyclic aromatic monomer and/or oligo phenylene aromatic monomer compound are generally known to the skilled person.

Preferably, the polymerization in step (b) is induced by thermal activation. However, any other energy input which induces polymerization of the polycyclic aromatic monomer and/or oligo phenylene aromatic monomer compound such as radiation can be used as well.

The activation temperature is dependent on the employed surface and the monomer and can be in the range of from 0 to 500° C.

Optionally, step (a) and/or step (b) can be repeated at least once before carrying out partial or complete cyclodehydrogenation in step (c). When repeating steps (a) and (b), the same monomer compound or a different polycyclic aromatic monomer and/or oligo phenylene aromatic monomer compound can be used.

Cyclodehydrogenation

As indicated above, step (c) of the process of the present invention includes at least partially cyclodehydrogenating the one or more GNR precursor polymers of step (b).

In general, appropriate reaction conditions for cyclodehydrogenation are known to the skilled person.

In a preferred embodiment, the polymer of step (b) is subjected to complete cyclodehydrogenation.

In one embodiment, at least two different polycyclic aromatic monomer or oligo phenylene aromatic monomer compounds are provided on the solid substrate in step (a).

According to this embodiment, two or more different monomer compounds, preferably having similar reactivity, are provided on the surface of the solid substrate, followed by inducing polymerization to form a co-polymer. Subsequently, a partial or complete cyclodehydrogenation reaction is carried out leading to a segmented graphene nanoribbon.

In a variation of this embodiment, a first polycyclic aromatic monomer or oligo phenylene aromatic monomer compound is deposited on the surface of the solid substrate, followed by inducing polymerization to form a polymer. A second monomer is then deposited on the same substrate surface, followed by inducing polymerization to form a block co-polymer. This step may optionally be repeated several times, either with identical or different monomer compounds to yield a multi block copolymer. Subsequently, the block co-polymer is subjected to a partial or complete cyclodehydrogenation reaction leading to a segmented graphene nanoribbon.

In another embodiment, the partial or complete cyclodehydrogenation reaction is induced by a spatially controlled external stimulus.

The external stimulus may be an electrical current, heat, an ion beam, oxidative plasma, microwave, light or electromagnetic radiation in general or it may be an oxidative chemical reagent. The spatial control of the activation may be done using a highly focused activation stimulus whose position versus the substrate can be controlled. The spatially confined activation stimulus may originate from a nano sized electrode, such as e.g. a tip of a tunneling microscope or from highly focused electromagnetic radiation such as e.g. a focused laser beam, or from a highly focused electron beam such as in an electron microscope. The spatial control of the activation may also be done using a nanostructured mask to direct the impact of the activation stimulus, such as e.g. a photo mask.

In a particular embodiment a further step (d) may be performed comprising at least partially coupling the methyl substituent of a cove type edge element of the one or more polymers of step (b) to an adjacent aryl group. In this way a cove type edge element is converted into a zig-zag type edge element. By way of example, such coupling is shown in the conversion of monomer VIII to structure viii. This coupling step is also further illustrated in the examples.

Depending on the conditions applied and the monomers used such coupling step (d) may be performed before, after or along with step (c).

The graphene nanoribbon (GNR) may also be prepared via a solution based process, as already mentioned above and generally known to those skilled in the art. The process preferably comprises a solution polymerization of the at least one polycyclic aromatic monomer compound and/or oligo phenylene aromatic monomer compound to an oligophenylene precursor polymer which can then be transformed into graphene nanoribbon using a solution based process such as cyclodehydrogenation (e.g. Scholl-type oxidative cyclodehydrogenation). The polymerization and cyclodehydrogenization process is preferably done with monomers comprising long alkyl or alkoxy chain substituents, e.g. in position $R_b$ of monomers defined above, in order to improve the solubility of the resulting GNR.

Graphene nanoribbon structures i-ix, which are non limiting examples that are thus formed from monomers I-X are shown by the following structures, wherein $R^b$ and $R^c$ have the same meaning as for monomers I to X above, X is selected from a leaving group, H and a free radical, and n is an integer of from 2 to 2500, preferably 4 to 1000, most preferably 5 to 500.

Graphene nanoribbon structure i contains cove type edges and zigzag type edges in the repeating unit RU1.

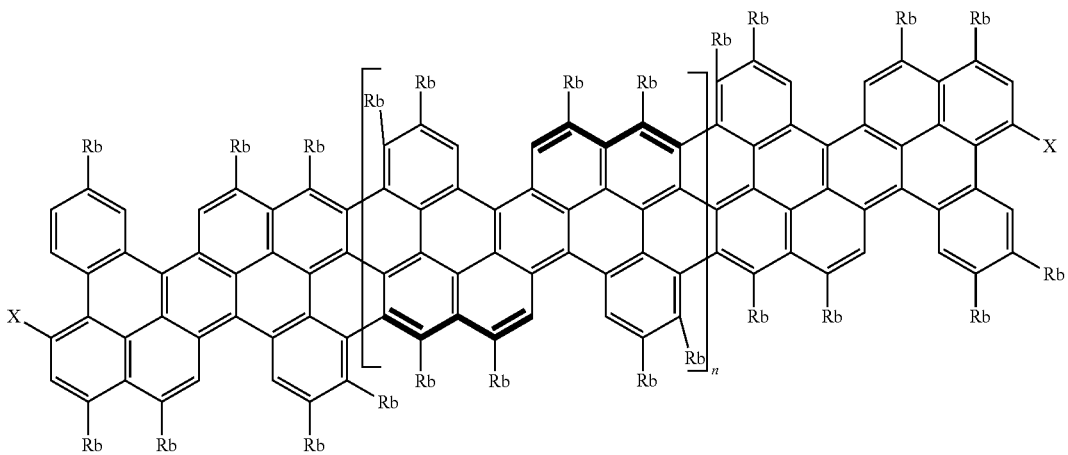

i (zigzag type edges)

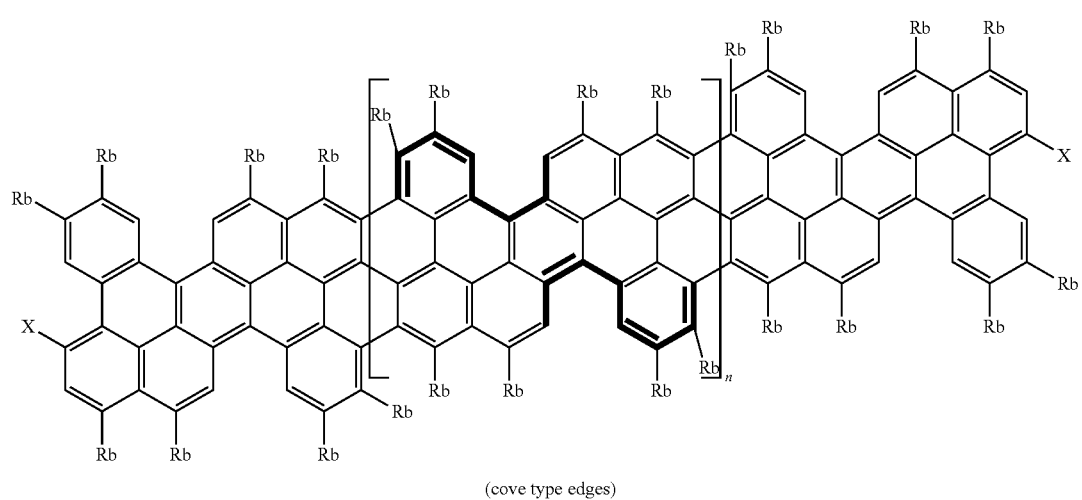
(cove type edges)
Graphene nanoribbon structure ii contains zigzag type edges and armchair type edges in the repeating unit RU1.
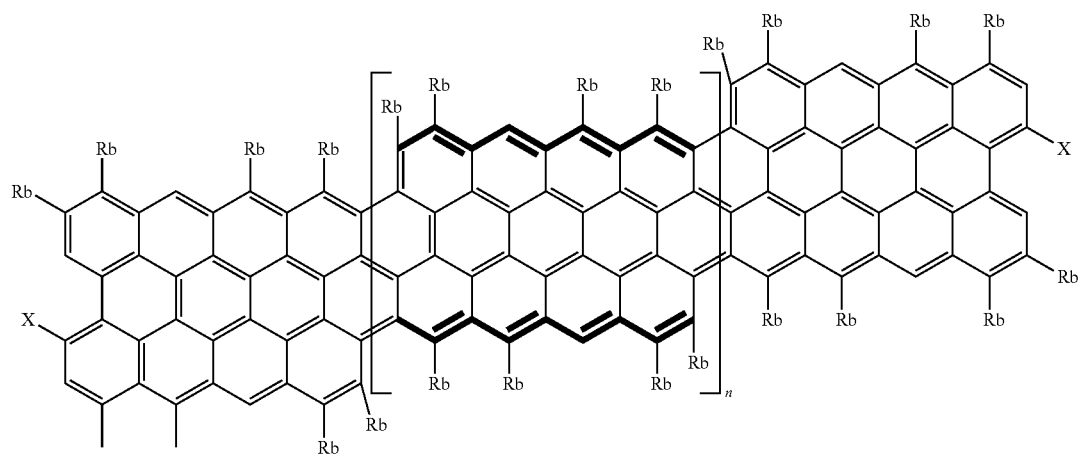
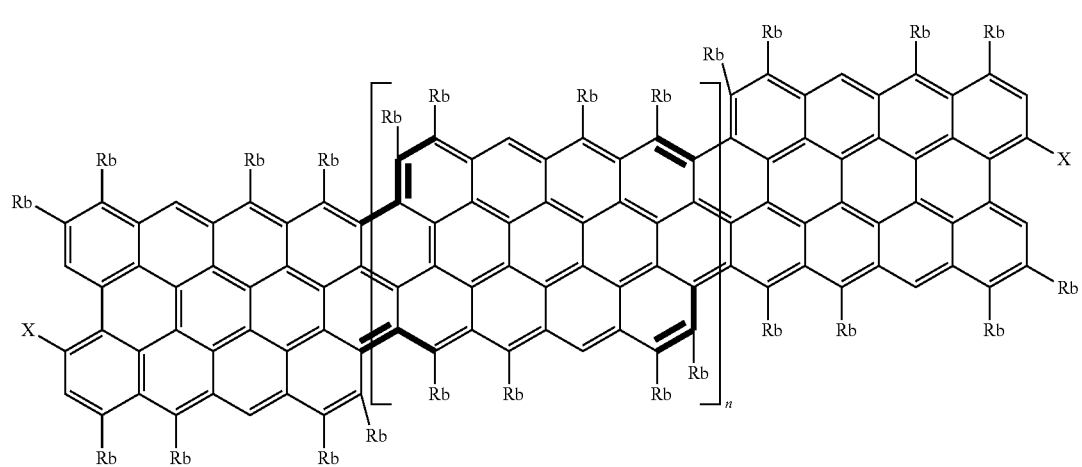
(armchair type edges)

Graphene nanoribbon structure iii contains exclusively cove type edges in the repeating unit RU1.
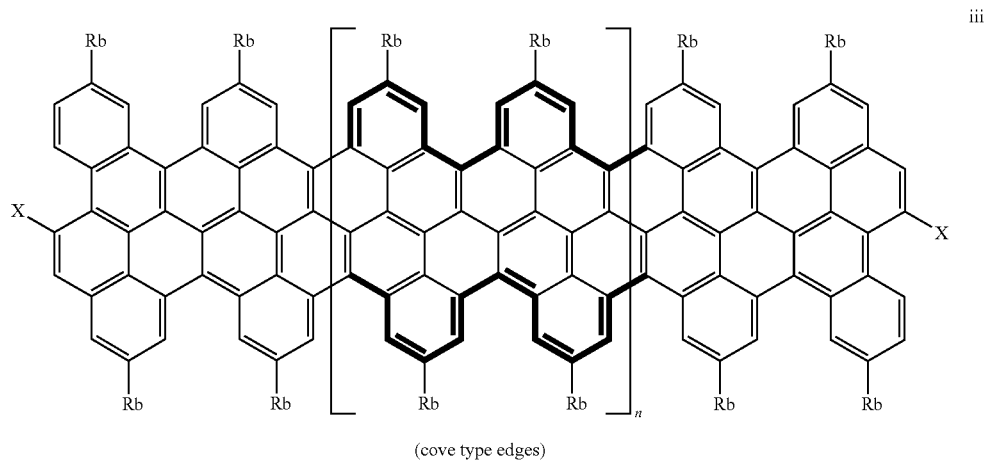
(cove type edges)
Graphene nanoribbon structure iv contains exclusively zigzag type edges in the repeating unit RU1.
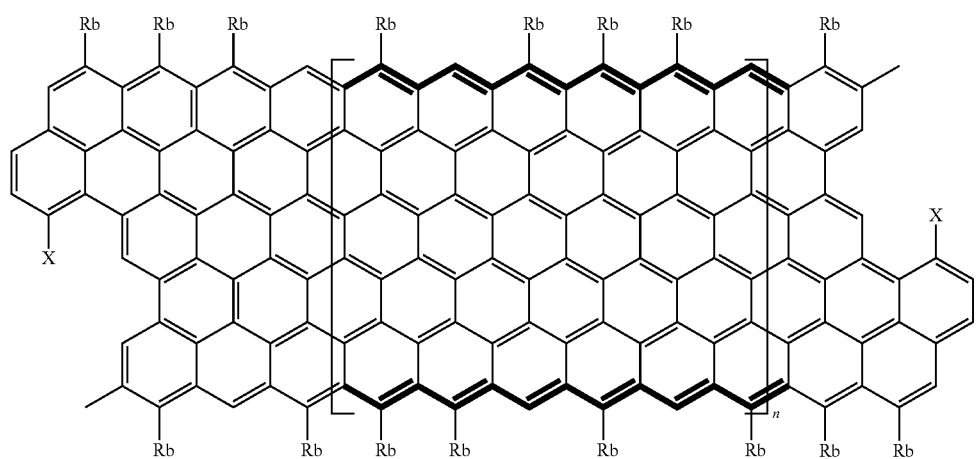
Graphene nanoribbon structure v contains exclusively zigzag type edges in the repeating unit RU1.

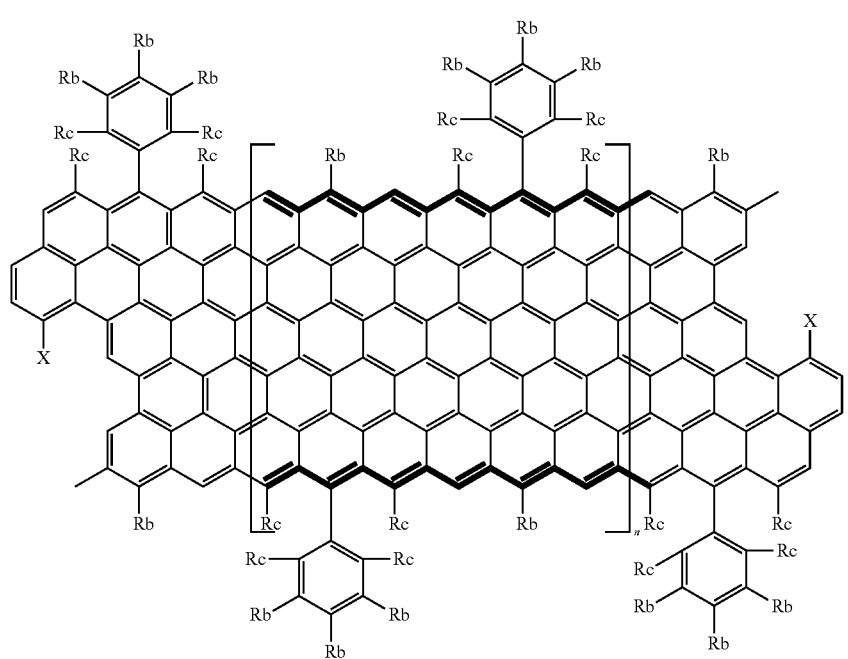
(zigzag type edges)
Graphene nanoribbon structure vi contains zigzag type edges and edges which can neither be assigned as zigzag, armchair, nor cove type edges in the repeating unit RU1.
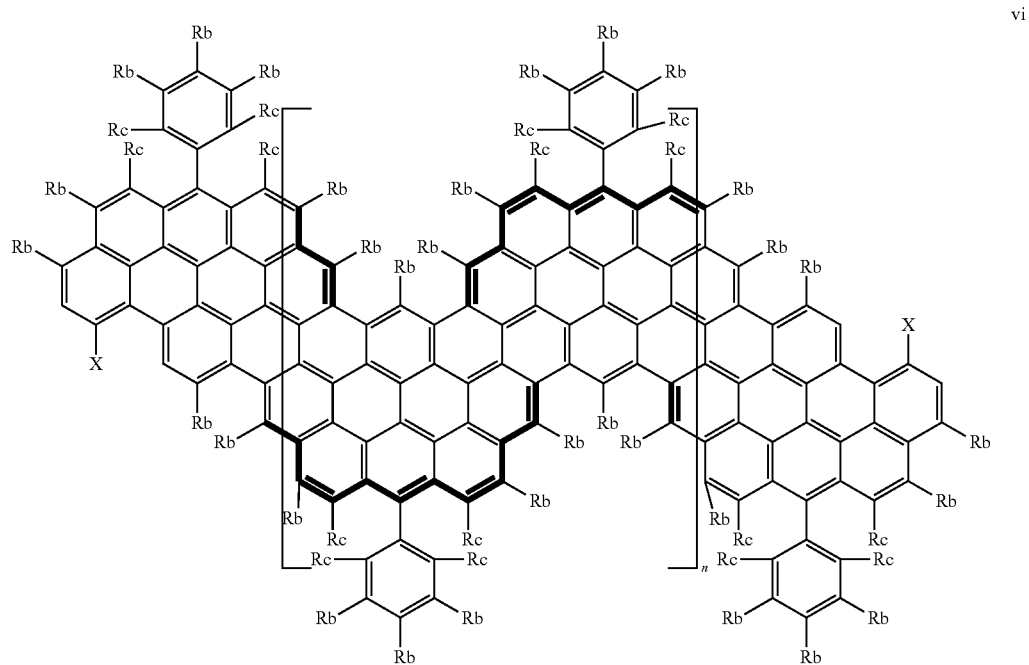
(zigzag type edges)

Graphene nanoribbon structure vii contains cove type edges and zigzag type edges in the repeating unit RU1.
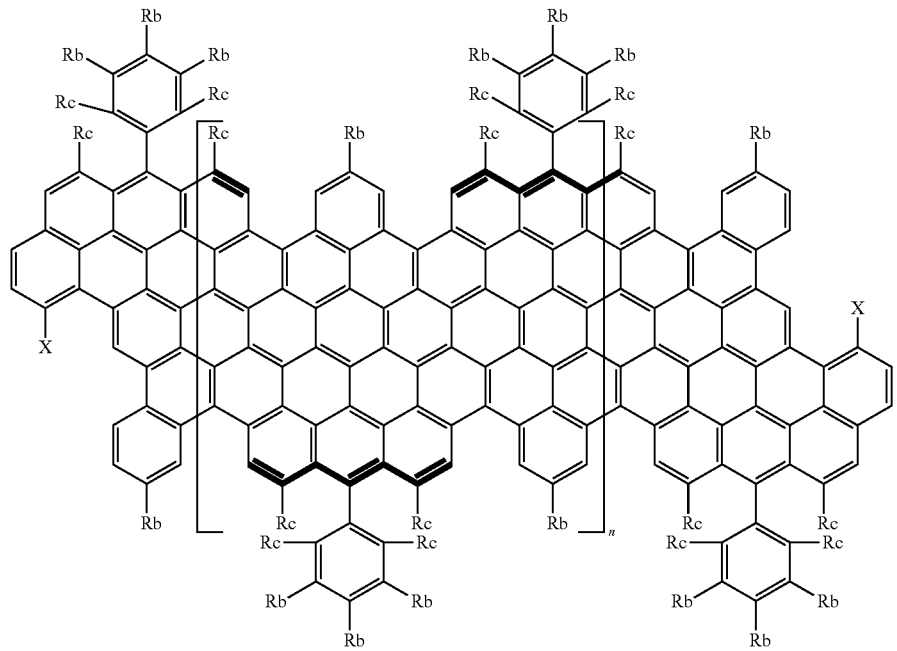
(zigzag type edges)
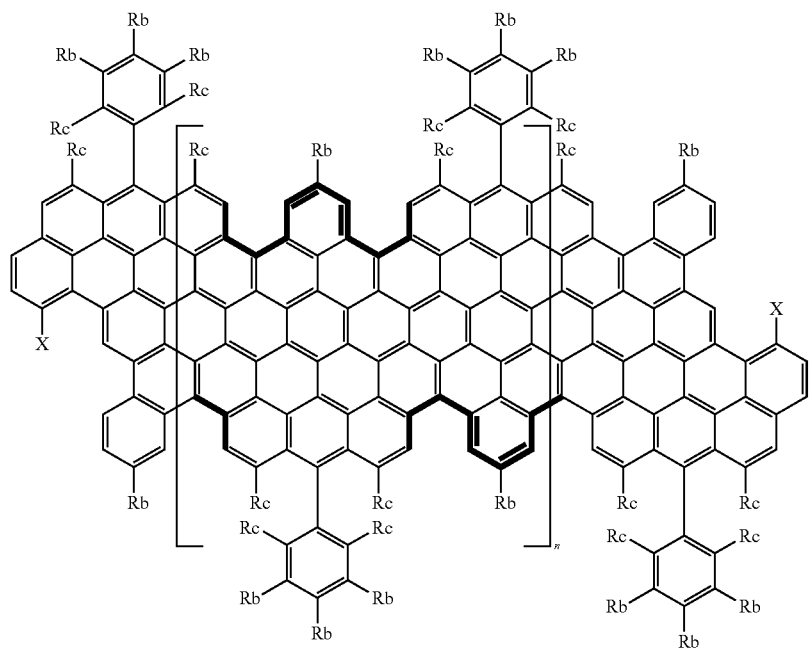
(cove type edges)
Graphene nanoribbon structure viii is derived of monomer VIII or X and contains exclusively zigzag type edges in the repeating unit RU1.

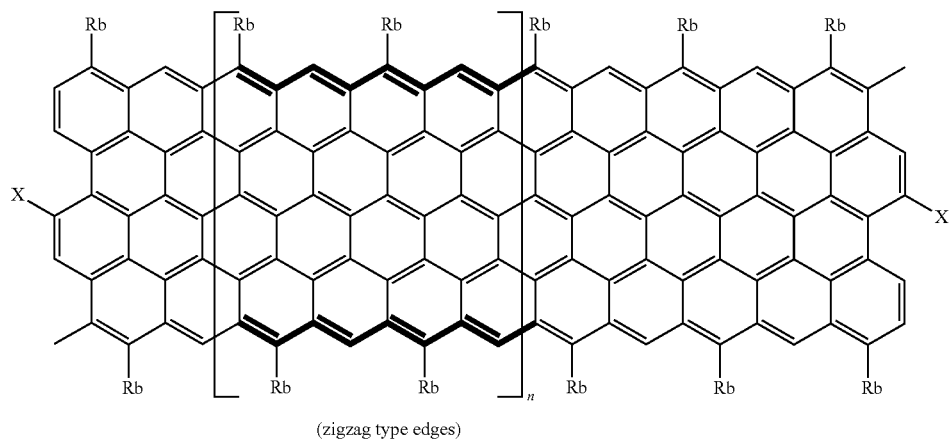
(zigzag type edges)

Graphene nanoribbon structure ix is derived of monomer IX and contains zigzag type edges and cove type edges in the repeating unit RU1.

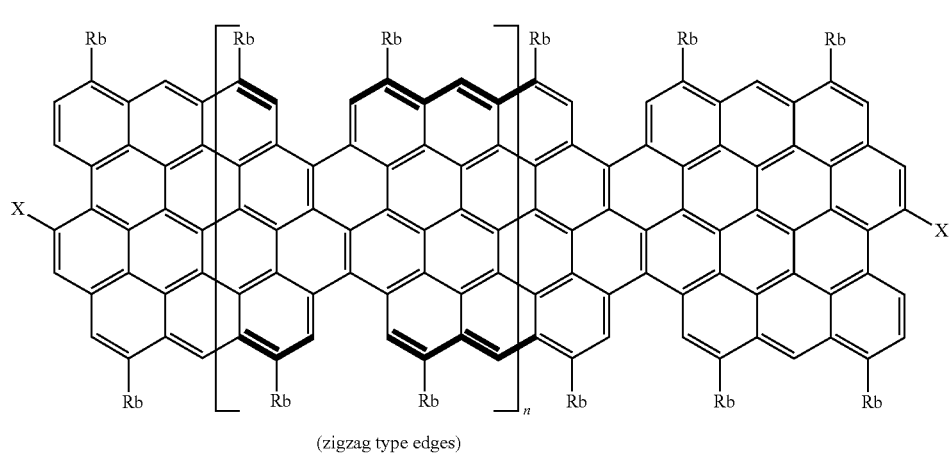
(zigzag type edges)

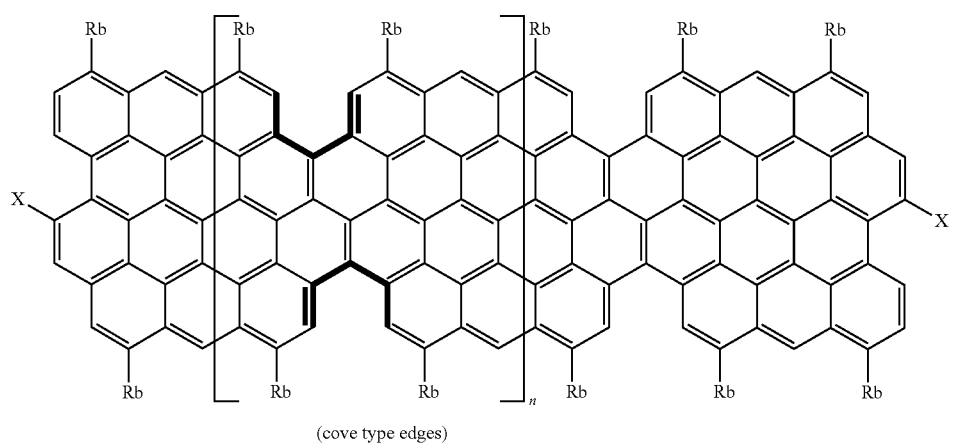
(cove type edges)

In particular embodiments aromatic groups in the GNR structures above or substituents $R^b$ and/or $R^c$ may react with other groups so as to form a 5 membered carbocyclic ring.

Therefore, if in the GNR precursor polymer two neighboring groups $R^c$ are hydrogen, the two carbon atoms substituted with hydrogen may form a 5-membered carbocyclic ring by cycloannelation (see e.g. in GNR structure vii), or, if in the GNR precursor polymer one of two direct neighboring groups $R^b$ is an alpha-hydrogen substituted aryl, preferably phenyl, and the other is hydrogen, the two carbon atoms substituted with hydrogen may form a 5-membered carbocyclic ring by cycloannelation (see e.g. in GNR structure iv), or if in the GNR precursor polymer a group $R^b$ is alpha-hydrogen substituted aryl, it may form a 5-membered carbocyclic ring by together with a neighboring hydrogen substituted edge carbon by cycloannelation (see e.g. in GNR structure ix).

Application of GNRs

The resulting graphene nanoribbons may be used directly on the substrate on which they are prepared or they may be transferred to another substrate.

Based on these zigzag-related and cove related spin-polarized properties completely new performance profiles relevant in spintronic and semiconductor applications can be envisaged on the basis of possibly 'allcarbon' devices.

All percent, ppm or comparable values refer to the weight with respect to the total weight of the respective composition except where otherwise indicated. All cited documents are incorporated herein by reference. All molecular weights refer to the weight average molecular weight M, except where otherwise indicated.

Figure 1:
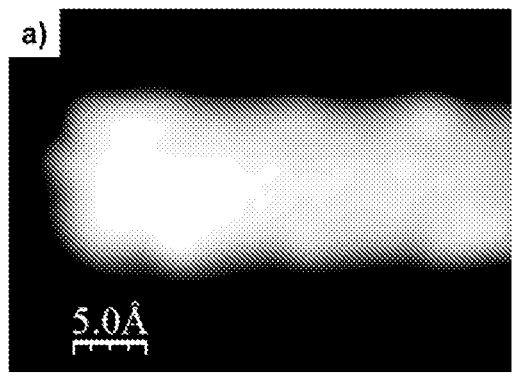
FIG. 1a shows a high resolution STM image of the terminus of a N=5 cove-edge zigzag GNR structure iii obtained after deposition of the precursor monomer 6 on Au (111) and subsequent polymerization and cyclodehydrogenation (U=−0.9V, I=0.4 nA).
FIG. 1b shows the same STM image as shown in FIG. 1a with a chemical model superimposed.
Figure 1:
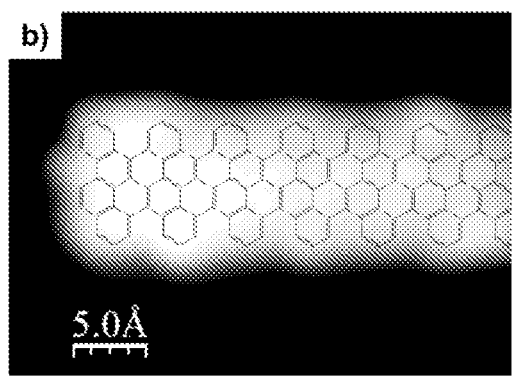

The following examples shall further illustrate the present invention without restricting the scope of this invention.

EXAMPLES

1. Synthesis Scheme of Monomer 1 (Monomer Structure V)

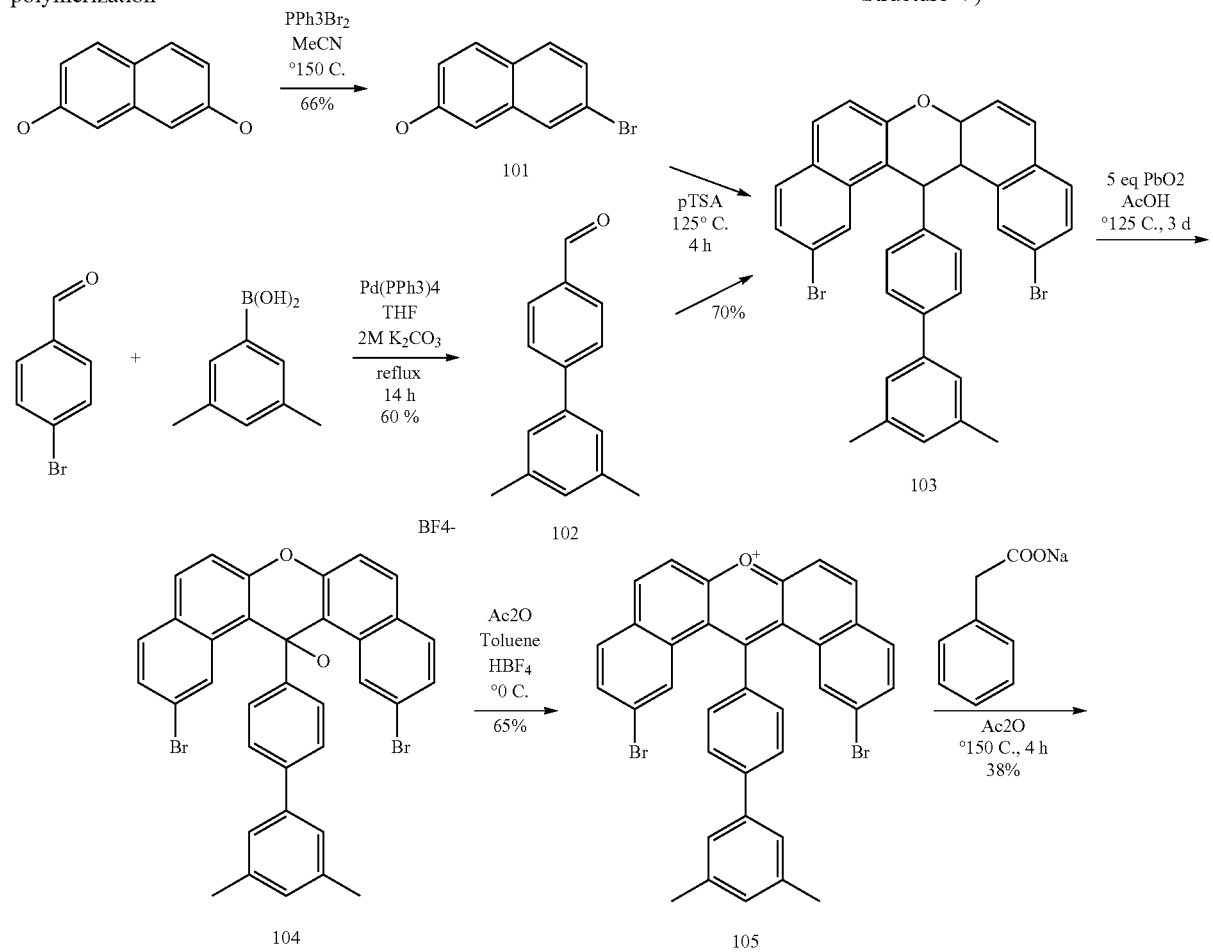

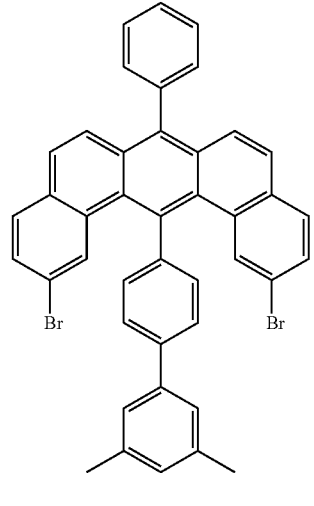

7-Bromo-2-Naphthol (101)

To a stirring suspension of Triphenyl phosphine (31.5 g) in Acetonitrile (50 mL) in a 250 mL-Schlenk-flask was added carefully Bromine (6.2 mL) at 0° C. with a syringe over 30 min. The yellow solution was warmed to room temperature and 2,7-Dihydroxynaphthalene (16 g) was added in one portion. The reaction was refluxed at 70° C. for one hour. After cooling to room temperature, the solvent was removed under reduced pressure. The reaction flask was connected to a gas-washing bottle filled with a concentrated sodium hydroxide solution. The flask was heated to 250° C. for two hours and the black residue dissolved in 100 mL Dichloromethane and purified via column chromatography (DCM:Pentan 1:1 to pure DCM). Product 101 was received as a beige powder (14.7 g, 66%)

DC: Dichloromethane:Pentane, 1:1, $R_f$=0.2
$^1$H-NMR: ∂ (300 MHz, CDCl$_3$)=7.76 (d, 1H), 7.63 (d, 1H), 7.54 (d, 1H), 7.32 (dd, 1H), 7.03 (dd, 1H), 6.98 (d, 1H), 4.98 (b, 1H)

3',5'-Dimethylbiphenyl-4-carbaldehyde (102)

p-Bromo-benzaldehyde (2.65 g) and 3,5-Dimethylphenyl boronic acid were added to a 250 mL-flask. After that, the solids were dissolved in THF (100 mL), Ethanol (60 mL) and 2M sodium carbonate solution (50 mL) and Argon bubbled through the solution for one hour. 10 mol % Tetrakistriphenyl-Palladium(0) (1 g) were added and the reaction mixture refluxed for 16 hours. The red solution was cooled to room temperature, extracted with 300 mL of Ethylacetate and washed with water. The organic phase was dried over MgSO$_4$ and the solvents removed under reduced pressure. The black residue was dissolved and purified via column chromatography (EA:Hexane, 1:10). The product 102 was collected as a yellow oil (1.8 g, 60%)

TLC: Ethylacetate:Hexane, 1:10, $R_f$=0.7
$^1$H-NMR: ∂ (300 MHz, CD$_2$Cl$_2$)=9.95 (s, 1H), 7.85 (d, 2H), 7.68 (d, 2H), 7.20 (s, 2H), 6.99 (s, 1H), 2.31 (s, 6H)

2,12-Dibromo-14-(3',5'-dimethylbiphenyl-4-yl)-14H-dibenzo[a,j]-Xanthene (103)

Bromonaphthol 101 (2.7 g) and 3',5'-Dimethylbiphenyl-4-Carbaldehyde 102 (1.27 g) were added together with p-Toluenesulfonic acid (25 mg) in a microwave reactor and heated to 130° C. under stirring. After 4 h at this temperature, the reaction mixture was cooled to room temperature and washed with a mixture of water and ethanol (3:1). The red solid was recrystallized from ethanol and the white powder filtered and washed with cold ethanol to give product 103 (2.62 g, 70%).

TLC: Ethylacetate:Hexane, 1:10, $R_f$=0.4
$^1$H-NMR: ∂ (500 MHz, C$_2$D$_2$Cl$_4$)=8.47 (s, 2H), 7.71 (d, 2H), 7.63 (d, 2H), 7.45-7.43 (m, 6H), 7.33 (d, 2H), 6.96 (s, 2H), 6.84 (s, 1H), 6.19 (s, 1H), 2.21 (s, 6H)
$^{13}$C-NMR: ∂ (500 MHz, C$_2$D$_2$Cl$_4$)=149.19; 143.05; 140.12; 139.74; 138.29; 132.54; 130.57; 129.51; 129.16; 128.42; 127.93; 127.63; 125.22; 125.03; 121.68; 118.67; 116.12; 37.72; 21.48
FD-MS: m/z=619.9

2,12-Dibromo-14-(3',5'-dimethyl-[1,1'-biphenyl]-4-yl)-14H-dibenzo[a,j]xanthene-14-ol (104)

The Xanthene 103 (2.5 g) was suspended together with lead (IV)oxide (7.71 g) in 50 mL acetic acid and stirred for 2 days at 130° C. The mixture was cooled to room temperature and poured on 300 mL water. The brown solid was filtered and recrystallized from a mixture of water and acetone (1:1). The product 104 is collected as a beige powder, which could not be purified. The crude product was used in the next step.

TLC: Ethylacetate:Hexane, 1:10, $R_f$=0.2

2,12-Dibromo-14-(3',5'-dimethylbiphenyl-4-yl)-dibenzo[a,j]-Xanthenium-Tetrafluoroborate (105)

The Xanthenol 104 (2.00 g) was dissolved in Toluene (5 mL) and acetic acid anhydride (15 mL) and the solution cooled to 0° C. Tetrafluoroboric acid (50 w %, 1.2 mL) was added carefully to precipitate the red product. It was stirred for 1 h and the product filtered and washed with 100 mL cold diethylether and a 2:1-mixture of petroleum ether and dichloromethane to yield 105 (1.58 g, 65%).

$^1$H-NMR: ∂ (500 MHz, C$_2$D$_2$Cl$_4$)=8.73 (d, 2H), 8.24 (d, 2H), 8.11 (d, 2H), 8.00 (d, 2H), 7.86 (d, 2H), 7.55 (d, 2H), 7.44 (s, 2H), 7.38 (s, 2H), 7.12 (s, 1H), 2.42 (s, 6H)

2,12-Dibromo-14-(3',5'-dimethyl-[1,1'-biphenyl]-4-yl)-7-phenyl-benzo[m]tetraphene (1)

The Xanthenium-Tetrafluoroborate 105 (1 g) was suspended together with sodium-2-phenylacetate (900 mg) in 12 mL acetic acid anhydride. It was stirred for 5 h at 155° C. and the solvent removed under reduced pressure. The brown residue was dissolved in Dichlormethane and purified via column chromatography (DCM:PE, 1:4). The yellow product 1 was recrystallized from chloroform (314 mg, 32%).

DC: Dichloromethane:Petroleum ether, 1:4, $R_f$=0.6

$^1$H-NMR: ∂ (500 MHz, $CD_2Cl_4$)=7.83 (d, 2H), 7.58-7.39 (m, 19H), 7.04 (s, 1H), 2.40 (s, 6H)

$^{13}$C-NMR: ∂ (500 MHz, $CD_2Cl_4$)=142.85; 142.48; 141.34; 139.01; 138.51; 137.96; 137.57; 132.78; 132.28; 132.18; 131.88; 131.37; 130.47; 129.91; 129.29; 129.22; 128.70; 127.97; 127.14; 127.03; 125.98; 125.80; 120.36; 118.75; 21.66

2. Synthesis of Monomers 2, 3 and Intermediate 115 (Monomer Structures VI, VII)

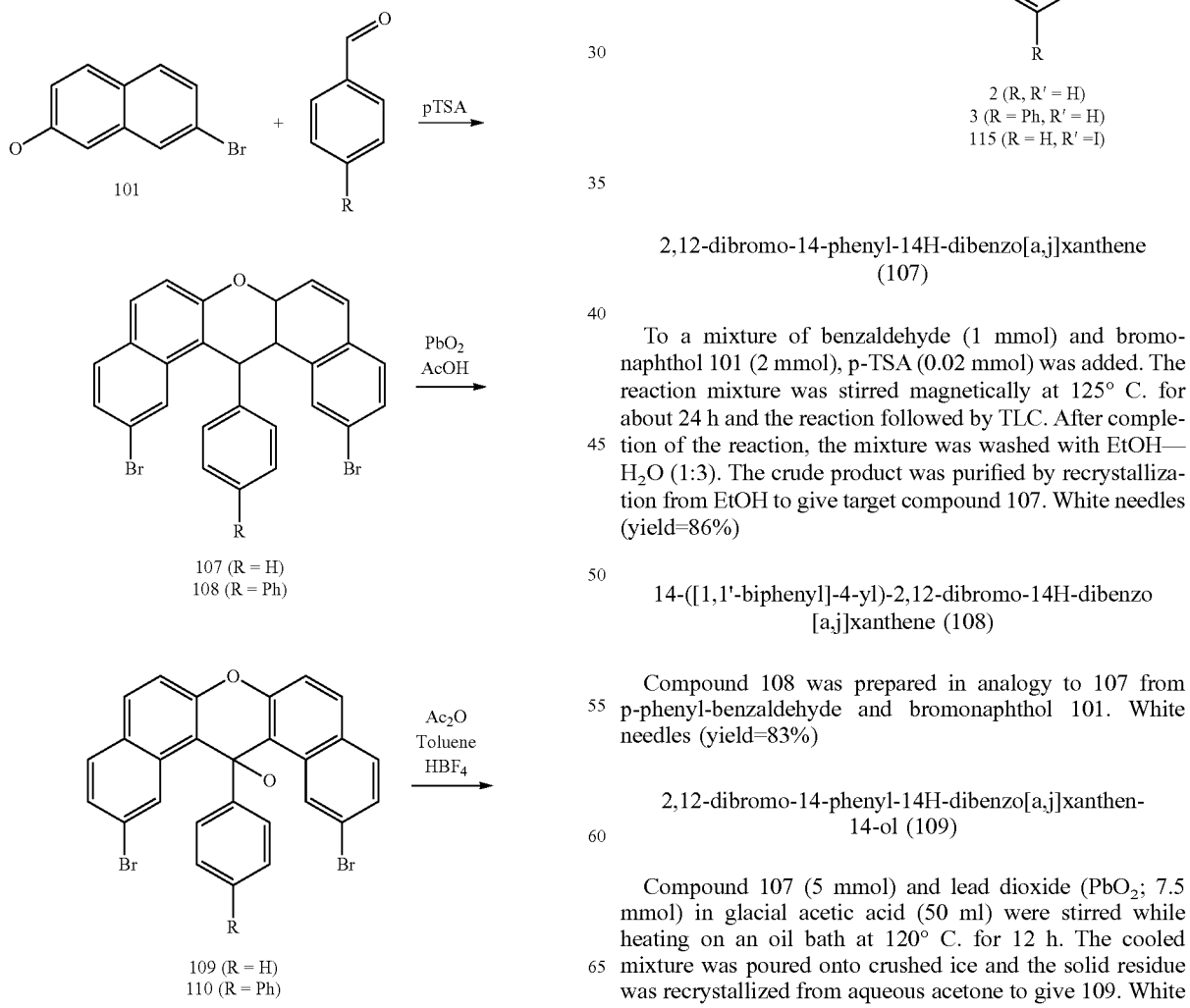

2,12-dibromo-14-phenyl-14H-dibenzo[a,j]xanthene (107)

To a mixture of benzaldehyde (1 mmol) and bromo-naphthol 101 (2 mmol), p-TSA (0.02 mmol) was added. The reaction mixture was stirred magnetically at 125° C. for about 24 h and the reaction followed by TLC. After completion of the reaction, the mixture was washed with EtOH—$H_2O$ (1:3). The crude product was purified by recrystallization from EtOH to give target compound 107. White needles (yield=86%)

14-([1,1'-biphenyl]-4-yl)-2,12-dibromo-14H-dibenzo[a,j]xanthene (108)

Compound 108 was prepared in analogy to 107 from p-phenyl-benzaldehyde and bromonaphthol 101. White needles (yield=83%)

2,12-dibromo-14-phenyl-14H-dibenzo[a,j]xanthen-14-ol (109)

Compound 107 (5 mmol) and lead dioxide ($PbO_2$; 7.5 mmol) in glacial acetic acid (50 ml) were stirred while heating on an oil bath at 120° C. for 12 h. The cooled mixture was poured onto crushed ice and the solid residue was recrystallized from aqueous acetone to give 109. White powder (yield=75%)

14-([1,1'-biphenyl]-4-yl)-2,12-dibromo-14H-dibenzo[a,j]xanthen-14-ol (110)

Compound 110 was prepared in analogy to compound 109 from compound 108. White powder (yield=71%)

2,12-dibromo-14-phenyldibenzo[a,j]xanthenylium tetrafluoroborate (111)

Compound 109 (5 mmol) in acetic anhydride (15 ml) and toluene (10 ml) were cooled to 0° C. and treated with terafluoroboric acid (ca. 25 mmol) until no further precipitation occurred. The cooled solution was filtered and washed with anhydrous ether to yield 111 as product. Orange red powder (yield=90%)

14-([1,1'-biphenyl]-4-yl)-2,12-dibromodibenzo[a,j]xanthenylium tetrafluoroborate (112)

Compound 112 was prepared in analogy to compound 111 from compound 110. Orange red powder (yield=92%)

2,12-dibromo-7,14-diphenylbenzo[m]tetraphene (2)

A mixture of pyrylium salt 111 (3 mmol) and sodium 2-phenylacetate (9 mmol) in acetic anhydride ($Ac_2O$ 50 ml) was stirred at 150° C. for 12 h under argon atmosphere. After cooling to room temperature, the precipitate was filtered off and washed with $Ac_2O$, then methanol. The crude product was recrystallized from chloroform and hexane to give monomer 2. Gray powder (yield=34%)

1H NMR (300 MHz, CDCl3) δ ppm 7.71 (dd, J=7.78 Hz, 4H), 7.79-7.37 (m, 5H), 7.55-7.36 (m, 11H)

FD-MS: m/z=589.1

14-([1,1'-biphenyl]-4-yl)-2,12-dibromo-7-phenyl-benzo[m]tetraphene (3)

Monomer 3 was prepared in analogy to monomer 2 from compound 112. Gray powder (yield=32%)

$^1$H NMR (500 MHz, 1,1,2,2-tetrachloroethane-d2, 403K) δ ppm 7.77 (d, J=7.85 Hz, 2H), 7.71 (d, J=7.22 Hz, 2H), 7.55 (s, 2H), 7.49 (d, J=8.68 Hz, 4H), 7.46-7.34 (m, 12H), 7.31 (t, J=7.27, 1H)

FD-MS: m/z=665.7

2,12-dibromo-7-(4-iodophenyl)-14-phenylbenzo[m]tetraphene (115)

The compound 115 was prepared in analogy to monomer 1 from compound 111 and sodium 2-(p-iodophenyl)acetate. Brown powder (yield=34%)

$^1$H NMR (300 MHz, $CDCl_3$) δ ppm 7.95 (d, J=8.3 Hz, 2H), 7.8-7.65 (m, 3H), 7.63 (s, 1H), 7.60 (s, 1H), 7.55-7.36 (m, 10H), 7.2 (d, J=8.37 Hz, 2H)

FD-MS: m/z=714.3

3. Synthesis of Monomer 4 (Monomer Structure VI)

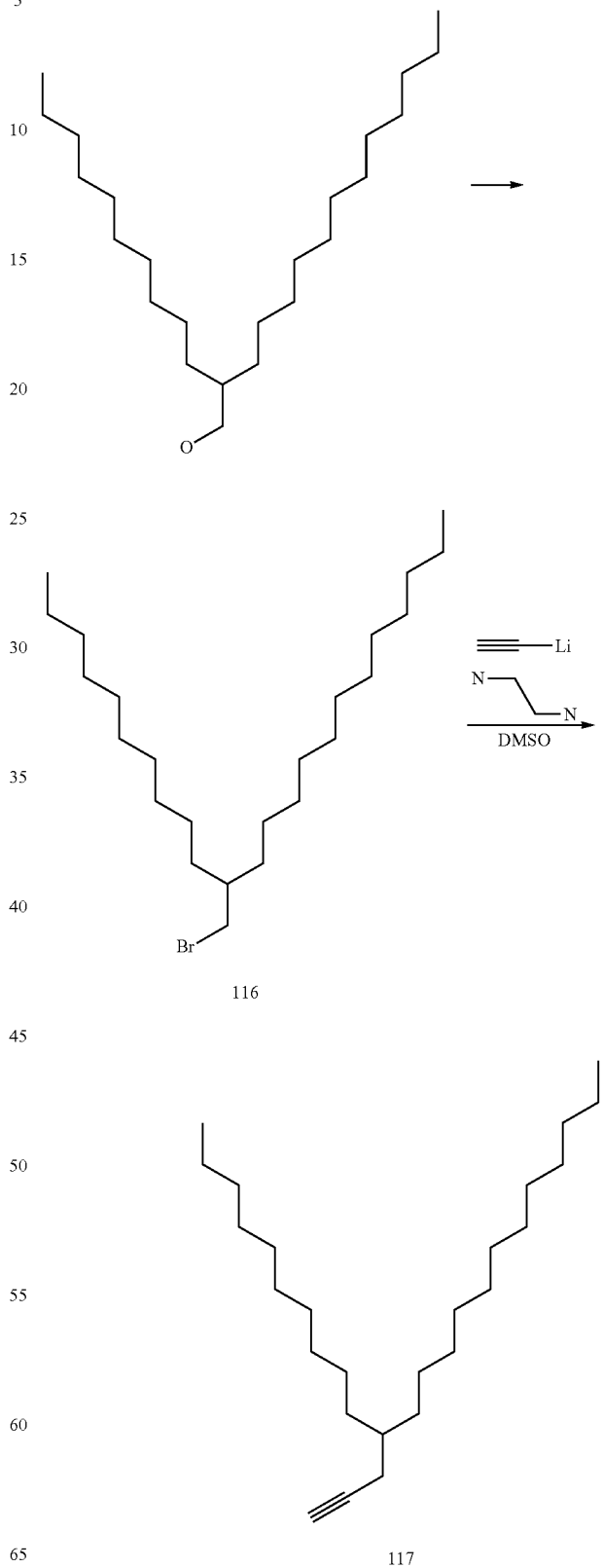

1-bromo-2-decyl-tetradecane (116)

2-decyltetradecan-1-ol (30 g, 84.5 mmol) and triphenylphosphine (45 g, 169 mmol) were dissolved in dichloromethane (100 ml) and cooled to 0° C. To the mixture N-bromosuccinimide (23 g, 127 mmol) was added slowly, then stirred at room temperature for 24 hours. After evaporation of solvents in vacuo the products were dissolved in hexane. Purification by column chromatography (silica gel, hexane) yielded compound 116. Colorless oil (yield=97%).

4-decyl-hexadec-1-yne (117)

To a suspension of a lithium acetylide-ethylenediamine complex (40 mmol) in DMSO (30 ml) was added compound 116 (10 mmol) at 0° C. The reaction mixture was stirred for 12 h at room temperature (23° C.). Then sat. aq. NH$_4$Cl (20 ml) was added to the mixture. The mixture was extracted with ether, washed with brine, dried over MgSO$_4$, and concentrated. The residue was chromatographed over silica gel (hexane) to afford 117. Colorless oil (yield=99%).

2,12-dibromo-7-(4-(4-decyl-hexadecyl)phenyl)-14-phenylbenzo[m]tetraphene (4)

To a mixture of compound 115 (0.6 mmol) and PdCl$_2$(PPh$_3$)$_2$ (0.03 mmol) in THF (50 ml), compound 117 (0.9 mmol) and CuI (0.06 mmol) was added. The mixture was bubbled with argon for 20 min and then stirred for 24 h at room temperature. The reaction was monitored by TLC. After the reaction was completed, the mixture was extracted with ethyl acetate, washed with brine, dried over MgSO$_4$, and concentrated. The residue was passed through a short pad of silca gel (AcOEt) to afford the crude Sonogashira coupling product.

The crude product was dissolved in 50 ml dry THF and Palladium on active carbon (Pd/C, 10%) was added. The mixture was stirred in an autoclave under hydrogen (H$_2$) atmosphere (5 bar) at r.t. for 12 h. The reaction mixture was filtered and the solution concentrated under vacuum. The residue was chromatographed over silica gel (hexane/AcOEt=10/1) to afford compound 4. Light yellow powder (yield=88%).

1H NMR (300 MHz, CDCl3) δ ppm 7.8-7.364 (m, 3H), 7.61 (s, 1H), 7.58 (s, 2H), 7.51-7.38 (m, 11H), 7.37-7.31 (m, 2H), 2.77 (t, J=7.66 Hz), 1.81 (m, 2H), 1.41 (m, 1H), 1.37-0.97 (d, J=10.87, 42H), 0.88 (m, 6H)

FD-MS: m/z=953.4

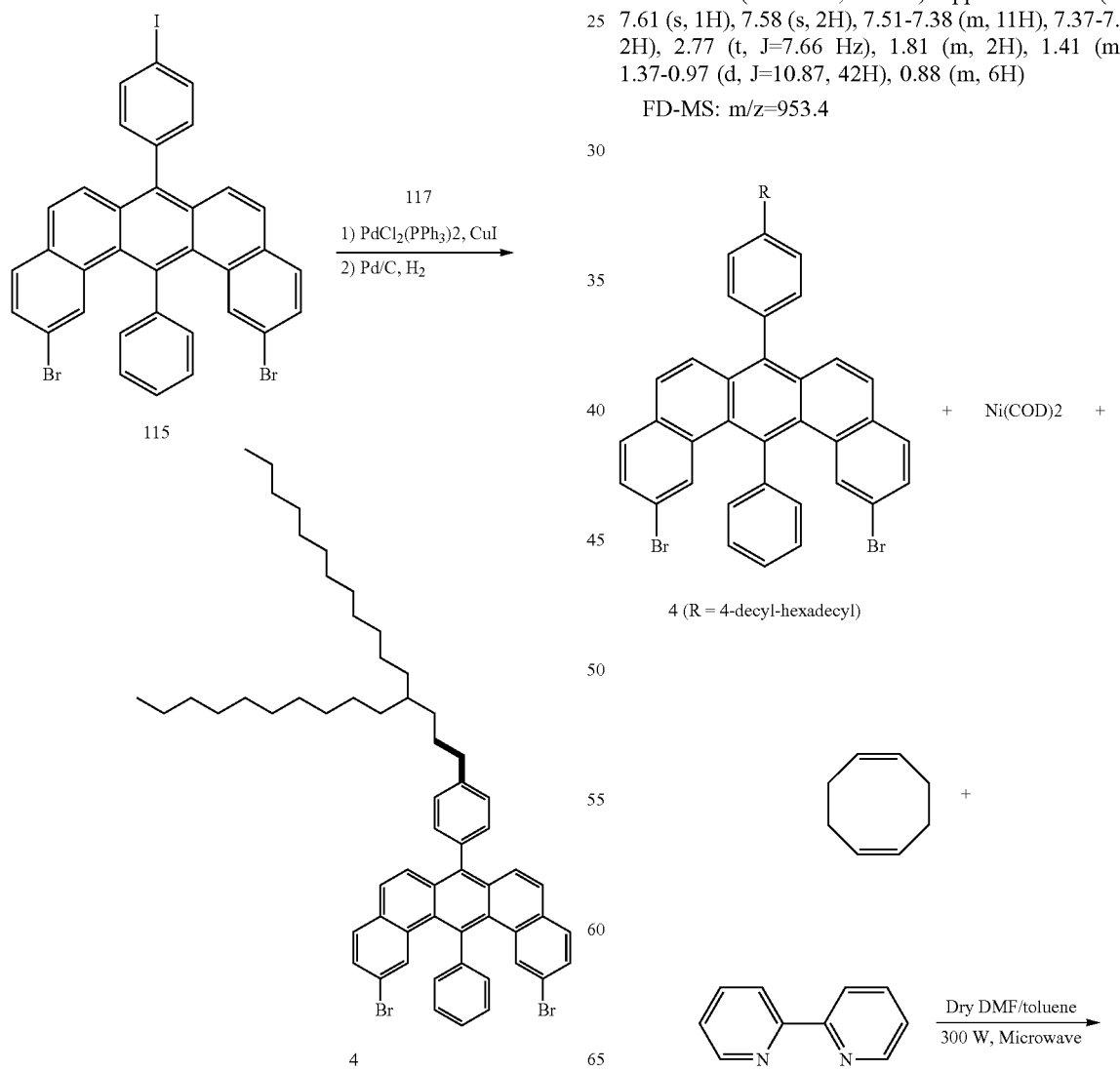

-continued

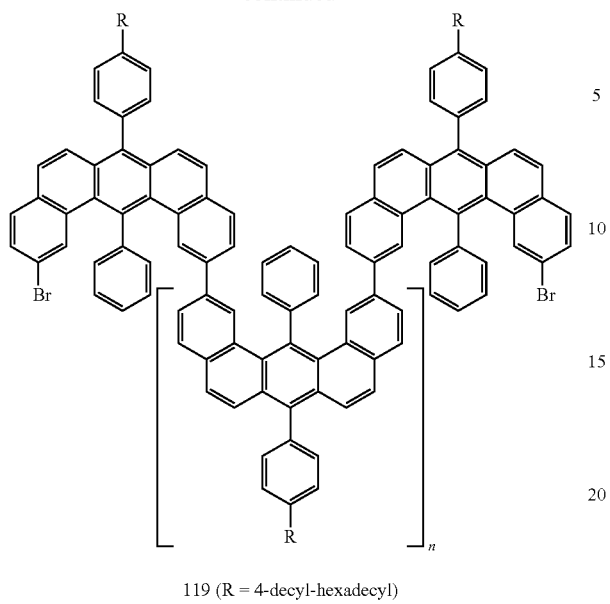

119 (R = 4-decyl-hexadecyl)

Polymerization of Monomer 4 to Yield Polymer 119

Bis(1,5-cyclooctadiene)nickel (0) (23 mg, 0.084 mmol), 1,5-cyclooctadiene (0.01 ml, 0.084 mmol), and 2,2'-bipyridine (13 mg, 0.084 mmol) in dry DMF (4 ml) was charged under argon in a microwave tube equipped with magnetic stirrer bar and heated at 80° C. for 30 min.

A solution of monomer 4 (20 mg, 0.02 mmol) in dry toluene (4 ml) was added. The mixture was vigorously stirred in a CEM Discover microwave reactor at 300 W and active cooling, keeping the temperature at 110° C. for 12 hours. After the reaction was completed, the mixture was poured into a mixture of methanol and concentrated HCl (1:1, 20 ml), and stirred for 4 h. The precipitated yellow polymer 119 was filtered off and dried under vacuum at 80° C. overnight. Yellow powder (yield=85%)

Polymer 119 is transformed into the corresponding GNR by cyclodehyrogenation reaction in solution as described in WO2013/061258.

4. Synthesis of Monomer 5 (Monomer Structure IV)

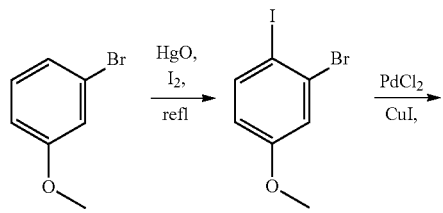

-continued

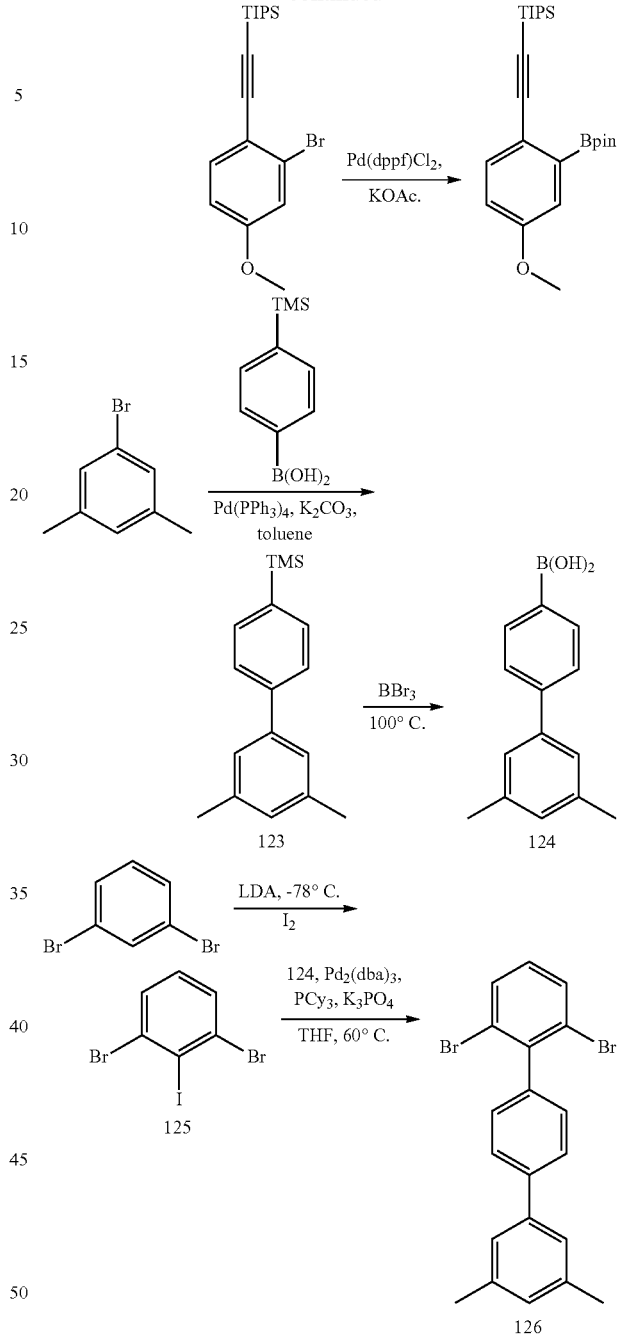

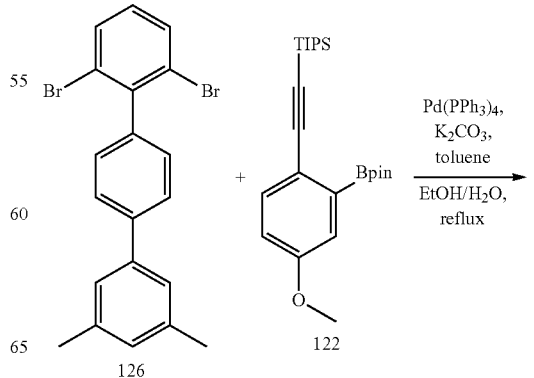

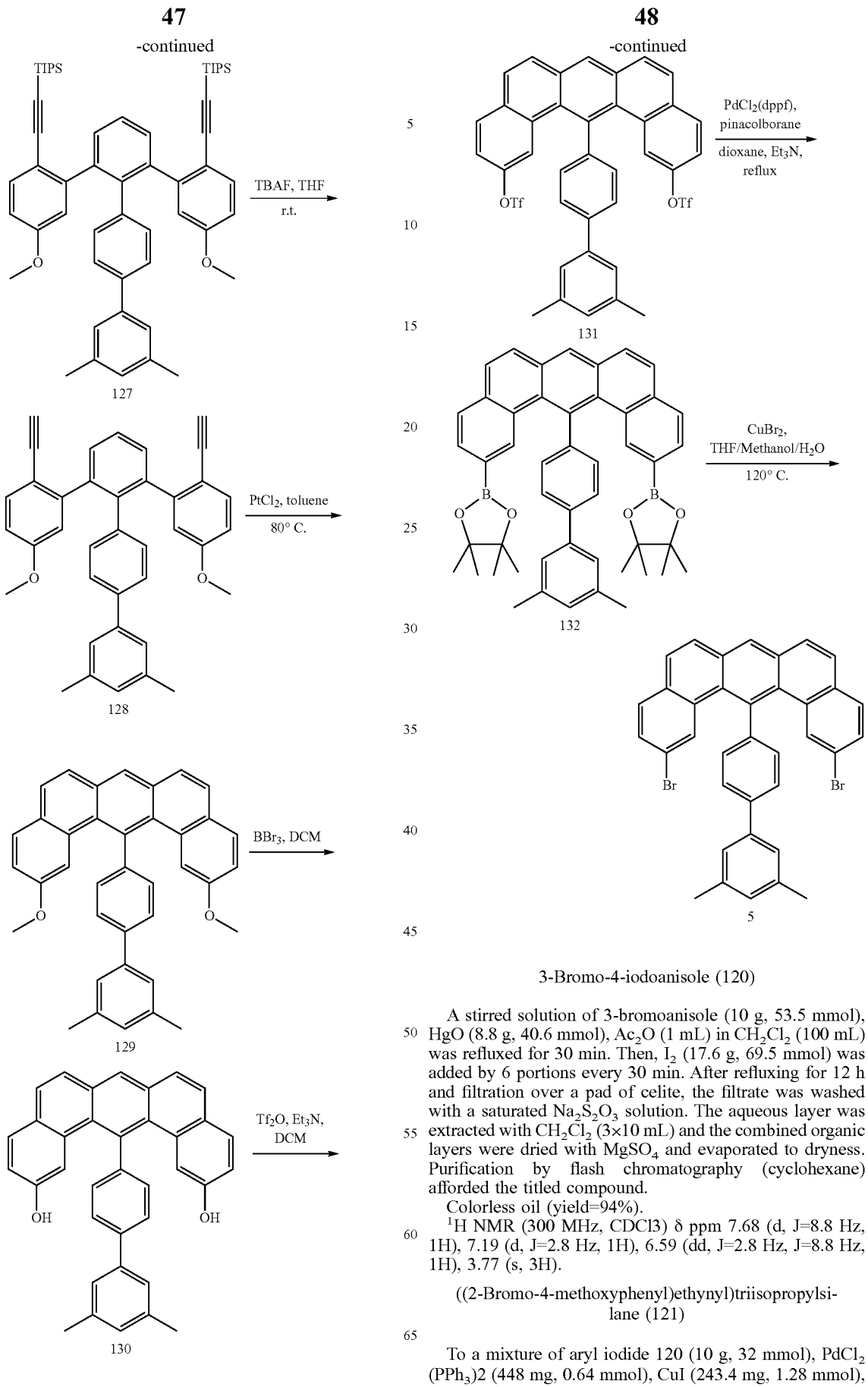

3-Bromo-4-iodoanisole (120)

A stirred solution of 3-bromoanisole (10 g, 53.5 mmol), HgO (8.8 g, 40.6 mmol), Ac$_2$O (1 mL) in CH$_2$Cl$_2$ (100 mL) was refluxed for 30 min. Then, I$_2$ (17.6 g, 69.5 mmol) was added by 6 portions every 30 min. After refluxing for 12 h and filtration over a pad of celite, the filtrate was washed with a saturated Na$_2$S$_2$O$_3$ solution. The aqueous layer was extracted with CH$_2$Cl$_2$ (3×10 mL) and the combined organic layers were dried with MgSO$_4$ and evaporated to dryness. Purification by flash chromatography (cyclohexane) afforded the titled compound.

Colorless oil (yield=94%).

$^1$H NMR (300 MHz, CDCl3) δ ppm 7.68 (d, J=8.8 Hz, 1H), 7.19 (d, J=2.8 Hz, 1H), 6.59 (dd, J=2.8 Hz, J=8.8 Hz, 1H), 3.77 (s, 3H).

((2-Bromo-4-methoxyphenyl)ethynyl)triisopropylsilane (121)

To a mixture of aryl iodide 120 (10 g, 32 mmol), PdCl$_2$(PPh$_3$)2 (448 mg, 0.64 mmol), CuI (243.4 mg, 1.28 mmol), TEA (14 mL) in THF (100 mL) was added dropwise under an argon atmosphere a solution of (Triisopropylsilyl)acetylene (8.74 g, 48 mmol). The mixture was stirred at room temperature overnight. Then Et$_2$O (20 mL) was added to the crude and the mixture was filtered over a short pad of celite. The organic layer was washed with brine (5 mL) twice, separated, dried over MgSO$_4$, filtered, and concentrated. Purification by flash chromatography afforded alkyne 121. Colorless oil (yield=93%)

Triisopropyl((4-methoxy-2-(4,4,5,5-tetramethyl-1,3, 2-dioxaborolan-2-yl)phenyl)ethynyl)silane (122)

A 250 ml round flask was charged with alkyne 121 (19.5 g, 53.1 mmol), Bis(pinacolato)diboron (14.8 g, 58.4 mmol), KOAc (15.6 g, 159 mmol) and PdCl$_2$(dppf) (1.2 g, 1.6 mmol), then the stirring mixture was purged by Argon for 20 min. After the mixture was stirred overnight at 80° C. under an argon atmosphere, the mixture was extracted with ethyl acetate (20 ml×3). The combined organic layer was dried over MgSO$_4$, filtered and concentrated. The crude residue was purified by pass through a short pad of silica gel to remove the catalyst and used directly for the next step. Brown yellow oil (Yield=85%)

(3',5'-Dimethyl-[1,1'-biphenyl]-4-yl)trimethylsilane (123)

A 250 ml round flask was charged with 1-bromo-3,5-dimethylbenzene (6 g, 32.4 mmol), (4-(trimethylsilyl)phenyl)boronic acid (9.44 g, 48.6 mmol), K$_2$CO$_3$ solution (18 g in 10 ml water), ethanol 10 ml, toluene 50 ml. The mixture was bubbled with argon for 10 min, then Pd(PPh$_3$)4 (1.87 g, 1.62 mmol) was added. The resulting mixture was treated with liquid nitrogen bath. After three times freeze-pump-thaw procedure, the mixture was refluxed overnight. The reaction was monitored by TLC. After the reaction finished, the mixture was washed with deionized water and the water layer was extracted with ethyl acetate (10 ml×2). The combined organic layer was dried over MgSO$_4$, filtered and concentrated. The crude product was purified by chromatography to afford compound 123. Colorless oil (yield=95%)

(3',5'-Dimethyl-[1,1'-biphenyl]-4-yl)boronic acid (124)

Compound 123 (8 g, 31.4 mmol) was treated with neat boron tribromide (12.6 g, 50.3 mmol) under argon. A condenser was attached that was also charged with argon, and the solution was heated to 100° C. for 4 h. Once cooled, excess boron tribromide was distilled off under vacuum at room temperature. The resulting gray-purple solid was dissolved in dry hexane (50 ml) and cooled to 0° C. with an ice bath. Water was slowly added dropwise while stirring vigorously until the reaction had been fully quenched. The resulting mixture was filtered and the white solid was washed with deionized water and hexane. The white powder was dried at 80° C. under vacuum overnight, yielding boronic acid 124. White powder (yield=98%)

1,3-Dibromo-2-iodobenzene (125)

At −75° C., butyllithium (42.4 mmol) in hexanes (50 mL) and diisopropylamine (42.4 mmol) were added successively to tetrahydrofuran (20 mL). After 15 min 1,3-dibromobenzene (5.12 mL, 10 g, 42.4 mmol) was added. The mixture was kept for 2 h at −75° C. before a solution of iodine (10.76 g, 42.4 mmol) in tetrahydrofuran (50 mL) was added. After addition of a 10% aqueous solution (0.10 L) of sodium thiosulfate, the mixture was extracted with diethyl ether (3×10 mL). The combined organic layers were dried over sodium sulfate before being evaporated to dryness. Upon crystallization from ethanol (100 mL), colorless platelets were obtained. Colorless platelets (yield=91%)

2,6-dibromo-3'',5''-dimethyl-1,1':4',1''-terphenyl (126)

In a glove box, Pd$_2$(dba)$_3$ (1.02 g, 1.11 mmol), PCy$_3$ (1.25 g, 4.45 mmol), compound 125 (8.04 g, 22.23 mmol), boronic acid 124 (5.03 g, 22.23 mmol) were added to a reaction vessel that was equipped with a stir bar. A degassed K$_3$PO$_4$ (14.16 g, 66.7 mmol) water solution was then added, followed by 100 ml anhydrous THF. The reaction mixture was then stirred at 60° C. for 3 days. After the reaction finished, the reaction mixture was diluted with EtOAc, then extracted by EtOAc three times, dried, filtered and concentrated. The final product was obtained after purification by column chromatography on silica gel. Colorless oil (yield=48%)

Triisopropyl((5-methoxy-3'-(5-methoxy-2-((triisopropylsilyl)ethynyl)phenyl)-3''',5'''-dimethyl-[1,1':2', 1'':4'',1'''-quaterphenyl]-2-yl)ethynyl)silane (127)

A 100 ml round flask was equipped with compound 126 (1.16 g, 2.79 mmol), boronic ester 122 (3.47 g, 8.36 mmol) in 50 ml toluene and 5 ml K$_2$CO$_3$ (2.31 g, 16.72 mmol) water solution. After bubbled with argon for 10 min, the catalyst Pd(PPh$_3$)$_4$ (322 mg, 0.28 mmol) was added. The reaction mixture was then heated at reflux temperature overnight. The reaction was stopped after TLC indicated that the starting material was totally converted. The mixture was extracted with EtOAc (10 ml×3), then the combined organic layer was dried, filtered and concentrated. The residue was purified by column chromatography yielding product 127. Yellow solid (yield=81%)

2-Ethynyl-3'-(2-ethynyl-5-methoxyphenyl)-5-methoxy-3''',5'''-dimethyl-1,1':2',1'':4'',1'''-quaterphenyl (128)

Compound 127 (1.5 g, 1.8 mmol) was dissolved in 50 ml THF, and then TBAF (5.69 g, 18 mmol) was added to the yellow solution. After stirred for 2 h, the reaction mixture was washed with water and then extracted with EtOAc. The combined organic layer was dried over MgSO$_4$ and filtered. The solvent was removed by rotation evaporator. The obtained white solid was used directly for the next step. White solid (yield=99%)

14-(3',5'-Dimethyl-[1,1'-biphenyl]-4-yl)-2,12-dimethoxybenzo[m]tetraphene (129)

A 100 ml round flask was charged with compound 128 (1.1 g, 2.12 mmol) and PtCl$_2$ (56.4 mg, 0.21 mmol), then the mixture was kept under vacuum condition for 20 min and refilled with argon. 60 ml of anhydrous toluene was added by syringe. The mixture was heated at 80° C. for 24 h until reaction finished which showed by TLC plate. The solvent was removed under vacuum condition and the residue was purified by chromatography yielding final product. White solid (yield=63%)

14-(3',5'-Dimethyl-[1,1'-biphenyl]-4-yl)benzo[m]tetraphene-2,12-diol (130)

Compound 129 (250 mg, 0.48 mmol) was dissolved in 40 ml dry DCM under argon protection. Then, 5.78 mL 1M BBr$_3$ (1.45 g, 5.78 mmol) was added dropwise to the solution at 0° C. The solution was then allowed to warm to room temperature and stirred for 6 h. Then, the reaction was quenched by adding 10 ml water slowly at 0° C. The mixture was washed with water and extracted with DCM. The organic layer was dried over MgSO$_4$, filtered and concentrated. The residue was recrystallized from DCM/hexane (1:50). White green powder (yield=82%)

14-(3',5'-Dimethyl-[1,1'-biphenyl]-4-yl)benzo[m]tetraphene-2,12-diyl bis(trifluoromethanesulfonate) (131)

Compound 130 (236 mg, 0.48 mmol) was dissolved in 20 ml DCM and cooled to 0° C. by an ice bath, then 0.36 ml Et$_3$N (2.6 mmol) was added drop wise. 1M Tf$_2$O (1.44 mL) solution was added by syringe. The ice bath was then removed and the mixture solution was warmed to room temperature and stirred for 4 h. After TLC showed the completion of the reaction, the solvent was removed and the residue was purified by chromatography yielding product. White solid (yield=78%)

2,2'-(14-(3',5'-Dimethyl-[1,11-biphenyl]-4-yl)benzo[m]tetraphene-2,12-diyl)bis(4,4,5,5-tetramethyl-1,3,2-dioxaborolane) (132)

A Schlenk tube was charged with compound 131 (110 mg, 0.145 mmol), PdCl$_2$(dppf) (6 mg, 0.007 mmol), 5 ml dry dioxane and Et$_3$N (0.12 ml, 0.87 mmol), the solution was degassed and pinacolborane (0.08 mL, 0.58 mmol) was added. The mixture solution was then heated at refluxing temperature for 12 h. Then the solvent was removed and the residue was purified by chromatography. Light yellow oil (yield=71%)

2,12-Dibromo-14-(3',5'-dimethyl-[1,1'-biphenyl]-4-yl)benzo[m]tetraphene (5)

Compound 131 (50 mg, 0.07 mmol) and CuBr$_2$ (95 mg, 0.42 mmol) was added to a sealtube, then 2 ml THF, 6 ml Methanol and 4 ml water was added. The tube was sealed and heated at 120° C. overnight. The mixture was then extracted with DCM (5 mL×3), dried over MgSO$_4$, filtered and concentrated. The residue was purified by chromatography and HPLC to afford monomer 5. Colorless solid (Yield=60%)
FD-MS: m/z=615.3

5. Synthesis of Monomers 6, 7 (Monomer Structure III)

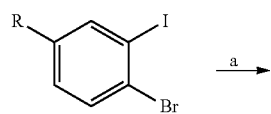

132a (R = H)
132b (R = t-Bu)

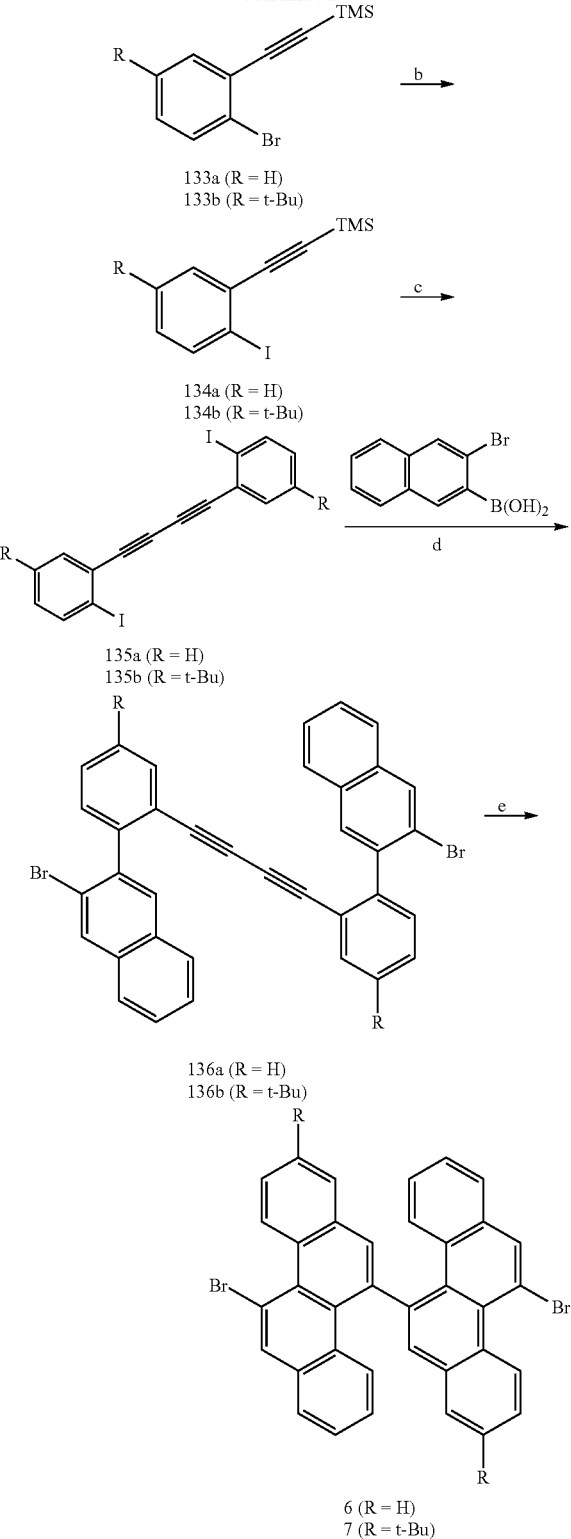

a) PdCl$_2$(PPh$_3$)$_2$, CuI, Et$_3$N, THF, r.t, 24 h. b) n-BuLi, THF, ICH$_2$CH$_2$I, -78° C. to r.m. c) CuCl, DMF, Air, 80° C., 6 h. d) Pd(PPh$_3$)$_4$/Na$_2$CO$_3$, THF/H$_2$O/EtOH, 60° C., 24 h. e) PdCl$_2$, Toluene, 85° C., 24 h.

Compound 133:

A 50 mL round bottomflask equipped with a magnetic stir bar was charged with compound 132 (35 mmol), THF (100 mL), triethylamine (20 mL, 150 mmol), PdCl$_2$(PPh$_3$)$_2$ (500 mg, 0.7 mmol), CuI (150 mg, 0.754 mmol) and trimethylsilylacetylene (5.25 mL, 37.1 mmol) under argon atmosphere. The reaction mixture was stirred overnight at room temperature, diluted in CH$_2$Cl$_2$, washed with NH$_4$Cl and dried over Mg$_2$SO$_4$. The solvent was removed under reduced pressure and the crude product was purified by flash chromatography on silica gel with hexanes as eluent to afford the desired compound 133 (133a: 82%, 133b: 85%) as yellow orange oil.

133a: $^1$H-NMR (CD$_2$Cl$_2$, 250 MHz): 7.58 (d, 1H), 7.49 (dd, 1H), 7.24 (t, 1H), 7.16 (t, 1H), 0.28 (s, 9H);

133b: $^1$H-NMR (CD$_2$Cl$_2$, 250 MHz): 7.48 (s, 1H), 7.32 (dd, 1H), 7.18 (dd, 1H), 1.6 (s, 9H), 0.28 (s, 9H);

Compound 134:

A 250 mL round bottom flask equipped with a magnetic stir bar was charged with compound 133 (11.9 mmol), THF (100 mL). The temperature was cooled to −78° C. and n-BuLi (1.4 mL, 23.7 mmol) was added slowly. The reaction mixture was stirred for one hour and 1,2-diiodoethane was added (17.8 mmol). The reaction mixture was stirred overnight at room temperature, diluted in CH$_2$Cl$_2$, washed with H$_2$O and dried over Mg$_2$SO$_4$. The solvent was removed under reduced pressure and the crude product was purified by flash chromatography on silica gel with hexanes as eluent to afford the desired compound 134 (134a:88%, 134b:90%) as dark orange oil.

134a: $^1$H-NMR (CD$_2$Cl$_2$, 250 MHz): 7.55 (d, 1H), 7.47 (dd, 1H), 7.21 (t, 1H), 7.15 (t, 1H), 0.28 (s, 9H);

134b: $^1$H-NMR (CD$_2$Cl$_2$, 250 MHz): 7.58 (s, 1H), 7.38 (dd, 1H), 7.24 (dd, 1H), 1.55 (s, 9H), 0.27 (s, 9H);

Compound 135:

To a dimethylformamide (DMF) (100 mL) solution of compound 134 (32.3 mmole) placed in round bottom flask was added CuCl (32.3 mmol) equipped with a magnetic stirring bar. The reaction mixture was stirred for 6 h at 80° C. and quenched with 1.0 M HCl(aq). The aqueous layer was separated and extracted with 100 mL of diethyl ether. The combined ethereal layer was washed with brine and dried over Mg$_2$SO$_4$, concentration of the solution in vacuo gave a brown residue that was purified by column chromatography (dichloromethane/hexane=1/10) to afford compound 135 (135a:78%, 135b:83%) as a yellow solid.

135a: $^1$H-NMR (CD$_2$Cl$_2$, 250 MHz): 7.82 (d, 1H), 7.55 (d, 1H), 7.28 (t, 1H), 7.12 (t, 1H); FD-MS (8 KV): m/z 453.9.

135b: $^1$H-NMR (CD$_2$Cl$_2$, 250 MHz): 7.86 (s, 1H), 7.66 (d, 1H), 7.23 (d, 1H), 1.45 (s, 9H); FD-MS (8 KV): m/z 565.8.

Compound 136:

Nitrogen was bubbled through a mixed solution of THF (100 mL), EtOH (20 mL) and water (20 mL) for 30 min, and to this solution was added compound 135 (4.96 mmol), Pd(PPh3)4 (0.5 mmol), K2CO3 (29.76 mmol) and bromo-naphthalene-boronic acid (9.95 mmol). The mixture was heated at 60° C. for 36 h. The solution was extracted three times with ethyl acetate. After removal of the solvent in vacuo, the crude material was purified by column chromatography (dichloromethane/hexane=1/10) to afford compound 136 (136a:50%, 136b:56%) as a yellow solid.

136a: $^1$H-NMR (CD$_2$Cl$_2$, 250 MHz): 8.01 (s, 1H), 7.76 (d, 1H), 7.68 (d, 1H), 7.54 (s, 1H), 7.45 (m, 2H), 7.3 (m, 4H); $^{13}$C-NMR (CD$_2$Cl$_2$, 250 MHz): 144.78, 138.74, 134.19, 133.49, 132.35, 131.45, 130.59, 130.45, 129.29, 128.34, 128.22, 127.51, 127.16, 127.07, 122.09, 121.32, 81.14, 76.81 FD-MS (8 KV): 611.8 m/z.

136b: $^1$H-NMR (CD$_2$Cl$_2$, 250 MHz): 8.28 (s, 1H), 8.23 (s, 1H), 8.14 (s, 1H), 8.01 (dd, 1H), 7.88 (dd, 1H), 7.64 (m, 2H), 7.36 (m, 2H); $^{13}$C-NMR (CD$_2$Cl$_2$, 250 MHz): 145.58, 136.47, 134.14, 130.81, 129.55, 127.63, 126.82, 124.88, 124.65, 124.13, 124.08, 123.96, 123.54, 122.76, 117.85, 115.64, 77.38, 74.31, 33.68, 31.34. FD-MS (8 KV): 723.8 m/z.

Monomers 6 and 7:

A reaction tube containing PtCl$_2$ (0.07 mmol) was dried in vacuo for 1 h, and vacuum was filled with nitrogen with a nitrogen balloon. To this round bottom flask was added compound 136 (0.74 mmol) and toluene (74 mL), and the mixture was stirred at 25° C. for 5 min before it was heated at 90° C. for 24 h. After removal of solvent in vacuo, the crude material was purified by column chromatography (dichloromethane/hexane=1/5) to afford compound 6, respectively 7 (6:70%, 7:78%) as a yellow solid.

6: $^1$H-NMR (CD$_2$Cl$_2$, 250 MHz): 9.55 (dd, 1H), 8.28 (s, 1H), 7.78 (d, 1H), 7.68 (m, 3H), 7.69 (t, 1H), 7.54 (t, 1H), 7.25 (t, 1H), 6.74 (t, 1H); $^{13}$C-NMR (CD$_2$Cl$_2$, 250 MHz): 138.82, 133.26, 131.84, 131.64, 130.38, 130.01, 128.59, 128.47, 126.82, 126.74, 126.39, 126.09, 125.81, 124.53, 124.04, 120.65, 116.11, 115.72. FD-MS (8 KV): 611.7 m/z.

7: $^1$H-NMR (CD$_2$Cl$_2$, 250 MHz): 9.54 (dd, 1H), 8.28 (s, 1H), 7.81 (d, 1H), 7.65 (m, 4H), 7.24 (t, 1H), 6.75 (t, 1H), 1.34 (s, 9H); $^{13}$C-NMR (CD$_2$Cl$_2$, 250 MHz):150.55, 140.11, 134.29, 132.95, 132.82, 131.84, 130.76, 129.76, 129.29, 127.87, 127.75, 127.61, 127.19, 126.75, 125.67, 123.83, 123.48, 117.36, 35.09, 31.28. FD-MS (8 KV): 723.9 m/z.

6. Synthesis of Monomer 8 (Monomer Structure X)

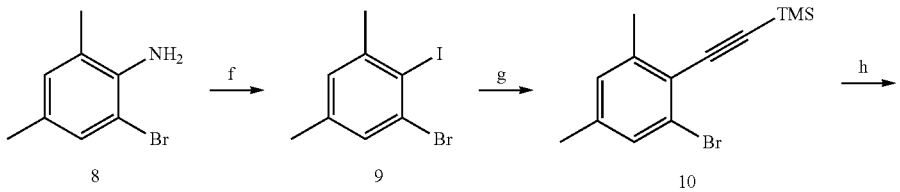

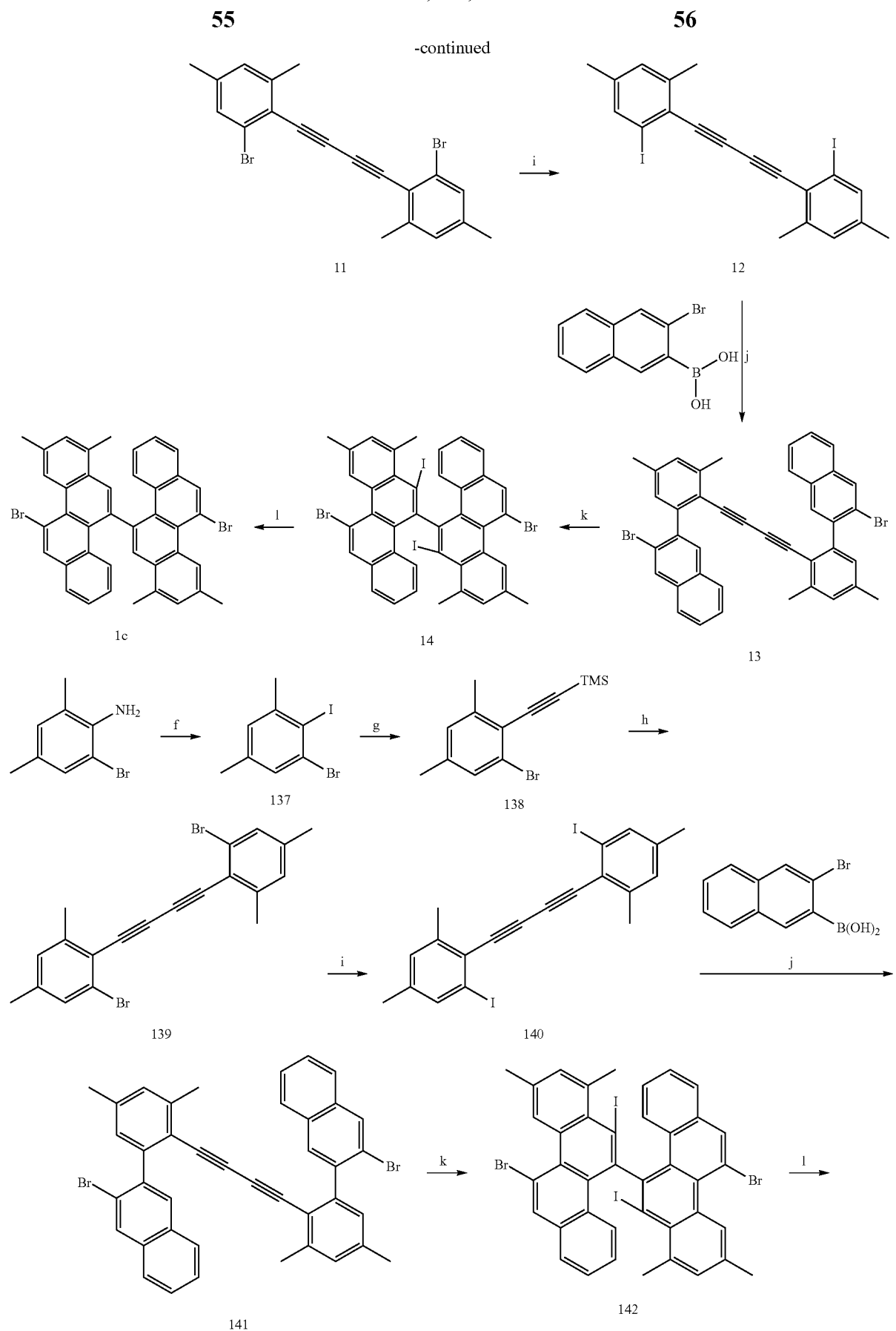
-continued

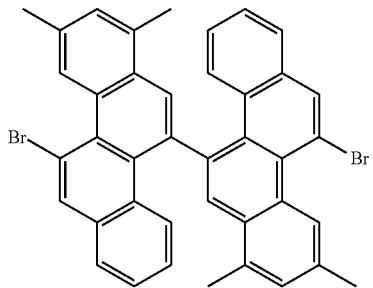

8 f) Sandmeyer reaction. g) PdCl$_2$(PPh$_3$)$_2$, CuI, Et$_3$N, THF, r.t, 24 h. h) CuCl, DMF, Air, 80° C., 6. i) n-BuLi, THF, ICH$_2$CH$_2$I, -78° C. to r.m. j) Pd(PPh$_3$)$_4$/Na$_2$CO$_3$, THF/H$_2$O/EtOH, 60° C., 24 h. k) ICl, DCM, -78° C., 3 h. I) hv, THF, 2 h, r.m.

Compound 137:

A mixture of dimethyl-bromoaniline (0.05 mol), H$_2$O (100 mL), and 37% aq.HCl (100 mL) was heated to 80° C. while stirring. The mixture was stirred 30 min followed by cooling to 0° C. on an ice/water bath. NaNO$_2$ (0.055 mol) was added maintaining the internal temperature below 10° C. The resulting clear, orange solution was stirred at 0° C. for 30 min followed by addition of KI (0.055 mol) as a solution in H$_2$O (50 mL) keeping the internal temperature below 10° C. The black suspension was allowed to reach room temperature and stirred for 12 h. The suspension was extracted with DCM, washed with water and brine, dried over with Mg$_2$SO$_4$, concentration of the solution in vacuo gave a brown residue that was purified by column chromatography (hexane) to afford compound 137 (60%) as a yellow orange oil.

137: $^1$H-NMR (CD$_2$Cl$_2$, 250 MHz): 7.34 (s, 1H), 7.03 (s, 1H), 2.54 (s, 3H), 2.28 (s, 3H).

Compound 138:

A 50 mL round bottomflask equipped with a magnetic stir bar was charged with compound 137 (35 mmol), THF (100 mL), triethylamine (20 mL, 150 mmol), PdCl$_2$(PPh$_3$)$_2$ (500 mg, 0.7 mmol), CuI (150 mg, 0.754 mmol) and trimethylsilylacetylene (5.25 mL, 37.1 mmol) under argon atmosphere. The reaction mixture was stirred overnight at room temperature, diluted in CH$_2$Cl$_2$, washed with NH$_4$Cl and dried over Mg$_2$SO$_4$. The solvent was removed under reduced pressure and the crude product was purified by flash chromatography on silica gel with hexanes as eluent to afford the desired compound 138 (82%) as yellow solid.

138: $^1$H-NMR (CD$_2$Cl$_2$, 250 MHz): 7.43 (s, 1H), 7.13 (s, 1H), 2.58 (s, 3H), 2.32 (s, 3H), 0.28 (s, 9H);

Compound 139:

To a dimethylformamide (DMF) (100 mL) solution of compound 138 (32.3 mmole) placed in round bottom flask was added CuCl (32.3 mmol) equipped with a magnetic stirring bar. The reaction mixture was stirred for 6 h at 80° C. and quenched with 1.0 M HCl(aq). The aqueous layer was separated and extracted with 100 mL of diethyl ether. The combined ethereal layer was washed with brine and dried over Mg$_2$SO$_4$, concentration of the solution in vacuo gave a brown residue that was purified by column chromatography (dichloromethane/hexane=⅛) to afford compound 139 (78%) as a yellow solid.

139: $^1$H-NMR (CD$_2$Cl$_2$, 250 MHz): 7.23 (s, 1H), 6.95 (s, 1H), 2.39 (s, 3H), 2.23 (s, 3H). FD-MS (8 KV): 415.7 m/z.

Compound 140:

A 250 mL round bottom flask equipped with a magnetic stir bar was charged with compound 139 (11.9 mmol), THF (100 mL). The temperature was cooled to -78° C. and n-BuLi (1.4 mL, 47.4 mmol) was added slowly. The reaction mixture was stirred for one hour and 1,2-diiodoethane was added (35.6 mmol). The reaction mixture was stirred overnight at room temperature, diluted in CH$_2$Cl$_2$, washed with H$_2$O and dried over Mg$_2$SO$_4$. The solvent was removed under reduced pressure and the crude product was purified by column chromatography (dichloromethane/hexane=⅛) to afford the desired compound 140 (80%) as yellow solid.

140: $^1$H-NMR (CD$_2$Cl$_2$, 250 MHz): 7.48 (s, 1H), 6.97 (s, 1H), 2.41 (s, 3H), 2.20 (s, 3H). FD-MS (8 KV): 509.8 m/z.

Compound 141:

Nitrogen was bubbled through a mixing solution of THF (100 mL), EtOH (20 mL) and water (20 mL) for 30 min, and to this solution was added compound 140 (4.96 mmol), Pd(PPh$_3$)$_4$ (0.5 mmol), K$_2$CO$_3$ (29.76 mmol) and bromonaphthalene-boronic acid (9.95 mmol). The mixture was heated at 60° C. for 36 h. The solution was extracted three times with ethyl acetate. After removal of the solvent in vacuo, the crude material was purified by column chromatography (dichloromethane/hexane=⅛) to afford compound 141 (56%) as a yellow solid.

141: $^1$H-NMR (CD$_2$Cl$_2$, 250 MHz): 8.13 (s, 1H), 7.98 (s, 1H), 8.00 (s, 1H), 7.83 (t, 1H), 7.72 (d, 3H), 7.61 (t, 1H), 7.37 (t, 1H), 7.11 (s, 1H), 6.98 (s, 1H), 2.39 (s, 3H), 2.35 (s, 3H). FD-MS (8 KV): 667.9 m/z.

Compound 142:

A solution of compound 141 (1.55 mmol) in dry CH$_2$Cl$_2$ (100 mL) was maintained at -78° C. with an acetone-liquid N2 bath. To this solution was added ICl (3.41 mL, 1 M solution in CH$_2$Cl$_2$), using a standard syringe. The reaction was stirred for 3 h. Quenched with a saturated sodium sulfite solution and warmed to RT. Extracted with CH$_2$Cl$_2$ (2×30 mL) and dried over MgSO$_4$. After removal of solvent in vacuo, the crude material was purified by column chromatography (dichloromethane/hexane=⅛) to afford compound 142 (87%) as a yellow solid.

142: $^1$H-NMR (CD$_2$Cl$_2$, 250 MHz): 8.91 (s, 1H), 7.89 (s, 1H), 7.47 (d, 1H), 7.26 (s, 1H), 7.22 (dd, 1H), 7.17 (dd, 1H), 6.70 (t, 1H), 2.70 (s, 3H), 2.48 (s, 3H); 13C-NMR (CD2Cl2, 250 MHz): 149.46, 134.66, 134.37, 132.61, 132.34, 131.41, 131.36, 131.05, 130.75, 130.09, 127.41, 126.54, 125.43, 125.15, 123.75, 122.86, 114.75, 100.49, 24.56, 20.40. FD-MS (8 KV): 919.9 m/z.

Monomer 8:

A solution of 142 (0.108 mmol) in dry THF (100 mL) was irradiated in a standard immersion well photoreactor with 360 nm high pressure mercury vapor lamp (4*360 nm) for 2 h. The reaction mixture was then washed with aqueous sodium thiosulfate, water, brine and dried over anhydrous $MgSO_4$. The solvent was removed under vacuum and recrystallization from chloroform afforded monomer 8 (50%) as a yellow solid.

8: $^1$H-NMR ($CD_2Cl_2$, 250 MHz): 9.21 (s, 1H), 8.30 (s, 1H), 8.00 (s, 1H), 7.73 (dd, 1H), 7.32 (m, 3H), 6.79 (t, 1H), 2.64 (s, 3H), 2.56 (s, 3H); $^{13}$C-NMR (CD2Cl2, 250 MHz): 139.12, 134.39, 134.24, 133.91, 132.78, 131.13, 130.42, 130.09, 129.85, 129.65, 129.58, 128.00, 127.86, 126.97, 126.72, 125.78, 125.39, 117.47, 22.34, 19.91. FD-MS (8 KV): 667.8 m/z.

7. Surface Confined Preparation of GNR v-vii (R=H)

A Au (111) single crystal (Surface Preparation Laboratory, Netherlands) was used as the substrate for the growth of the GNR structures v, vi and vii from the corresponding monomers 5, 6 and 7, respectively. The Au surface was cleaned under ultra-high vacuum conditions (UHV, pressure $1\times10^{-10}$ mbar) by repeated cycles of argon ion bombardment and annealing to 470° C. Once the surface was clean, the precursor monomers were deposited onto the substrate held at 200° C. by sublimation at rates of ~0.1 nm/min. After monomer deposition, the Au (111) substrate was kept at this temperature for a few minutes (1-15 min) to complete polymerization. Subsequently the sample was annealed to 400° C. for 15 min to induce cyclodehydrogenation and thus the formation of the targeted GNR structures. A variable-temperature STM (VT-STM) from Omicron Nanotechnology GmbH, Germany, was used to characterize the morphology of the GNR structures. Images were taken at 35 K (LHe cooling).

Figure 2:
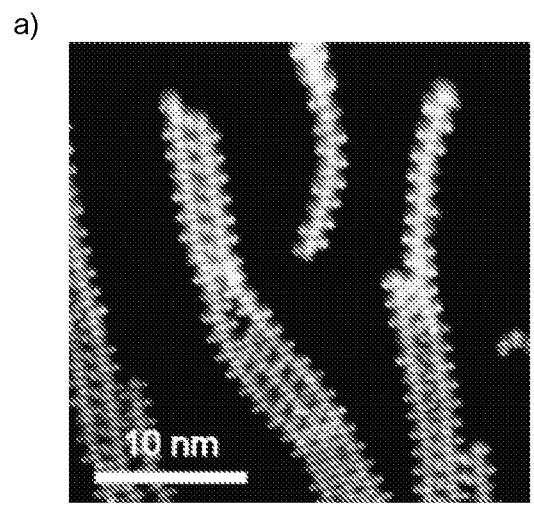
FIG. 2a shows an STM image (U=1 V, I=0.03 nA) obtained after deposition of the precursor monomer 2 and polymerization
FIG. 2b shows an STM image (U=−1V, I=0.03 nA) of the final GNR structure vi after cyclodehydrogenation
Figure 2:
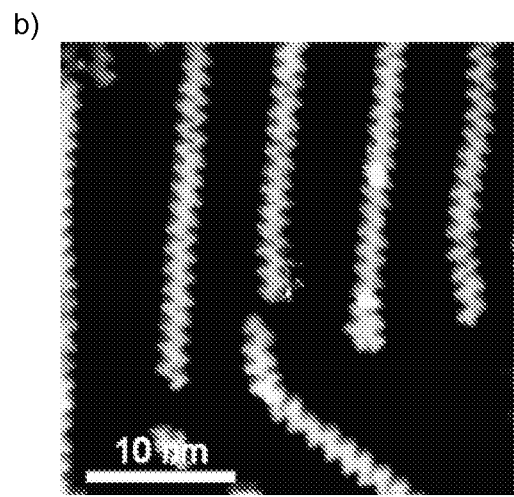
Figure 3:
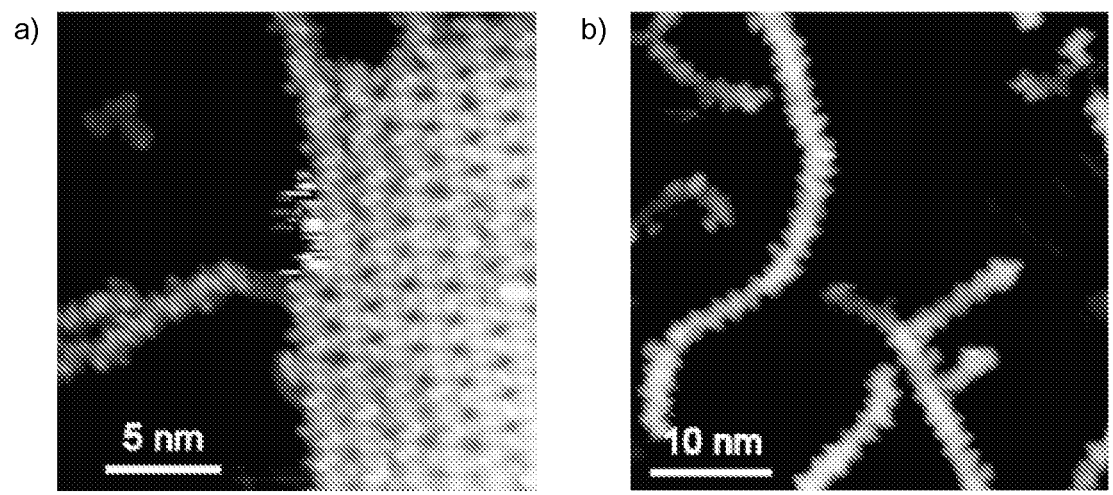
FIG. 3a shows an STM image (U=1 V, I=0.02 nA) obtained after deposition of the precursor monomer 3 and polymerization
FIG. 3b shows an STM image (U=1V, I=0.02 nA) of the final GNR structure vii after cyclodehydrogenation
Figure 4:
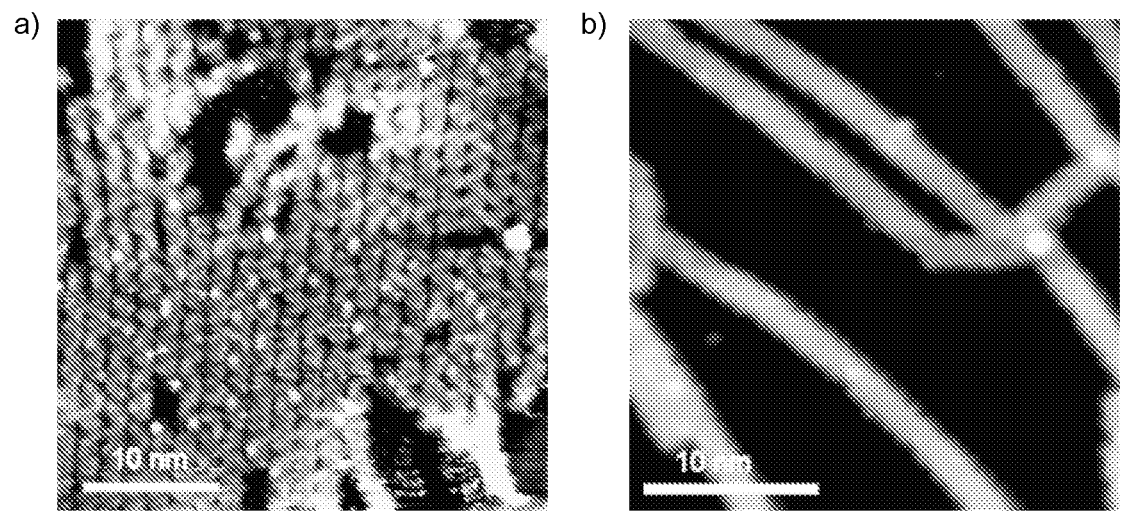
FIG. 4a shows STM image (c, U=1 V, 1=0.06 nA) obtained after deposition of the precursor monomer 1 and polymerization
FIG. 4b shows an STM image (U=2.9 V, 1=0.1 nA) of the final GNR structure v after cyclodehydrogenation
Figure 5A:
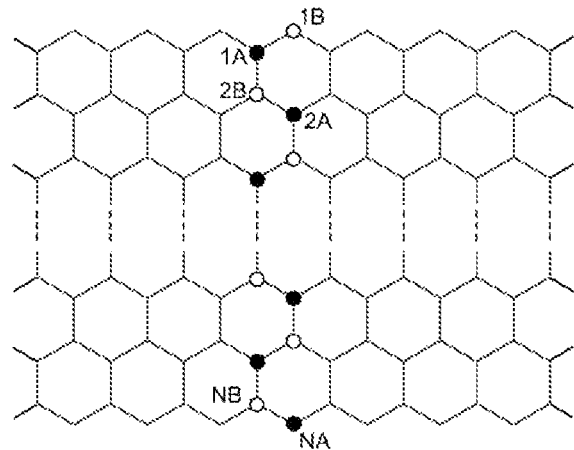
FIG. 5 shows the method for defining the width N of (a) zig-zag-type, (b) cove-type, and (c) armchair-type GNR as used herein and illustrates the A and B sublattices of the GNR.
Figure 5B:
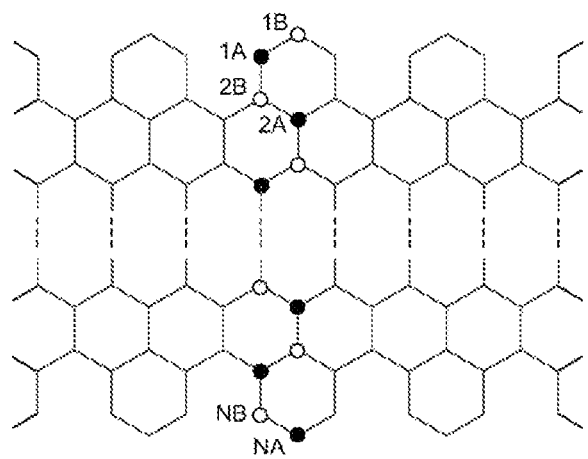
Figure 5C:
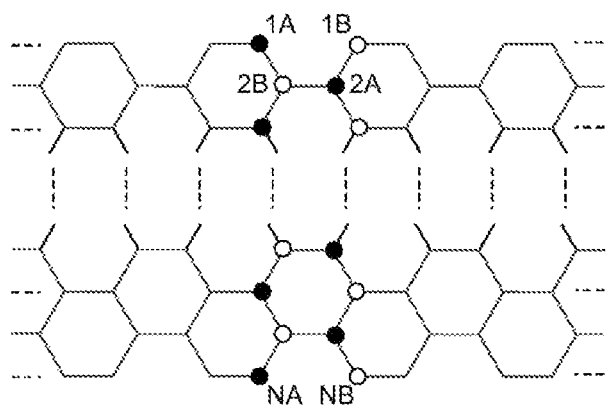
Figure 6:
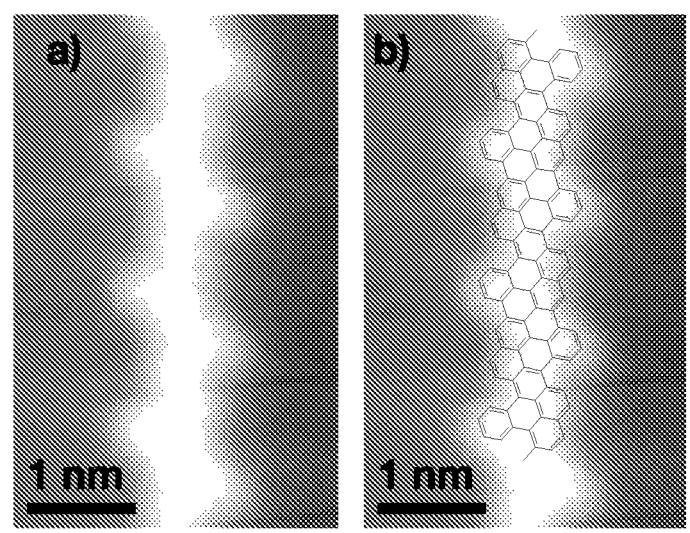
FIG. 6a shows an STM image of GNR structure i fabricated on a Au (111) surface from monomer 9 (U=−1.0 V, 1=0.03 nA).
FIG. 6b shows the same STM image as shown in FIG. 6a with a chemical model of the GNR structure superimposed.

FIGS. 2, 3 and 4 show STM images of the polymer structures obtained after monomer deposition (a) and of the final GNR structures (b) obtained after cyclodehydrogenation. The characteristic apparent height of the final GNR structures is of 0.17 to 0.20 nm, in agreement with other GNR structures [e.g. Nature 466, 470-473 (2010)].

The experiments are summarized in Table 1.

TABLE 1

| Molecule | Intermediate Polymer | Graphene Nanoribbon |
|---|---|---|
| monomer 2 | Fig. 2a | Fig. 2b |
| monomer 3 | Fig. 3a | Fig. 3b |

TABLE 1-continued
| Molecule | Intermediate Polymer | Graphene Nanoribbon |
|---|---|---|
| 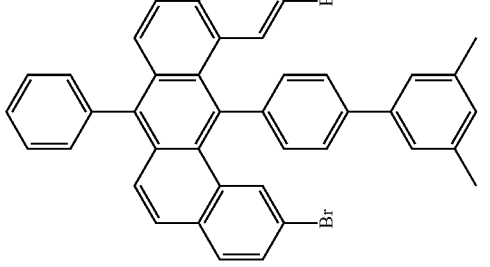 monomer 1 | Fig. 4a | Fig. 4b |

8. Preparation of GNR iii (R═H) from Monomer 6

A Au (111) single crystal (Surface Preparation Laboratory, Netherlands) was used as the substrate for the growth of the N=5 cove-edge zigzag GNR structure iii from monomer 3. The Au surface was cleaned under ultra-high vacuum conditions (UHV, pressure $1 \times 10^{-10}$ mbar) by repeated cycles of argon ion bombardment and annealing to 470° C. Once the surface was clean, the precursor monomers 3 were deposited onto the substrate held at 200° C. by sublimation at rates of ~0.1 nm/min. After monomer deposition, the Au (111) substrate was kept at this temperature for a few minutes (1-15 min) to complete polymerization. Subsequently the sample was annealed to 450° C. for 15 min to induce cyclodehydrogenation and thus the formation of the targeted GNR structure iii. A low-temperature scanning tunneling microscope (LT-STM) from Omicron Nanotechnology GmbH, Germany, was used to characterize the morphology of the N=5 cove-edge zigzag GNR structures. Images were taken at 5 K (LHe cooling).

FIG. 1 a) shows a high resolution STM image of the terminus of the GNR structure iii. The image was taken at U=−0.9V, I=0.4 nA, 5 K (LHe cooling). The apparent height is 0.17 nm, in agreement with results for other GNR structures [e.g. Nature 466, 470-473 (2010)].

FIG. 1 b) shows the same STM image with a chemical model of the corresponding GNR structure iii overlaid.

9. Preparation of GNR i (R═H) from Monomer 9

A Au (111) single crystal (Surface Preparation Laboratory, Netherlands) was used as the substrate for the growth of the GNR structure i from monomer 9. The Au surface was cleaned under ultra-high vacuum conditions (UHV, pressure $1 \times 10^{-10}$ mbar) by repeated cycles of argon ion bombardment and annealing to 470° C. Once the surface was clean, the precursor monomers 9 were deposited onto the substrate held at 170° C. by sublimation at rates of ~0.1 nm/min. After monomer deposition, the Au (111) substrate was kept at this temperature for a few minutes (1-15 min) to complete polymerization. Subsequently the sample was annealed to 370° C. for 15 min to induce cyclodehydrogenation and thus the formation of the targeted GNR structure i. A variable-temperature STM (VT-STM) from Omicron Nanotechnology GmbH, Germany, was used to characterize the morphology of the GNR structures. Images were taken at 35 K (LHe cooling).

The invention claimed is:

1. A graphene nanoribbon, represented by structure (i), structure (ii), structure (iii), structure (iv), structure (v), structure (vi), structure (vii), structure (viii), or structure (ix):

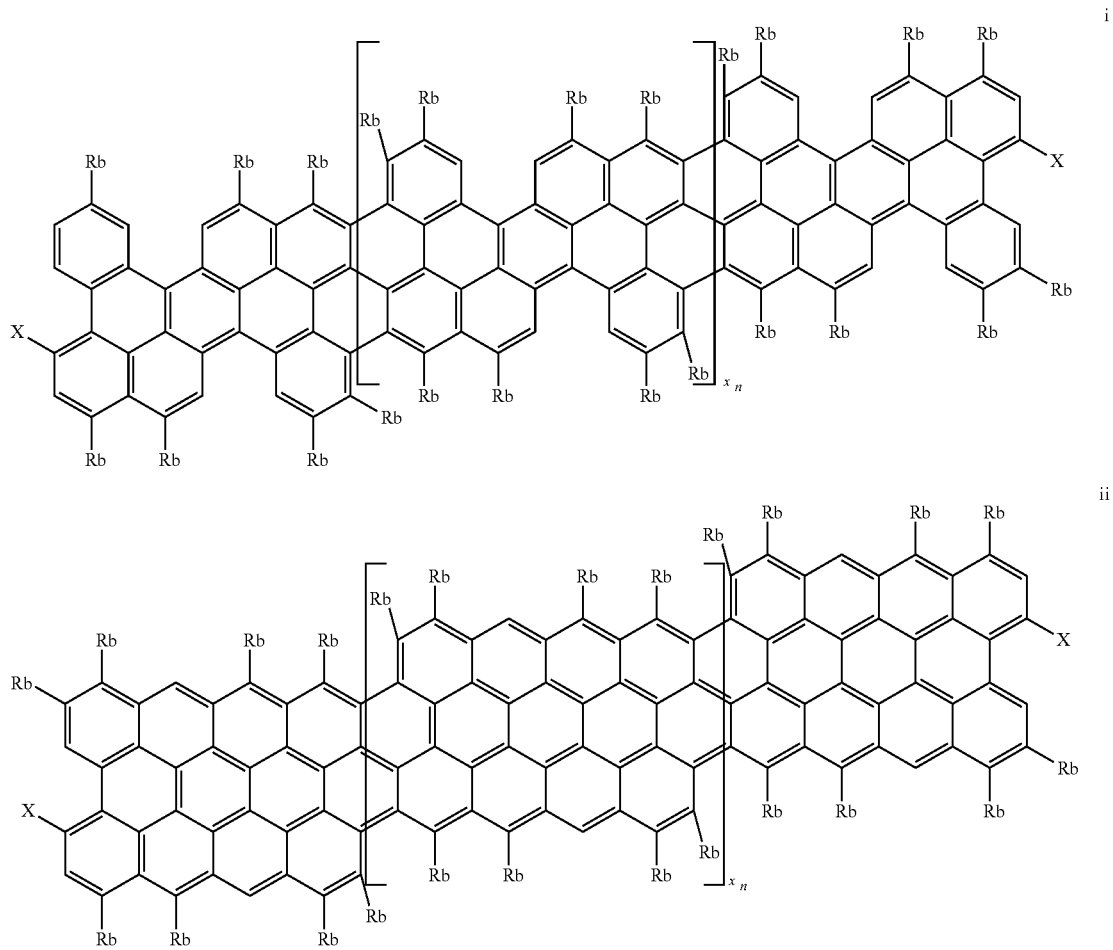

-continued
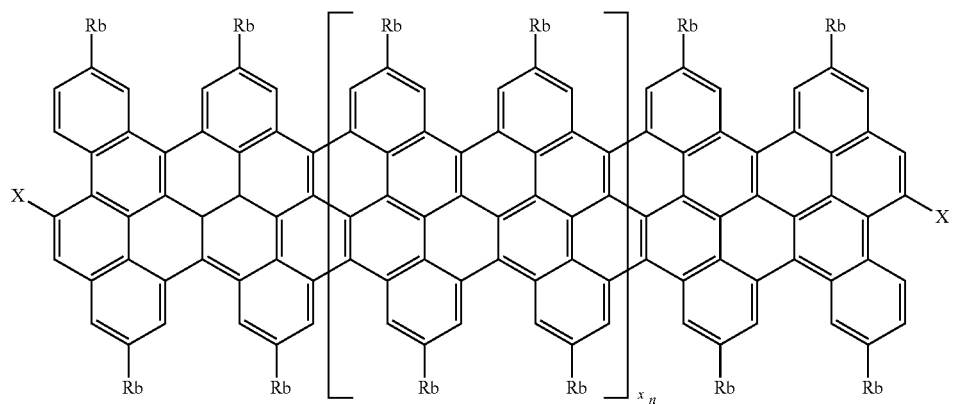
iii
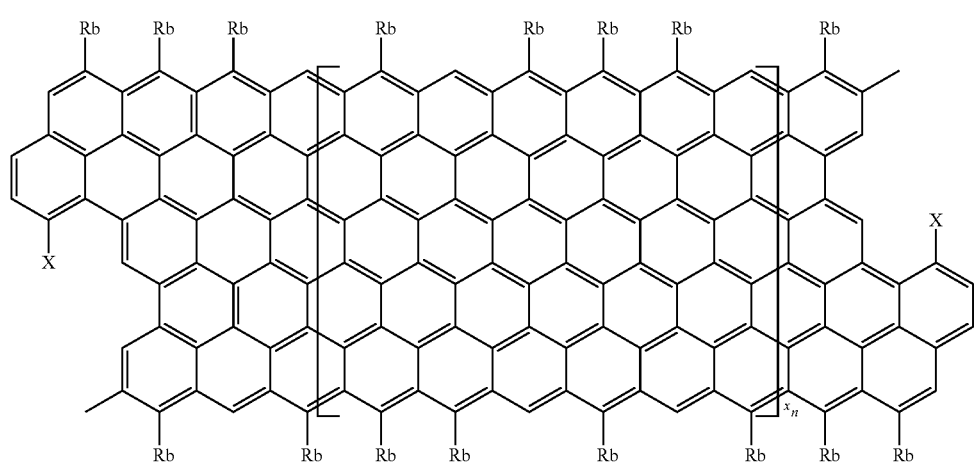
iv
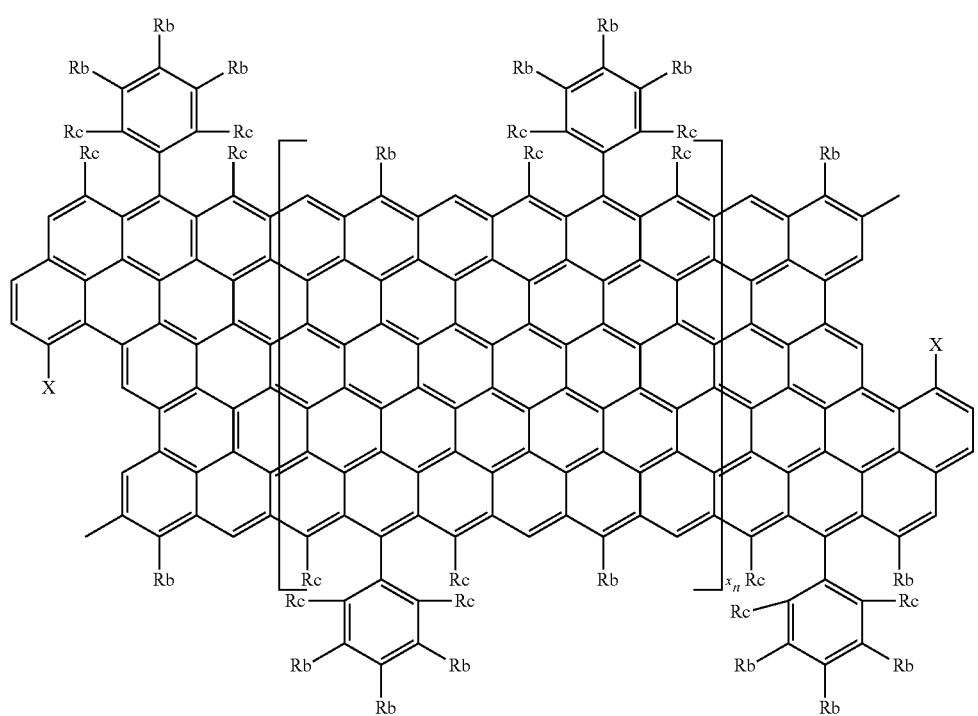
v

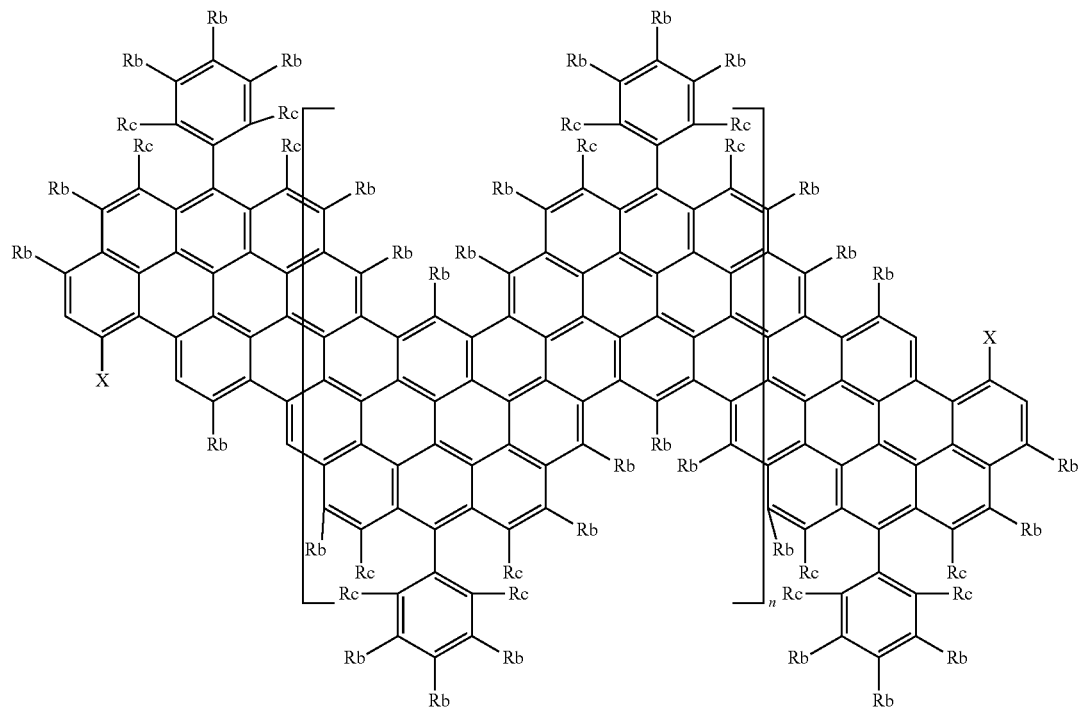
vi
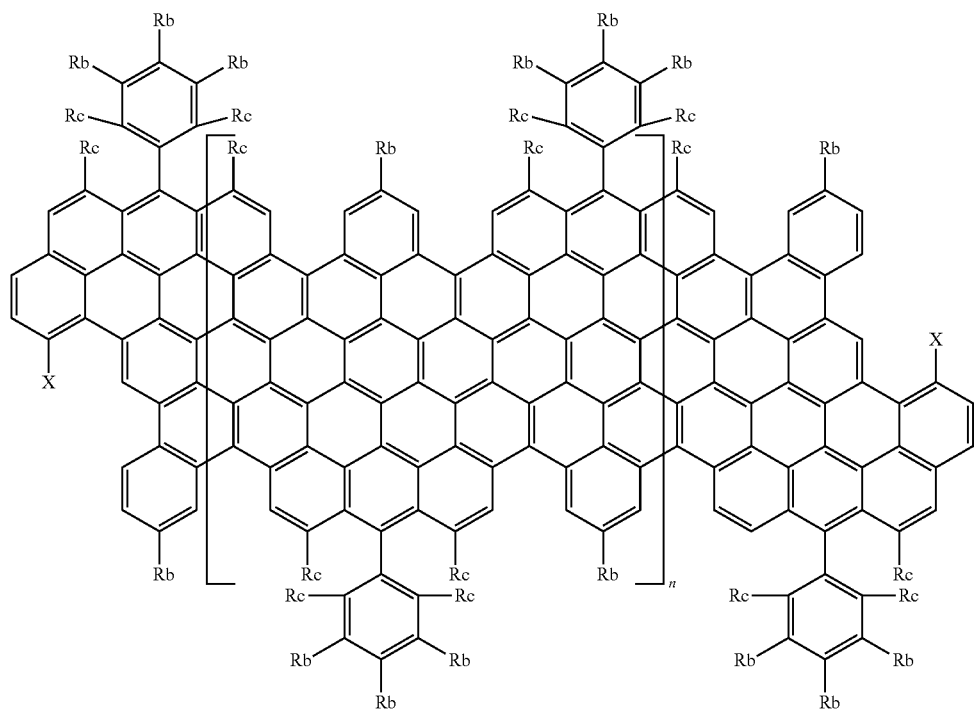
vii

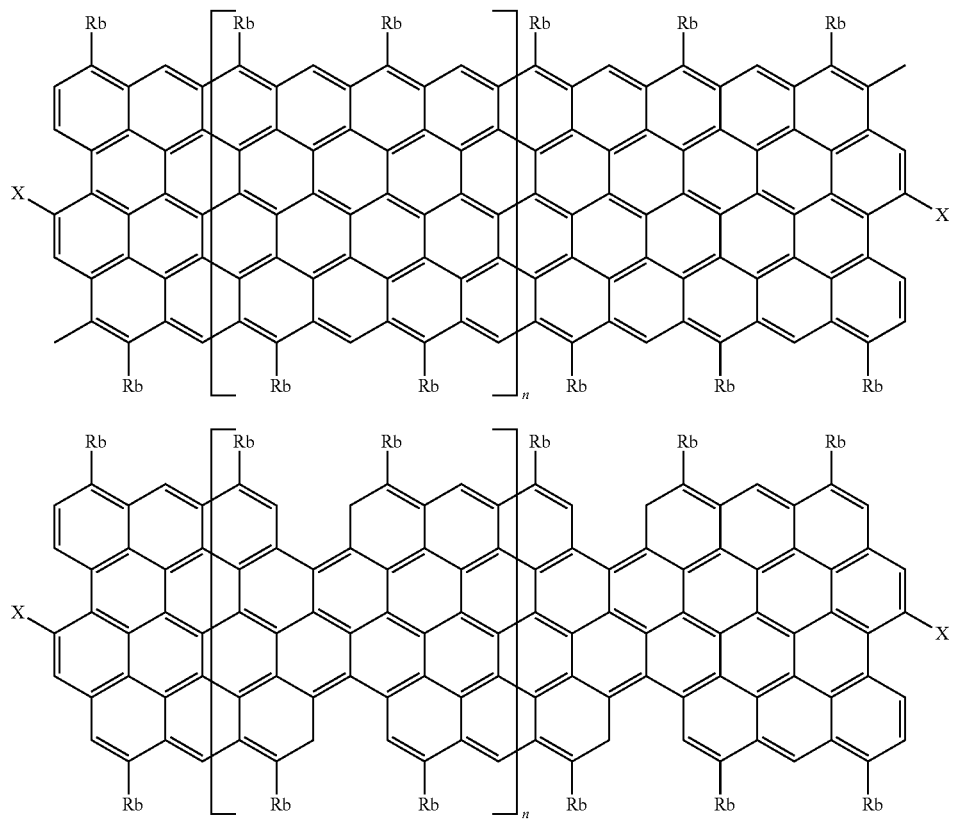

wherein:
X independently from each other, are a leaving group, hydrogen, or a free radical;
$R^b$ independently from each other are hydrogen, a linear $C_1$-$C_{30}$ alkyl, a branched $C_1$-$C_{30}$, alkyl, $OR_3$ or $NR_1R_2$; wherein:
  $R_1$ and $R_2$ are, independently of each other, hydrogen, a linear $C_1$-$C_6$alkyl, a branched $C_1$-$C_6$alkyl, or phenyl, or $R_1$ and $R_2$ together with the nitrogen atom to which they are bonded form a group represented by

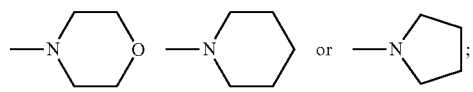

and
  $R_3$ is selected from hydrogen, $C_1$-$C_{30}$ alkyl and phenyl, which may be unsubstituted or substituted by one or more $C_1$-$C_4$ alkyl, phenyl, halogen, $C_1$-$C_4$ alkoxy or $C_1$-$C_4$ alkylthiol; or
$R^b$ is alpha-hydrogen substituted aryl that may form a 5-membered carbocyclic ring with a neighboring hydrogen substituted edge carbon by cycloannelation; or
one of two direct neighboring groups $R^b$ is an alpha-hydrogen substituted aryl and the other is hydrogen, and the two carbon atoms substituted with hydrogen may form a 5-membered carbocyclic ring by cycloannelation,
$R^c$ independently of each other, are hydrogen or $C_1$-$C_{10}$ alkyl; or two neighboring groups $R^c$ are hydrogen, and the two carbon atoms substituted with hydrogen may form a 5-membered carbocyclic ring by cycloannelation; and
n is an integer of from 2 to 2500.

2. The graphene nanoribbon according to claim 1, represented by structure (i).

3. The graphene nanoribbon according to claim 1, represented by structure (ii).

4. The graphene nanoribbon according to claim 1, represented by structure (iii).

5. The graphene nanoribbon according to claim 1, represented by structure (iv).

6. The graphene nanoribbon according to claim 1, represented by structure (vi).

7. The graphene nanoribbon according to claim 1, represented by structure (vii).

8. The graphene nanoribbon according to claim 1, represented by structure (viii).

9. The graphene nanoribbon according to claim 1, represented by structure (ix).

10. A process for preparing the graphene nanoribbon according to claim 1, the process comprising:
  (a) providing at least one aromatic monomer compound, which is at least one substituted or unsubstituted polycyclic aromatic monomer compound, at least one substituted or unsubstituted oligo phenylene aromatic monomer compound, or any combination thereof, on a solid substrate;
  (b) polymerizing of the aromatic monomer compound so as to form at least one polymer on the surface of the solid substrate; and (c) at least partially cyclodehydrogenating the one or more polymers of said (b) polymerization to obtain the graphene nanoribbon having structure (i), structure (ii), structure (iii), structure (iv), structure (v), structure (vi), structure (vii), structure (viii), or structure (ix).

11. A process for preparing the graphene nanoribbon according to claim 1, the process comprising:
(a) providing at least one aromatic monomer compound which is at least one substituted or unsubstituted polycyclic aromatic monomer compound, at least one substituted or unsubstituted oligo phenylene aromatic monomer compound, or any combination thereof, in solution;
(b) polymerizing of the aromatic monomer compound so as to form at least one polymer; and
(c) at least partially cyclodehydrogenating the one or more polymers of said (b) polymerization to obtain the graphene nanoribbon having structure (i), structure (ii), structure (iii), structure (iv), structure (v), structure (vi), structure (vii), structure (viii), or structure (ix).

* * * * *

UNITED STATES PATENT AND TRADEMARK OFFICE
CERTIFICATE OF CORRECTION

| | | |
|---|---|---|
| PATENT NO. | : 10,329,378 B2 | Page 1 of 8 |
| APPLICATION NO. | : 15/118796 | |
| DATED | : June 25, 2019 | |
| INVENTOR(S) | : Matthias Georg Schwab et al. | |

It is certified that error appears in the above-identified patent and that said Letters Patent is hereby corrected as shown below:

On the Title Page

On page 2, Column 2, item (56), other publications, Lines 43-44, "English translation" should read -- English language translation --.

In the Specification

Column 2, Line 31, "atom)" should read -- atom --.

Column 4, Line 56, "or I," should read -- or I; --.

Column 5, Line 6, "$C_1$-$C_4$-alkyl," should read -- $C_1$-$C_4$alkyl, --.

Column 6, Line 59, "ore" should read -- are --.

Column 11, Line 44, "or I," should read -- or I; --.

Column 11, Line 61, "$C_1$-$C_4$-alkyl" should read -- $C_1$-$C_4$alkyl --.

Column 15, Line 49, "$C_1$-$C_4$-alkyl," should read -- $C_1$-$C_4$alkyl, --.

Column 24, Lines 31-32, "cyclodehydrogenization" should read -- cyclodehydrogenation --.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*

Columns 23 and 24, the structure should read:
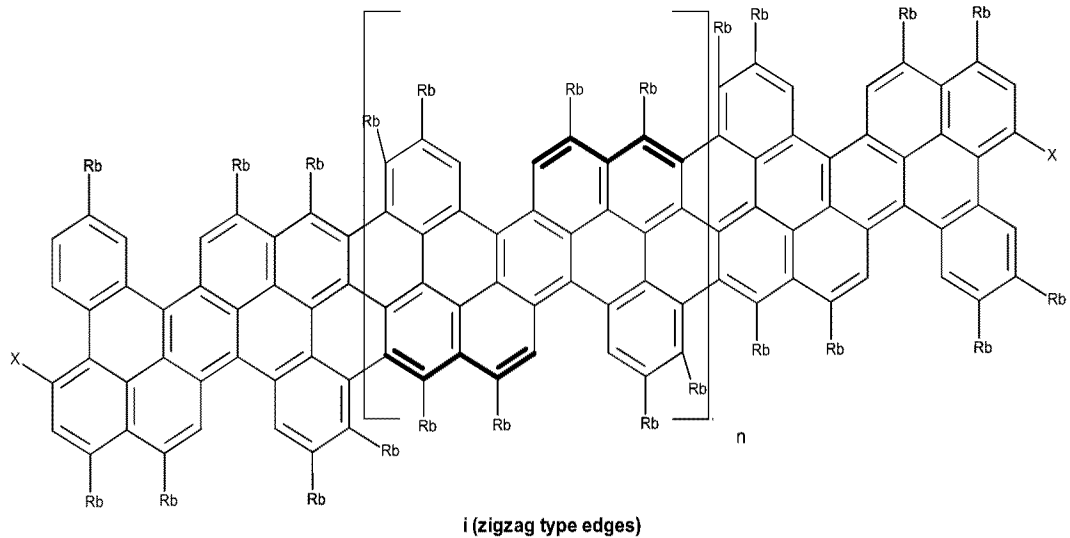
Columns 25 and 26, the structure should read:
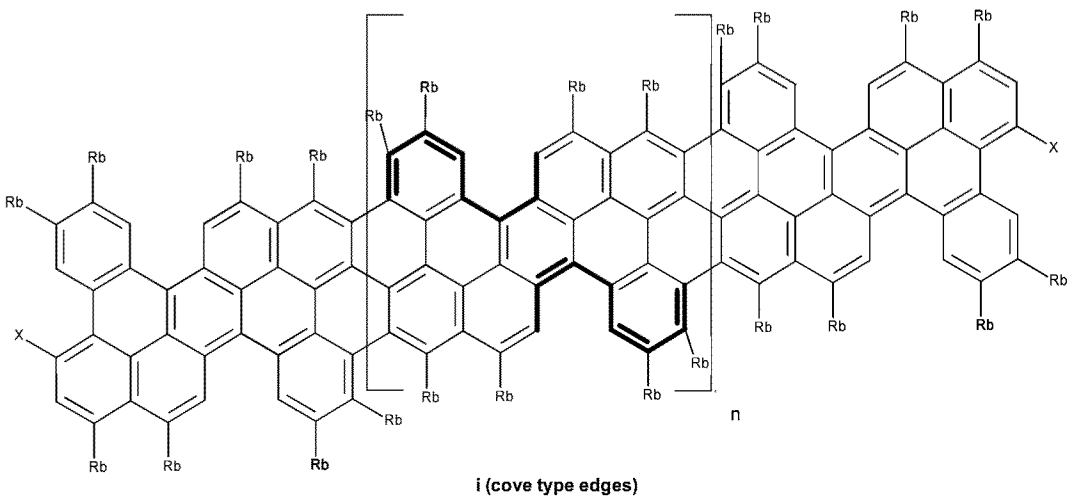
Graphene nanoribbon structure ii contains zigzag type edges and armchair type edges in the repeating unit RU1.

CERTIFICATE OF CORRECTION (continued)
U.S. Pat. No. 10,329,378 B2

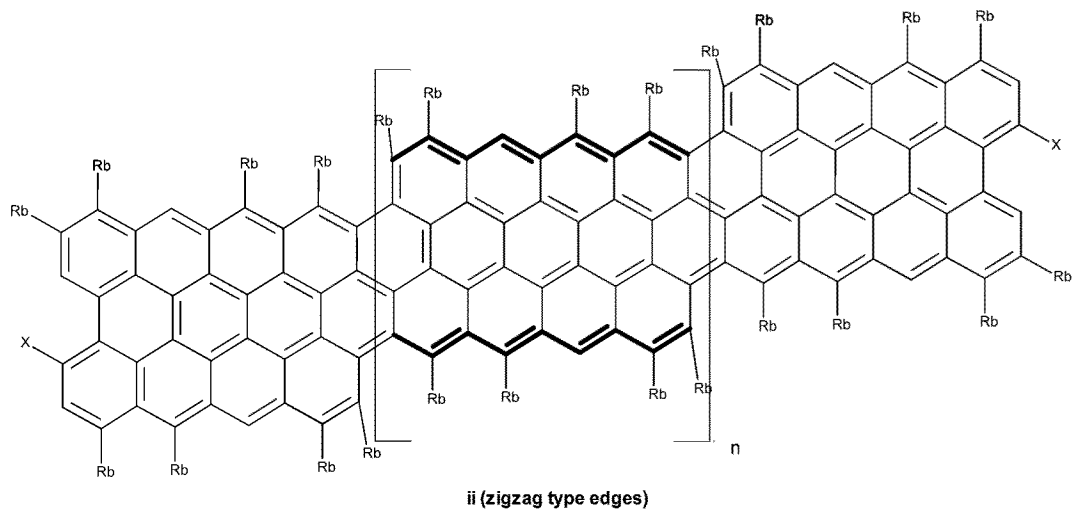

ii (zigzag type edges)

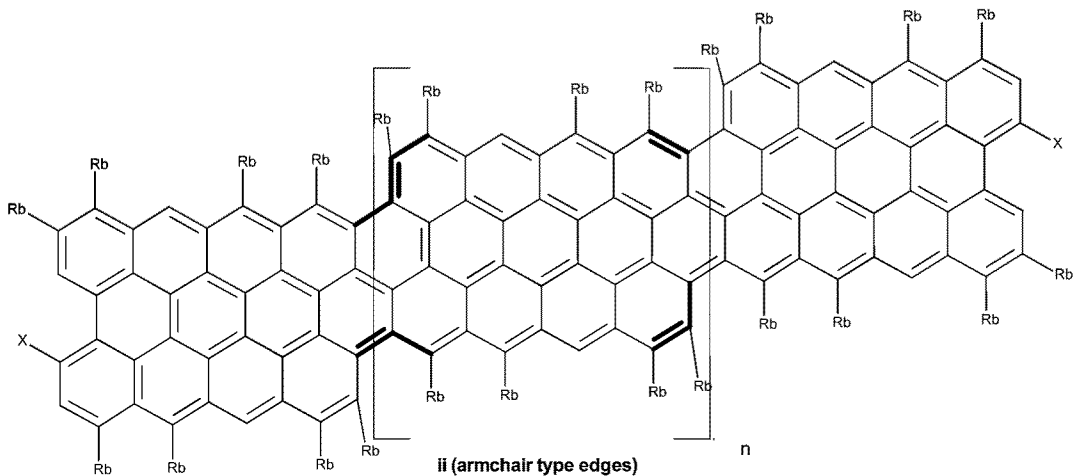

ii (armchair type edges)

--.

Columns 27 and 28, should read:
-- Graphene nanoribbon structure iii contains exclusively cove type edges in the repeating unit RU1.

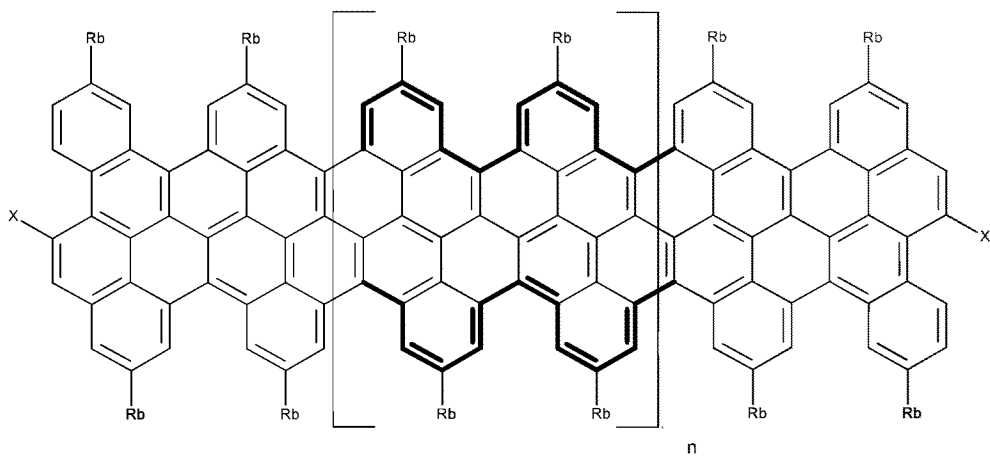

iii (cove type edges)

Graphene nanoribbon structure iv contains exclusively zigzag type edges in the repeating unit RU1.

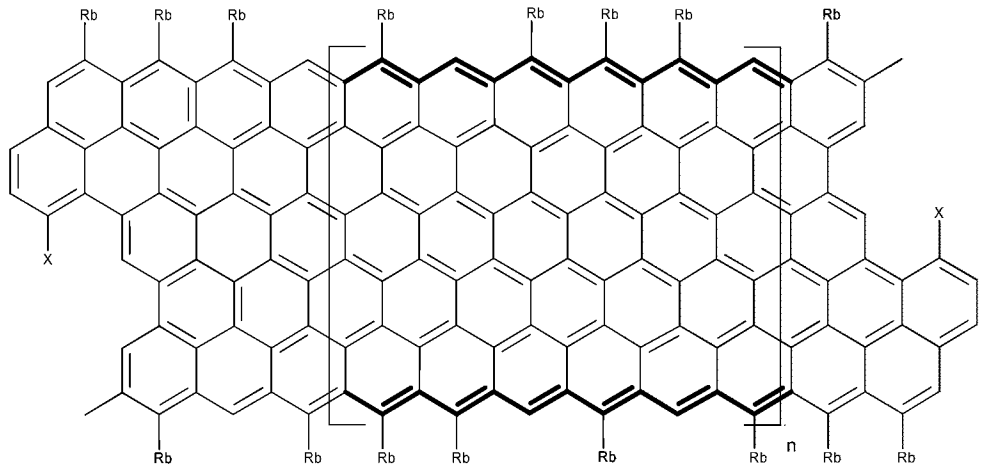

iv (zigzag type edges)

Graphene nanoribbon structure v contains exclusively zigzag type edges in the repeating unit RU1. --.

Columns 29 and 30, should read:

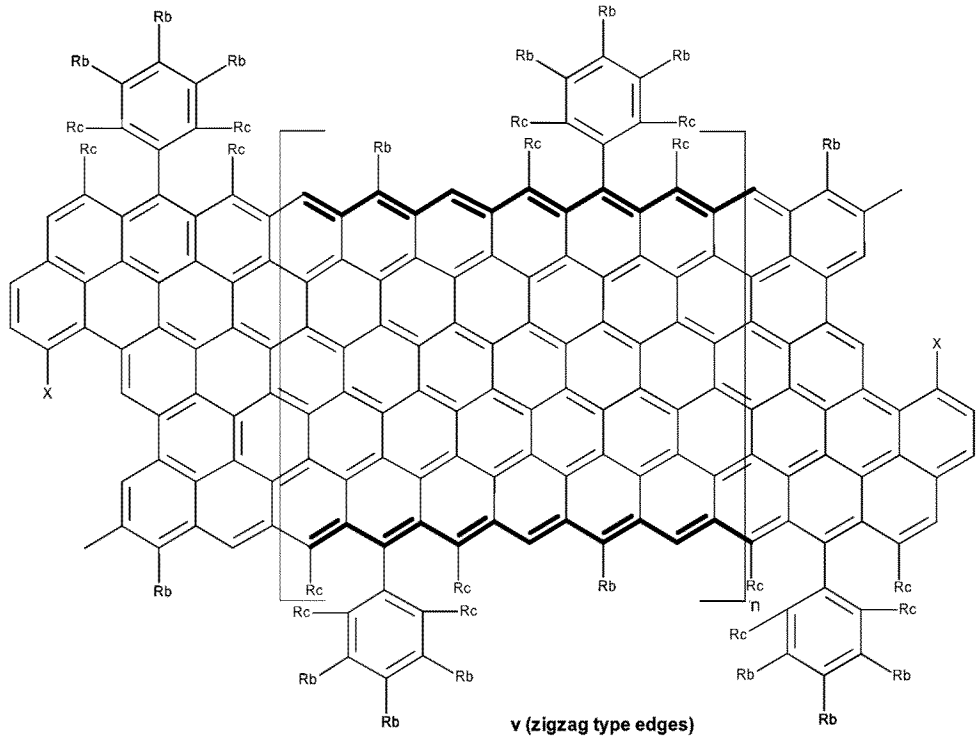

v (zigzag type edges)

--
Graphene nanoribbon structure vi contains zigzag type edges and edges which can neither be assigned as zigzag, armchair, nor cove type edges in the repeating unit RU1.

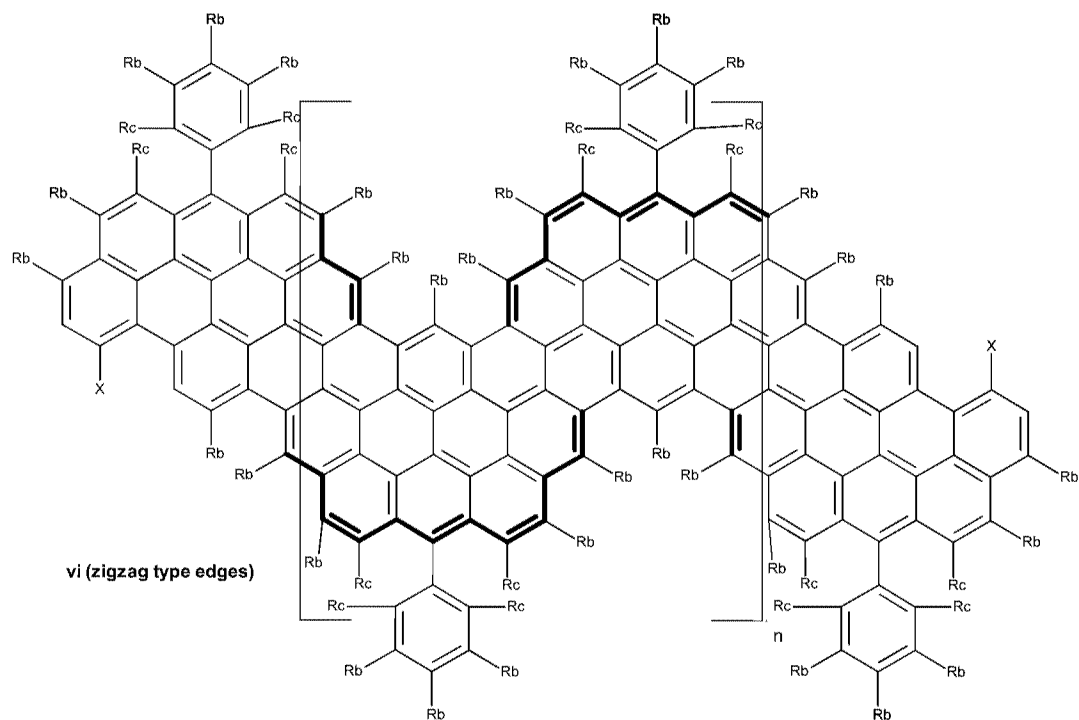
Columns 31 and 32, should read:
-- Graphene nanoribbon structure vii contains cove type edges and zigzag type edges in the repeating unit RU1.
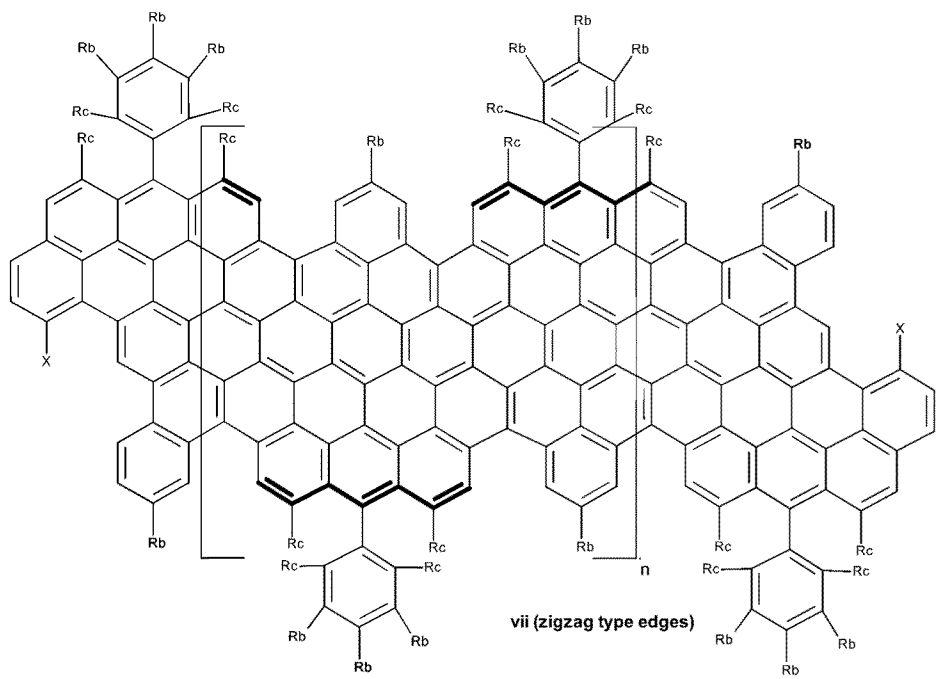

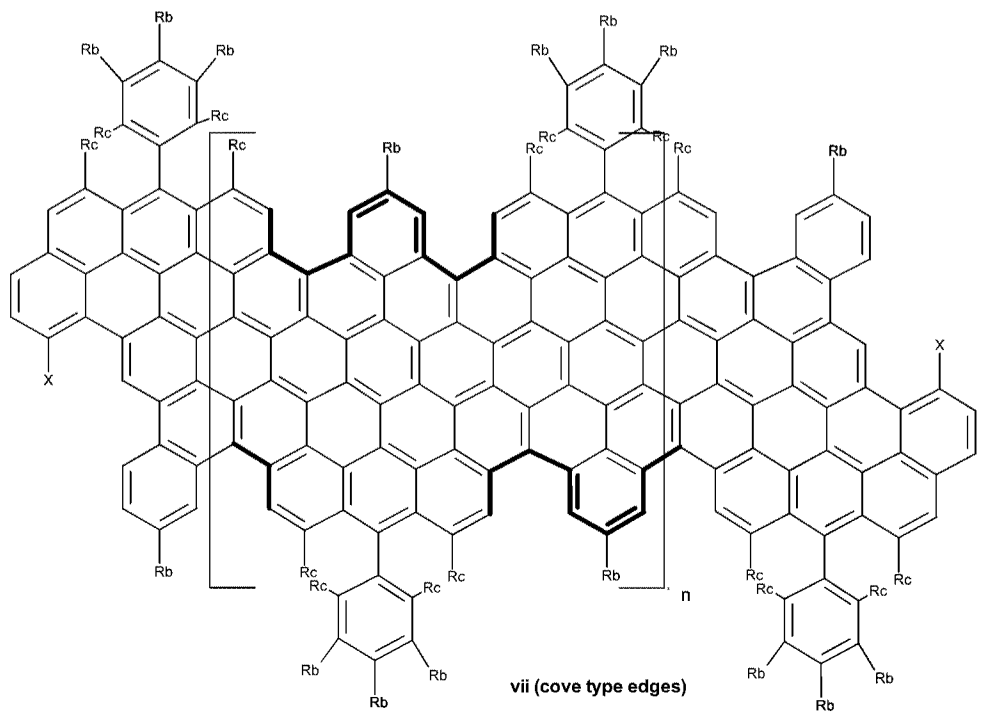
vii (cove type edges)
Graphene nanoribbon structure viii is derived of monomer VIII or X and contains exclusively zigzag type edges in the repeating unit RU1 --.
Columns 33 and 34, Lines 1-23 should read:
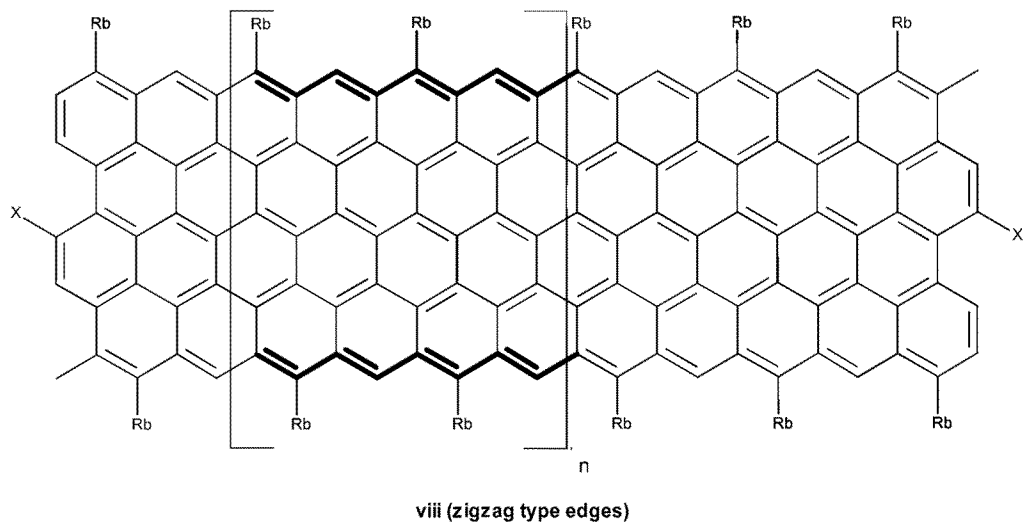
viii (zigzag type edges)
--
Graphene nanoribbon structure ix is derived of monomer IX and contains zigzag type edges and cove type edges in the repeating unit RU1

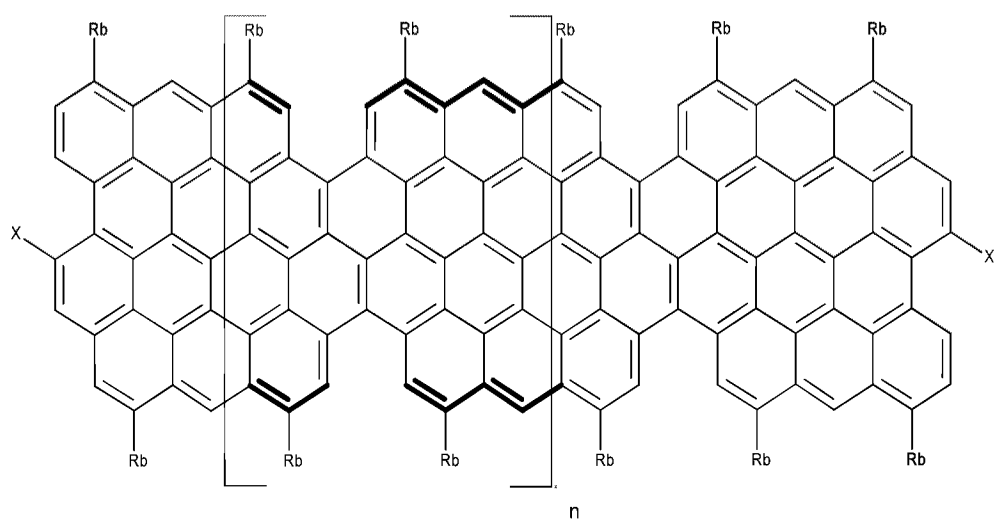

ix (zigzag type edges)

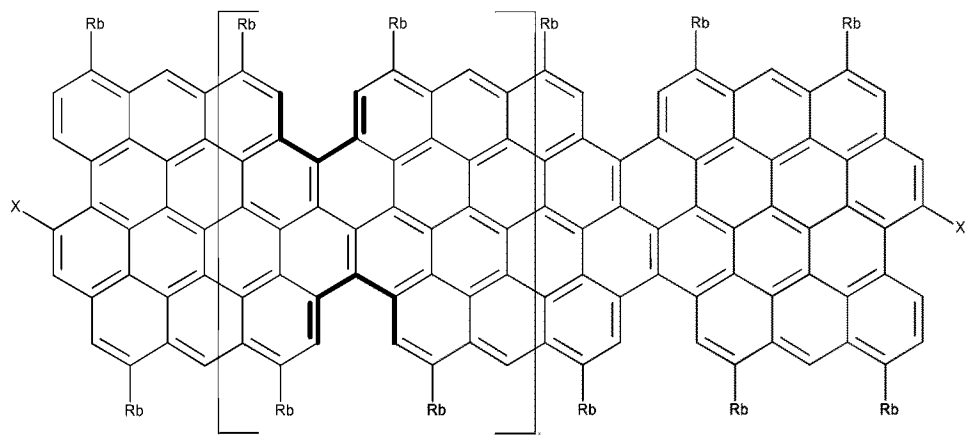

ix (cove type edges)

--.

Column 33, Lines 62-67, "In particular embodiments aromatic groups in the GNR structures above or substituents $R^b$ and/or $R^c$ may react with other groups so as to form a 5 membered carbocyclic ring.
Therefore, if in the GNR precursor polymer two neigh- boring groups $R^c$ are hydrogen, the two carbon atoms" should read -- In particular embodiments aromatic groups in the GNR structures above or substituents $R^b$ and/or $R^c$ may react with other groups so as to form a 5 membered carbocyclic ring.
Therefore, if in the GNR precursor polymer two neighboring groups $R^c$ are hydrogen, the two carbon atoms substituted with hydrogen may form a 5-membered carbocyclic ring by cycloannelation (see e.g. in GNR structure vii), --.

Column 35, Line 17, "M," should read -- $M_w$ --.

Column 35, Line 31, "polymerization" should read -- polymerization. --.

CERTIFICATE OF CORRECTION (continued)
U.S. Pat. No. 10,329,378 B2

Column 36, Line 2, "cyclodehydrogenation" should read -- cyclodehydrogenation. --.

Column 36, Line 5, "polymerization" should read -- polymerization. --.

Column 36, Line 7, "cyclodehydrogenation" should read -- cyclodehydrogenation. --.

Column 36, Line 10, "polymerization" should read -- polymerization. --.

Column 36, Line 12, "cyclodehydrogenation" should read -- cyclodehydrogenation. --.

Column 39, Line 9 approx., "Dichlormethane" should read -- dichloromethane --.

Column 41, Line 14, "terafluoroboric" should read -- tetrafluoroboric --.

Column 44, Line 13, "silca" should read -- silica --.

Column 45, Line 50, "cyclodehyrogenation" should read -- cyclodehydrogenation --.

Column 50, Line 44, "i":4",1""" should read -- i":4",1''' --.

Column 51, Line 30, "[1,11" should read -- [1,1' --.

Column 52, Line 66, "bottomflask" should read -- bottom flask --.

Column 57, Line 40, "bottomflask" should read -- bottom flask --.

Column 58, Line 63, "(CD2Cl2," should read -- ($CD_2Cl_2$, --.

Column 59, Line 12, "(CD2Cl2," should read -- ($CD_2Cl_2$, --.